(12) United States Patent
Huang et al.

(10) Patent No.: US 10,053,674 B2
(45) Date of Patent: *Aug. 21, 2018

(54) METHODS AND COMPOSITIONS USING FUNGAL LACCASES TO REDUCE TURF THATCH

(71) Applicant: University of Georgia Research Foundation, Inc., Athens, GA (US)

(72) Inventors: Qingguo Huang, Fayetteville, GA (US); Sudeep S. Sidhu, Dayton, NV (US); Paul L. Raymer, Milner, GA (US); Robert N. Carrow, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 138 days.

This patent is subject to a terminal disclaimer.

(21) Appl. No.: 14/580,625

(22) Filed: Dec. 23, 2014

(65) Prior Publication Data
US 2015/0121754 A1    May 7, 2015

Related U.S. Application Data

(63) Continuation-in-part of application No. 13/249,729, filed on Sep. 30, 2011, now Pat. No. 8,919,039.

(60) Provisional application No. 61/388,160, filed on Sep. 30, 2010.

(51) Int. Cl.
C12N 9/02      (2006.01)
A01G 20/00     (2018.01)

(52) U.S. Cl.
CPC .... C12N 9/0061 (2013.01); C12Y 110/03002 (2013.01); *A01G 20/00* (2018.02)

(58) Field of Classification Search
None
See application file for complete search history.

(56) References Cited

U.S. PATENT DOCUMENTS

| 6,506,956 | B1 | 1/2003 | Yuki et al. |
| 8,919,039 | B2 | 12/2014 | Huang et al. |
| 2008/0248016 | A1 | 10/2008 | Paloheimo et al. |
| 2009/0311752 | A1 | 12/2009 | Bodie et al. |

OTHER PUBLICATIONS

Sartain et al., Agronomy J. 76: 359-362 (1984).*
Lu et al., Process Biochem. 45(7): 1141-1147 (2010).*
Madhavi et al., BioResources 4(4): 1694-1717 (2009).*
Anatai, Sylvester P., and Crawford, Don L., Degradation of Extractive-free Lignocelluloses by Coriulus versicolor and Proia placenta, European J. Appl. Microbiol Biotechnol (1982) 14:165-168.

(Continued)

Primary Examiner — Erin M. Bowers
(74) Attorney, Agent, or Firm — Thomas | Horstemeyer, LLP

(57) ABSTRACT

The present disclosure includes methods and compositions for reducing turf thatch and/or preventing turf thatch buildup. The compositions include isolated fungal laccase enzymes, such as laccase enzymes from white rot fungi. Methods of reducing and/or preventing turf thatch buildup include applying compositions including isolated fungal laccase enzymes to turfgrass.

14 Claims, 16 Drawing Sheets

(56) References Cited

OTHER PUBLICATIONS

Sartain, J.B., and Volk, B.G., Influence of Selected White-Rot Fungi and Topdressings on the Composition of Thatch components of Four Turfgrasses, Agronomy Journal, vol. 76, (May-Jun. 1984), 359-362.

Martin, S.B., and Dale, J.L., Biodegradation of Turf Thatch With Wood-Decay Fungi, Photopathology (1980) 70:297-301.

Xu, Jie and Yang, Qian, Isolation and Characterization of Rice Straw Degrading, Streptomyces griseorubens C-5, Biodegradation (2010) 21:107-116.

Unpublished, internal progress report from inventor, Dr. Qingguo Huan to research sponsor, the Golf Course Superintendents Association of America (GCSAA) on a Novel Method to Facilitate Biodethatching Using Fungal Laccases, Oct. 31, 2008.

Unpublished, internal progress report from inventor, Dr. Qingguo Huan to research sponsor, the Golf Course Superintendents Association of America (GCSAA) on a Novel Method to Facilitate Biodethatching Using Fungal Laccases, May 16, 2009.

Ohkuma, Moriya et al., Lignin degradation and roles of white rot fungi: Study on an efficient symbiotic system in fungus-growing termites and its application to bioremediation, RIKEN Review No. 42 (Dec. 2001).

Chamberlain, K., Crawford, D.L., Thatch biodegradation and antifungal activities of two lignocellulolytic Streptomyces strains in laboratory cultures and in golf green turfgrass, Can J Microbiol 2000; 46:550-8.

Research agreement between The University of Georgia Research Foundation and The Environmental Institute for Golf, effective May 8, 2008.

* cited by examiner

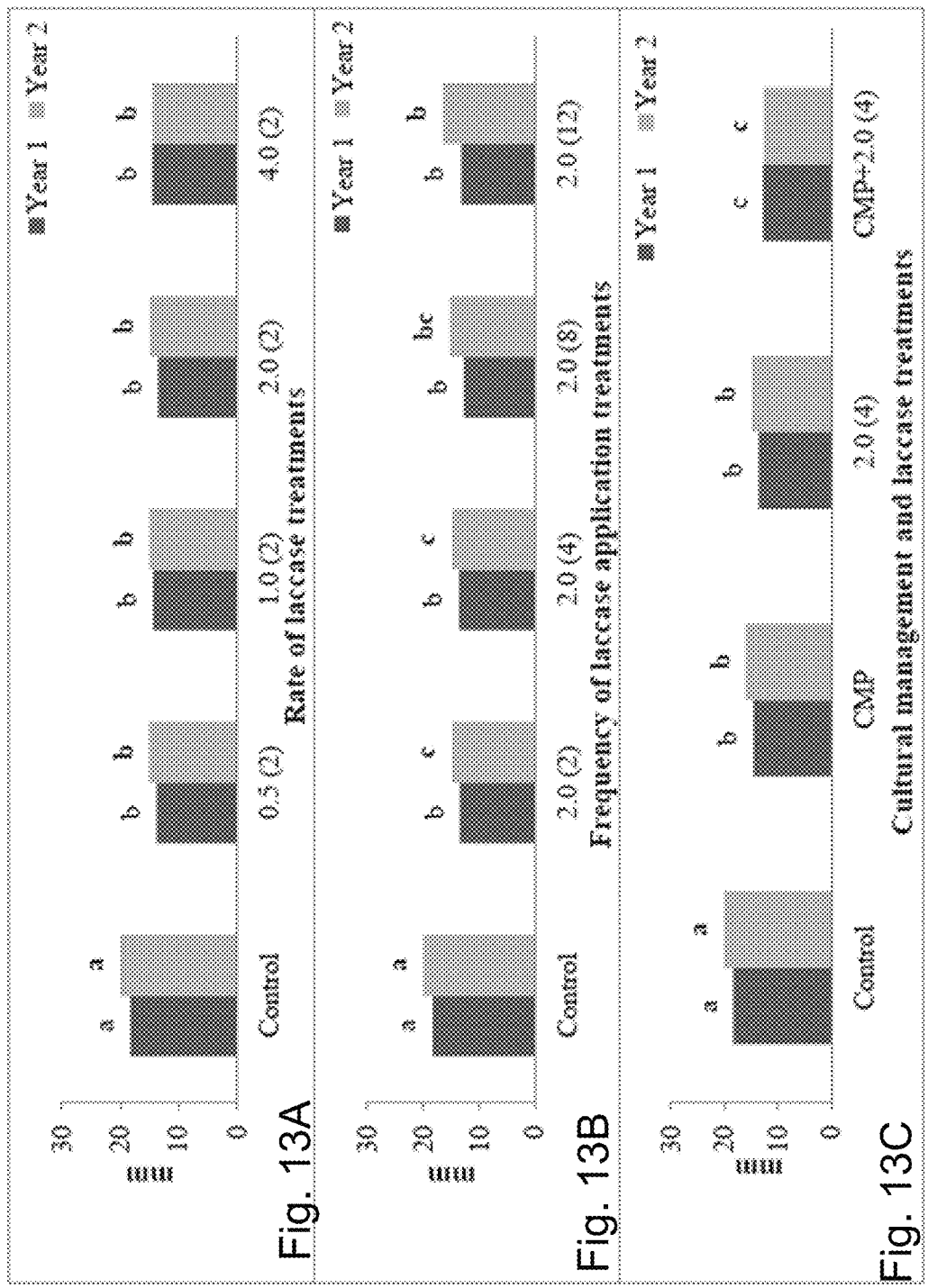

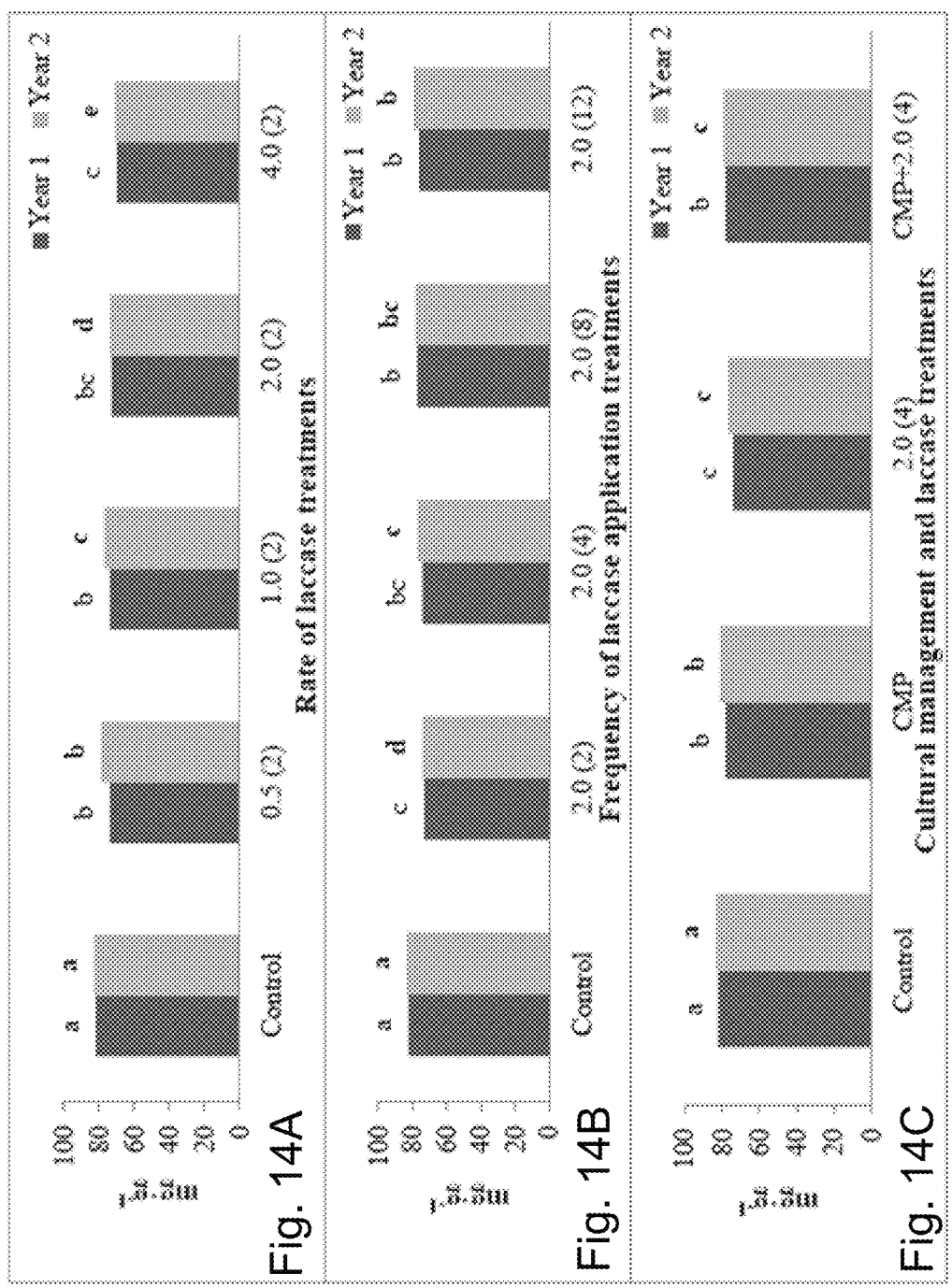

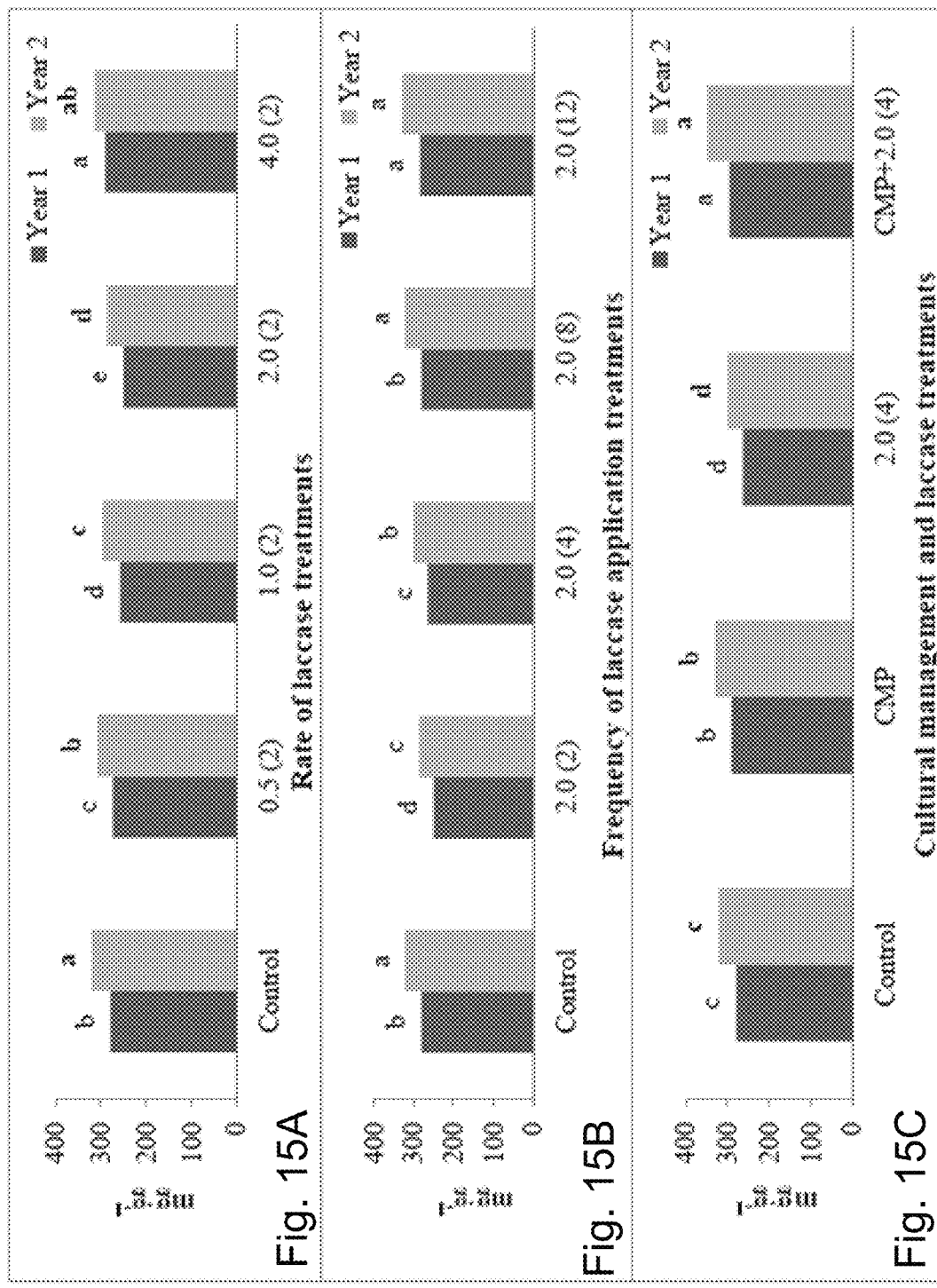

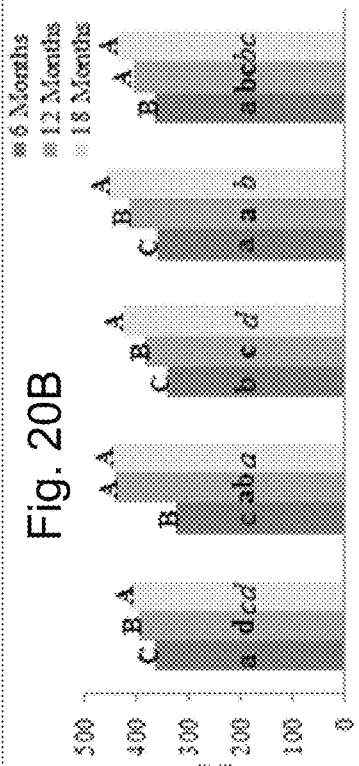
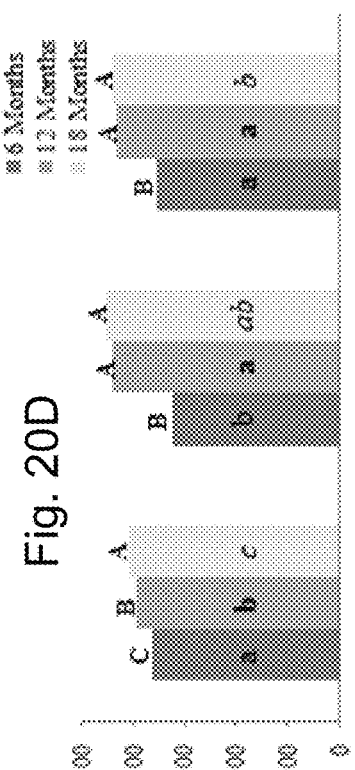
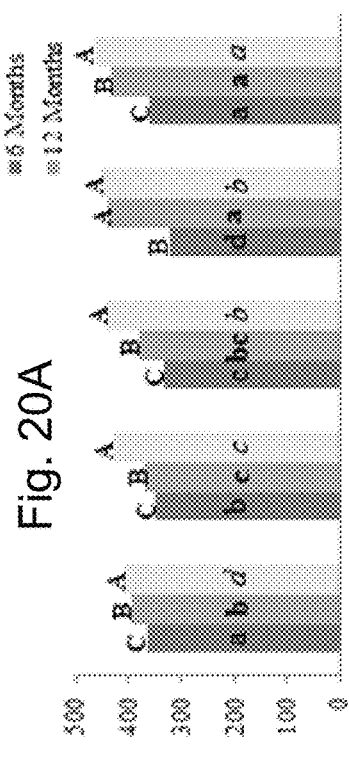
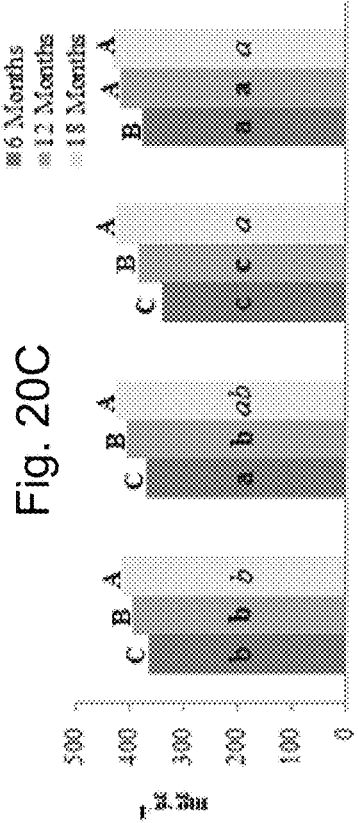
Fig. 20A
Fig. 20B
Fig. 20C
Fig. 20D

METHODS AND COMPOSITIONS USING FUNGAL LACCASES TO REDUCE TURF THATCH

CROSS-REFERENCE TO RELATED APPLICATION

This application is a Continuation-in-Part of copending U.S. patent application entitled, "Methods and Compositions using Fungal Laccases to Reduce Turf Thatch," having Ser. No. 13/249,729, filed Sep. 30, 2011 and U.S. provisional patent application of the same title having Ser. No. 61/388,160, filed Sep. 30, 2010, both of which are entirely incorporated herein by reference.

BACKGROUND

Thatch, a layer of organic matter including tightly intermingled dead and living leaves, stems, and roots, often develops between the soil surface and the green vegetation and, left untreated, can result in deterioration of the turf quality. Thatch includes stolons, rhizomes, roots, crown tissue, leaf sheaths and blades. Thatch layer intermixed with sand or soil is known as mat layer. The mat layer generally lies below the thatch layer where sand or soil is intermingled with thatch due to cultural practices like core aeration and top dressing.

High organic matter accumulation in the form of thatch or mat causes depletion of oxygen and decreased saturated hydraulic conductivity and increased water content. This makes the turf more susceptible to drought, cold, insects, diseases and other problems such as welt wilt, soft surface, black layer, limited rooting etc. Thatch control thus represents a challenge in turf management.

Management of turfgrass greens includes monitoring and control of the formation of thatch and mat layers. A cause of problems in the thatch-mat layer includes the rapid change in the nature of organic matter from the structured organic matter in live plant root tissues to the unstructured organic matter in dead plant tissues. Although live organic matter is not supposed to adversely affect soil's physical properties, the dead gelatinous organic matter in thatch swells in the presence of water during decomposition and plugs the soil macropores (air-filled pores), causing low oxygen levels in the root zones.

Extensive root death during persistent wet and hot conditions plugs the air-filled pores causing a decrease in the infiltration rate as well as oxygen stress. Increased accumulation of organic matter causes anaerobic conditions, which further slows the rate of organic matter decomposition. Grasses generally produce more adventitious roots (surface roots) during anaerobic conditions, further increasing organic matter content. Although a small amount of organic matter reduces surface hardness, moderates soil temperature extremes, increases the resilience and improves wear tolerance of turfgrass surface, excessive thatch and mat layers are undesirable in turfgrass. Unfortunately, control and management of thatch and mat layer buildup poses a challenge.

Cultural or mechanical practices like core-aeration, vertical mowing, grooming, and application of topdressing (such as sand) have been used to manage the thatch-mat buildup but have not proven sufficiently effective. These cultural practices are also intensive in terms of cost, energy, and labor, and some may cause adverse effects on turfgrass quality and site-use for a period of time.

Thatch-mat layer results due to a more rapid rate of organic matter accumulation than degradation. It is believed that the rate of thatch degradation, and most microbial degradation mechanisms, are restricted by the presence of lignin, a plant cell wall constituent that is resistant to microbial degradation. Lignin is a 3-dimensional amorphous polymer with a random and unorganized methoxylated phenyl propane structure that serves as a barrier in the cell walls to limit the accessibility to the more biodegradable plant materials, such as cellulose and hemicelluloses, by microbial degraders. Natural degradation of lignin is carried out in the environment by certain white-rot fungi which solubilize and mineralize lignin with the help of lignolytic enzymes thus exposing cellulosic materials for further bacterial degradation in the environment.

White rot fungi are recognized as one of the few active lignin degrading microorganisms found in the nature. Oxidative enzymes produced by fungi are able to attack the aromatic contents in lignin and produce free radicals, leading to degradation of lignin. White-rot fungi preferentially attack lignin over cellulose or hemicellulose in the wood tissue. This process of selective delignification exposes cellulosic materials for further bacterial degradation in the environment. Thatch is high in lignin, and, for this reason, turfgrass species high in lignin content are more resistant to decomposition.

Oxidative enzymes such as laccases, lignin peroxidases and manganese peroxidases produced by white rot fungi attack the aromatic components of lignin and contribute to its effective degradation. They have been used in the pulp and paper industry to remove lignin from wood pulp. Laccases, the multi copper oxidases, act on a wide variety of aromatic compounds by reducing oxygen to water.

SUMMARY

Briefly described, embodiments of the present disclosure provide for methods and compositions for reducing turf thatch.

Embodiments of methods of degrading turf thatch of the present disclosure include contacting the turf thatch with a composition including an isolated fungal laccase enzyme.

Embodiments of composition of the present disclosure for reducing turf thatch include formulations adapted for application to turfgrass where the formulations include an isolated fungal laccase enzyme. In embodiments, the formulation also includes water.

Embodiments of the present disclosure also include compositions for reducing turf thatch that include a particulate topdressing having isolated fungal laccase enzymes immobilized to the particles of the topdressing.

In embodiments of the methods and compositions of the present disclosure, the isolated laccase enzyme is from white rot fungi. In embodiments, the laccase enzyme is isolated from white rot fungi, such as, but not limited to *Trametes versicolor*.

Other systems, methods, features, and advantages of the present disclosure will be or become apparent to one with skill in the art upon examination of the following drawings and detailed description. It is intended that all such additional systems, methods, features, and advantages be included within this description, and be within the scope of the present disclosure.

BRIEF DESCRIPTION OF THE DRAWINGS

The disclosure can be better understood with reference to the following drawings, which are described in the description and examples below. The components in the drawings are not necessarily to scale, emphasis instead being placed upon clearly illustrating the principles of the present disclosure.

FIGS. 13A-13C are a series of bar graphs illustrating thatch layer thickness (TLT) after six months of treatment application on creeping bentgrass with: five different levels of laccase (control, 0.5, 1.0, 2.0, and 4.0 units cm$^{-2}$; FIG. 13A); laccase activity level 2.0 units cm$^{-2}$ applied at four frequencies (control, 2, 4, 8, and 12 weeks; FIG. 13B); and laccase at 2.0 units cm$^{-2}$ applied at frequency of 4 weeks in comparison with cultural management practice (control, cultural management practice (CMP), 2.0 (4), and CMP+2.0 (4); FIG. 13C). Values are means of four replicates. Same letter on top of the bars (year one=standard, year two=bolded) are not considered to be statistically different according to Fisher's protected LSD at $\alpha=0.05$.

FIGS. 14A-14C are a series of bar graphs illustrating extractive-free acid-soluble content ($L_S$) after six months of treatment application on creeping bentgrass with: five different levels of laccase (control, 0.5, 1.0, 2.0, and 4.0 units cm$^{-2}$; FIG. 14A); laccase activity level 2.0 units cm$^{-2}$ applied at four frequencies (control, 2, 4, 8, and 12 weeks; FIG. 14B); and laccase at 2.0 units cm$^{-2}$ applied at a frequency of 4 weeks in comparison with cultural management practice (control, cultural management practice (CMP), 2.0 (4), and CMP+2.0 (4); FIG. 14C). Values are means of four replicates. Same letter on top of the bars (year one=standard, year two=bolded) are not considered to be statistically different according to Fisher's protected LSD at $\alpha=0.05$.

FIGS. 15A-15C are a series of bar graphs illustrating Extractive-free acid-insoluble content ($L_I$) after six months of treatment application on creeping bentgrass with: five different levels of laccase (control, 0.5, 1.0, 2.0, and 4.0 units cm$^{-2}$; FIG. 15A); laccase activity level 2.0 units cm$^{-2}$ applied at four frequencies (control, 2, 4, 8, and 12 weeks; FIG. 15B); and laccase at 2.0 units cm$^{-2}$ applied at a frequency of 4 weeks in comparison with cultural management practice (control, cultural management practice (CMP), 2.0 (4), and CMP+2.0 (4); FIG. 15C). Values are means of four replicates. Same letter on top of the bars (year one=standard, year two=bolded) are not considered to be statistically different according to Fisher's protected LSD at $\alpha=0.05$ FIG. 16A); laccase activity level 2.0 units cm$^{-2}$ applied at four frequencies (control, 2, 4, 8, and 12 weeks; FIG. 16B); and laccase at 2.0 units cm$^{-2}$ applied at a frequency of 4 weeks in comparison with cultural management practice (control, cultural management practice (CMP), 2.0 (4) and CMP+2.0 (4); FIG. 16C). Values are means of four replicates. Same letter on top of the bars (year one=standard, year two=bolded) are not considered to be statistically different according to Fisher's protected LSD at α=0.05.

FIGS. 20A-20D illustrate extractive-free total lignin content ($L_T$) in mg·g$^{-1}$ at 6, 12, and 18 months after treatment initiation on creeping bentgrass with rate of laccase application (FIG. 2A); frequency of application of laccase (FIG. 2B); cultural management and laccase treatments (FIG. 2C); and laccase sources (FIG. 2D). Values are means of four replicates. Same letter within the bars (6 months=lowercase standard, 12 months=lowercase bold, and 18 months=lowercase italics) and same letter on top of the bars (duration effect=uppercase bolded) are not considered to be statistically different according to Fisher's protected LSD at α=0.05.

DESCRIPTION

Figure 1:
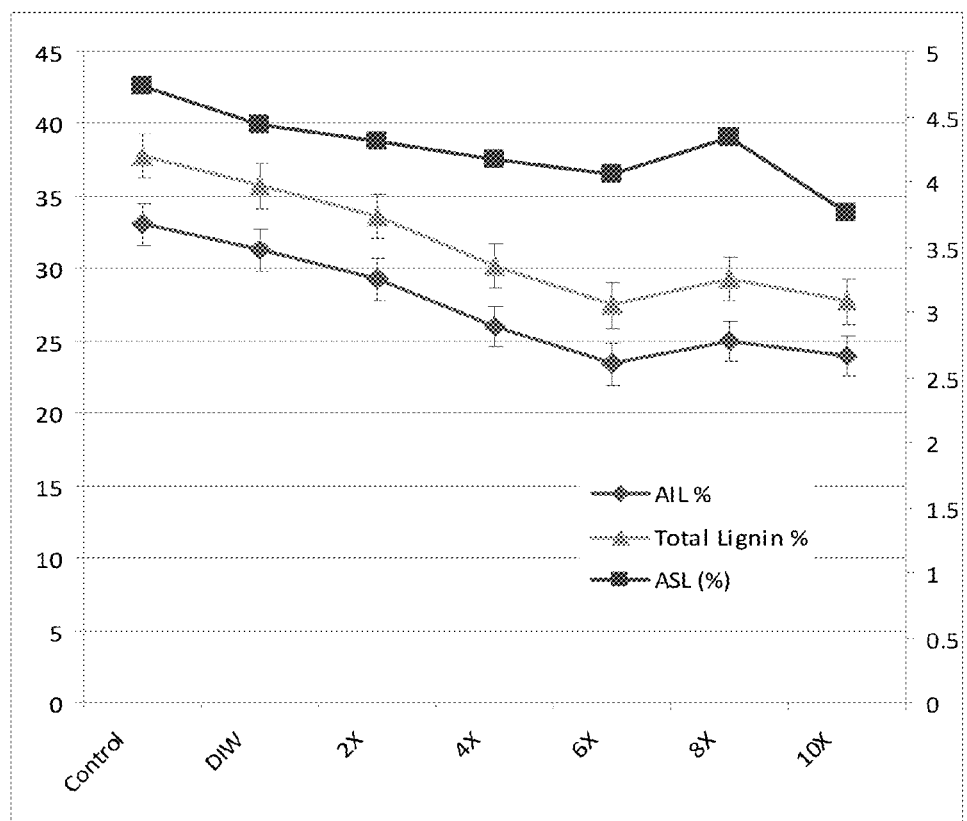
FIG. 1 is a graph illustrating lignin contents of thatch materials that have received laccase treatment at different concentrations (0, 2, 4, 6, 8, 10 units mL$^{-1}$) for seven days. Extractive-free acid-insoluble lignin (AIL %) and Total Lignin % corresponds to the Y axis on the left and extractive-free acid-soluble lignin (ASL %) to the axis on the right.

The details of some embodiments of the present disclosure are set forth in the description below. Other features, objects, and advantages of the present disclosure will be apparent to one of skill in the art upon examination of the following description, drawings, examples and claims. It is intended that all such additional systems, methods, features, and advantages be included within this description, be within the scope of the present disclosure, and be protected by the accompanying claims Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, organic chemistry, biochemistry, genetics, botany, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions:

In describing and claiming the disclosed subject matter, the following terminology will be used in accordance with the definitions set forth below.

Having defined some of the terms herein, the various embodiments of the disclosure will be described.

As used herein the term "isolated laccase" or "isolated laccase enzyme" refers to a laccase enzyme that has been separated from its biological source (e.g., white rot fungi). The isolated laccase may or may not be combined in a formulation with other ingredients for application to turfgrass, thatch sample, or other lignin-containing sample. An isolated laccase may or may not be purified (e.g., free from other environmental contaminants, microbial secretes, or deactivated organisms), but it is separated from the source organisms or the source organisms have been deactivated.

As used herein, the term "thatch" refers to a layer of organic matter including tightly intermingled dead and living plant matter (e.g., stolons, rhizomes, roots, crown tissue, leaf sheaths and blades) located generally between the soil surface and the green vegetation (e.g., green turfgrass). As used herein, "thatch" may also include the mat layer (e.g., a layer of thatch intermixed with sand and/or soil).

The term "turf or "turfgrass", as used herein, refers to any vegetative ground covering, such as, but not limited to, various species of grasses used for lawns, fields, golf course grounds, and the like.

As used herein, "degrade" or "degrading" with respect to thatch, mat, or other lignin-containing sample indicates that the laccase enzymes are able to break-down portions of the chemical structure of the lignin-containing components of the sample or otherwise act to reduce the amount (measured by weight, thickness, or other measureable variable) of thatch, mat, and/or lignin content of the sample as compared to a sample not treated with the enzyme or the same sample prior to treatment with the laccase enzyme. Furthermore, "prevention" of thatch buildup, as used herein, indicates that application of a laccase enzyme, composition, or formulation of the present disclosure to a turfgrass reduces or eliminates the amount of thatch buildup over a predetermined period of time as compared to a similar turfgrass that is not treated with the laccase enzyme, composition, or formulation of the present disclosure.

As used herein, the terms "application" and/or "treatment" with respect to laccase enzyme compositions of the present disclosure refers to the act of contacting a specimen/sample (e.g., thatch sample, turfgrass sample, lawn, field, etc.) with a laccase enzyme composition of the present disclosure.

As used herein, the term "mediator" refers to compounds that help electron transfer during enzyme catalysis and thus enhance the efficiency of the enzyme. Exemplary mediators of laccase activity include, but are not limited to, guaiacol, catechol, ABTS, violuric acid, and the like.

The term "topdressing" as used herein, refers to a material applied to the top of a turfgrass ground covering, usually in an effort to obtain a desirable effect such as improved growth, color, health, or other turfgrass quality. Some examples of topdressing include sand or other particulate material often applied to turfgrasses for various purposes, including, but not limited to, management of soil moisture content.

Description:

Embodiments of the present disclosure include methods and compositions including isolated laccase enzymes to degrade and/or reduce turf thatch and/or to prevent the accumulation of turf thatch buildup.

Formation of thatch and mat layers represents a significant problem in turf management, such as golf course greens, sports fields, and lawns. Thatch is a layer of organic matter containing both living and dead plant tissues intermingled tightly with each other that accumulates between the soil and green turfgrass. It includes stolons, rhizomes, roots, crown tissue, leaf sheaths and blades (Engel, 1954). The mat layer is generally below the thatch layer where sand or soil is intermingled with thatch due to cultural practices like core aeration and top dressing (McCarty, 2005). Thatch management on greens is a critical aspect to long-term success of golf courses. Current methods are labor intensive, costly, and disruptive to play.

An appropriate amount of organic matter reduces turf surface hardness, moderates soil temperature extremes, increases the resilience and improves wear tolerance of turfgrass surface (Beard 1973), but excessive organic matter accumulation in the form of thatch-mat causes serious problems and represents a challenging turf management issue. High organic matter content reduces movement of oxygen through the thatch or mat zone, decreases saturated hydraulic conductivity, and increases water retention (Carrow, 2003). These primary problems further lead to some secondary problems like wet wilt, soft surface, black layer, limited rooting, and extra- and intra-cellular freezing damage (Carrow, 2004; O'Brien and Hartwiger, 2003). A cause of problems in the thatch-mat layer of golf greens, particularly in hot, humid summer periods, is the rapid change in the nature of organic matter from the structured organic matter in live plant tissues to the unstructured organic matter in dead plant tissues. Although live organic matter is supposed to have no adverse effect on the soil physical properties, the dead gelatinous organic matter swells in the presence of water during decomposition and plugs the soil macropores (air-filled pores). This causes a rapid decrease in the infiltration rate and oxygen levels in the root zones (Carrow, 2004; O'Brien and Hartwiger, 2003). The low oxygen levels (anaerobic conditions) further reduce the organic matter decomposition. Grasses generally produce more adventitious roots (surface roots) during anaerobic conditions that further increase organic matter content in the surface soil layer and exacerbate the situation.

Cultural or mechanical practices like core-aeration, vertical mowing, grooming, and top dressing have been used to attempt to manage thatch-mat buildup but are not sufficiently effective. Past studies have shown contrasting results in terms of thatch-mat reduction by various cultural practices (Carrow et al., 1987; Dunn et al., 1981; McCarty et al., 2005). On the other hand, these cultural practices are intensive in terms of cost, energy, and labor and can result in adverse effects on turfgrass quality and interfere with use of the turfgrass site (Landreth et al., 2008; McCarty et al., 2007). Several non-destructive thatch control studies using glucose, cellulase solutions (Ledeboer and Skogley, 1967) and commercial inocula containing various microorganisms (Murdoch and Barr, 1976; McCarty et al., 2005) were ineffective in reducing the amount of thatch.

Thatch-mat layers can result from a more rapid rate of organic matter accumulation than degradation (Beard, 1973). As such, studies have been carried out to enhance biodegradation of organic matter. This is usually done by inoculating microbial strains and supplementing nutrients. Past studies, however, have indicated that the results of biodethatching are highly variable from case to case (Ledeboer and Skogley, 1967; McCarty et al., 2005). Although reduction in cellulose content and total oxidizable organic matter of bermudagrass and centipedegrass (Sartain and Volk, 1984) and weight loss of bermudagrass pellets were observed when St. Augustine grass and zoysiagrass stolons (Martin and Dale, 1980) were inoculated with different wood-decaying fungi under controlled greenhouse and laboratory conditions, field inoculation experiments on bermudagrass showed no thatch degradation (Martin and Dale, 1980).

These approaches have very limited utility in decreasing thatch because microorganisms are highly dependent on environmental conditions, making it difficult to maintain a stable population of specific organisms on a golf course green. For instance, microbial degraders, as living organisms, are highly dependent on natural conditions such as pH, moisture, aeration, redox, nutrients, competing organisms and pesticide use. Additionally, many of the microbes used are only capable of degrading cellulose and hemicelluloses and are restricted by the presence of lignin, a plant cell wall constituent. The presence of lignin in plant cell walls limits the accessibility of microorganisms to the more biodegradable plant materials (cellulose and hemicelluloses).

Lignin is a 3-dimensional amorphous polymer including a random and unorganized structure that serves as a barrier in plant cell walls to limit the accessibility to the more biodegradable plant materials, such as cellulose and hemicelluloses, by microbial degraders (Ledeboer and Skogley, 1967). Lignin is formed in plants by oxidative coupling of mono lignols of three primary hydroxycinnamyl alcohols: p-coumaryl, coniferyl and sinapyl alcohols. The corresponding lignin monomers are known as p-hydroxy phenyl, guaiacyl and syringyl units, respectively (Wong, 2009). Lignification is achieved by cross linking of monomers with a growing polymer via polymer-polymer coupling. Based on the random coupling theory, several models of lignin molecular structure have been proposed but these models do not imply any particular sequence of monomeric units in the lignin macromolecule (Davin and Lewis, 2003; Chen and Sarkanen, 2003).

Natural degradation of lignin is carried out in the environment by organisms such as, but not limited to, white-rot fungi, which excrete extracellular lignolytic enzymes that solubilize and mineralize lignin (Kirk et al., 1975). Such enzymes preferentially attack lignin rather than cellulose or hemicellulose in the wood tissue (Mester et al., 2004; Blanchette, 1984). This process of selective delignification exposes cellulosic materials for further bacterial degradation in the environment (Otjen and Blanchette, 1987). Thatch is high in lignin, and for this reason, turfgrass species high in lignin content are resistant to decomposition (Ledeboer and Skogley, 1967; Beard, 1973).

The present disclosure describes the use of isolated lignin-degrading enzymes, such as fungal laccases, that directly attack lignin, thereby helping to effectively reduce the thatch layer buildup in turf greens. This enzymatic dethatching is more effective and reliable than previous cultural or mechanical practices and the use of living microbes (e.g., bacteria or live fungi) for various reasons. For one, enzymes, unlike living organisms, are relatively less sensitive to environmental conditions, and the use of pesticides, while damaging to specific living organisms, does not affect the isolated enzymes. Furthermore, the enzymes cause much less, if any, physical damage to turf than many mechanical methods such as vertical mowing and core-aeration. Additionally, even if mechanical and cultural practices, such as core-aeration, vertical mowing, or application of topdressing are used, the combination of such practices with the application of the enzyme compositions of the present disclosure will produce improved results over the use of the other practices alone. Laccase-facilitated dethatching can provide an effective and non-disruptive strategy for managing thatch on turfgrass, such as on lawns, sports fields, and golf greens.

In an embodiment of a method of degrading, reducing, and/or preventing turf thatch according to the present disclosure, a composition comprising an isolated fungal laccase enzyme is applied to turf thatch. The application of the laccase enzyme helps to degrade lignin in turf thatch and thereby reduce and/or prevent the buildup of excessive thatch that causes many problems for various turfgrasses. In an embodiment, the isolated fungal laccase enzyme is from white rot fungi. In an embodiment, the isolated fungal laccase enzyme is from the white rot species *Trametes versicolor* (e.g., laccase available from Sigma-Aldrich). In another embodiment the isolated laccase enzyme is a laccase enzyme from a species of white rot fungi from the *Pycnoporus* genus. In embodiments, the laccase enzyme is obtained from Wuxi AccoBio Biotech, Inc. (Wuxi, China). In other embodiments, the isolated laccase enzyme is the partially purified isolated laccase enzyme produced by fungal fermentation and membrane purification (provided by Dr. Xiangru Liao, of Jiangnan University, China), which is isolated from an unknown fungal species from the *Pycnoporus* genus. Other possible sources of laccase enzyme include, but are not limited to, other natural sources of laccase enzyme as well as another cell or organism, such as, for example, *e.coli*, that is adapted to produce laccase, e.g., genetically engineered by transformation with a construct containing a gene for laccase.

In embodiments of the present disclosure, the enzyme compositions may contain a mediator. Such mediators may improve the efficiency of the enzyme. Mediators are compounds used by the enzyme in reactions to break down lignin and/or other thatch materials. Any mediators of fungal laccase may be included to aid reactions catalyzed by the laccase leading to degradation of turf thatch. Some mediators may include, but are not limited to, catechol, guaiacol, ABTS, violuric acid, and 1-Hydroxy-benzotriazole (HBT).

In some embodiments of the present disclosure the isolated laccase enzyme is added to irrigation water such that the amount of enzyme applied to the turf thatch is about 0.206, or 2.06 units/cm$^2$ of turf area. In embodiments, the amount of enzyme applied is at least about 0.206 units/cm$^2$ of turf area. In embodiments the amount of enzyme applied is from about 0.1 to about 20.6 units/cm$^2$, though this is not an upper limit, and higher rates could be used in some applications since no phytotoxicity has been observed. In embodiments, the composition is applied such that the amount is from 0.5 to 10 units/cm$^2$. In embodiments, the composition is applied such the amount of enzyme is about 2.0 units/cm$^2$ or more. In some embodiments, the composition containing the enzyme is applied to turf thatch such that the amount of enzyme is about 2.0 to about 4.0 units/cm$^2$.

The enzyme may be applied in various formulations, including, but not limited to, a dry powder, a solution (e.g., a crude fermentation solution containing the enzymes), a solution of isolated enzyme diluted with water, or a composition where the enzyme is immobilized to a particulate material, as discussed below, and the like.

In embodiments of a method of the present disclosure for degrading turf thatch, the composition including isolated fungal laccase is applied to turf thatch at intervals as often as about once a week or as little as once a year. In general, timing of applications can vary from about once every 2 weeks to about once every 6 months, but it is still within the scope of the present disclosure for applications more or less frequent. In embodiments, applications may be performed in intervals as seldom as one application about every 56 weeks to as often as an application about once a week. In some embodiments, the isolated fungal laccase enzyme is applied in intervals of about every 2 weeks to about every 12 weeks, including intervening intervals (e.g., every 3 weeks, every 4, weeks, every 6 weeks, and the like). The application of the compositions of the present disclosure may be applied in set intervals for duration of time, such as, but not limited to, a duration of 6 months, 1 year, 2 years, and so on. As described in Example 6 below, the enzyme composition has a residual effect on the turf grass, such that at the cessation of a treatment period, the thatch reduction/prevention effects of the laccase composition will continue for a period of time before waning. Thus, in embodiments, the composition may be applied in alternating cycles of treatment periods, such as 6 months on/6 months off, in alternating, years, etc. For instance, in an embodiment, the composition of laccase enzyme of the present disclosure may be applied to a turf grass area in designated intervals (e.g., weekly, biweekly, monthly, etc.) during the growing season (e.g., Spring/summer), after which treatment would cease for the dormant season, and resume again at the start of the next growing season. Also, it is possible that a maintenance application could be applied a designated number of times in between application periods. In practice, the timing of applications may be adjusted as determined by one of skill in the art.

Frequency and timing of applications of compositions of the present disclosure may depend on the type of grass being treated, the environment (e.g., golf course, residential yard, commercial property, etc.), as well as the climate of the area. In some embodiments, the methods of the present disclosure may include applying the composition including isolated fungal laccase to an area of turf thatch on a seasonal basis, on alternating weeks, alternating months, alternating years, or some other timing. In an embodiment regular application of the composition including isolated fungal laccase may be conducted and continued for a specified amount of time (e.g., weekly application for 6 months) and then discontinued for a specified amount of time, during which the application provides a residual effect. The application may be initiated again when the residual effect wears off or begins to decline. The application schedule may, in embodiments, include frequent application at first to induce more rapid degradation of thatch, followed by less frequent maintenance applications. Such application schedules will be determined by those of skill in the art based on grass type, quality, and condition; environmental conditions; history of the turf grass area; and the like.

The present disclosure also includes compositions for reducing turf thatch. In embodiments, the compositions include isolated laccase enzymes. In embodiments, the isolated fungal laccase enzyme is from white rot fungi. The laccase enzyme may be obtained from sources such as, but not limited to, those discussed above.

In embodiments, compositions of the present disclosure include isolated laccase enzyme that can be applied to turfgrass. In some embodiments, isolated laccase enzyme is included in a formulation already adapted for direct application to turfgrass (such as a lawn). In such embodiments, the formulation may include water, and/or other carriers, stabilizers, diluents and/or other ingredients, such as, but not limited to, those that enhance degradation of organic matter or those that serve other purposes for enhancing turfgrass quality (e.g., fertilizers, weed killers, and the like). Other embodiments include a formulation including isolated laccase enzyme that is formulated so that it can be diluted with water or other ingredients before or during application. In embodiments, the composition may be a liquid formulation with the laccase enzyme diluted with water or other liquid carrier for application via a sprayer or other liquid application device. In embodiments the formulation includes laccase in an amount such that, when the composition is applied to an area of turfgrass, the amount of enzyme is from about 0.1 to about 20.6 units/cm$^2$, about 0.206 to about 20.6 units/cm$^2$, about 2.0 to about 4.0 units/cm$^2$, and the like, as discussed above. In embodiments, a formulation of the present disclosure includes a concentration of about 50 to 2000 units/mL isolated laccase enzyme; in other embodiments, a formulation has a concentration of about 100 to 2000 units/mL isolated laccase enzyme.

In embodiments, the laccase enzyme or formulation could be included as a component in combination with other lawn care products (example weed and feed products contain herbicide impregnated fertilizer. In other embodiments, the laccase enzyme may be provided in a dry powder formulation or in formulations in which the laccase enzymes are encapsulated, immobilized to carriers, or modified with stabilizers and dispersants for application to the lawn.

In yet other embodiments, compositions of the present disclosure include a particulate topdressing, where the laccase enzyme is immobilized to particles of the particulate topdressing. The particulate topdressing may include various topdressings used for application to turfgrass, such as, for instance, sand, synthetic granules, diatomaceous earth, calcined clay, ground corn cobs or other organic materials, silica/quartz sand, zeolite, lassinite, resins, and the like.

In an embodiment, the particulate topdressing is sand and the isolated fungal laccases are immobilized to sand particles. In embodiments, laccase enzymes are immobilized to particles of topdressing (e.g., sand, or other natural or synthetic particulate material) by activating the sand or other particulate topdressing with a linking material, such as but not limited to, chitosan and/or glutaraldehyde to activate the particle surface for enzyme attachment. Next, the enzymes are immobilized to the particles via the chitosan and/or glutaraldehyde. In an example embodiment (described in greater detail in Example 5, below), the surfaces of the particles are first activated with polyethyleneimine followed by crosslinkage with glutaraldehyde to graft aldehyde groups onto the surface of the particle. Then enzymes can be covalently bonded to the particles by reaction between the aldehyde groups and free amino groups on protein surface.

In other embodiments, a layer-by-layer (LbL) assembly approach can be used to immobilize the enzymes on the particle surface. This embodiment involves alternate sorption of a polycation substrate, a polyanion substrate, and the enzyme onto the particles. For application of each layer pH is controlled to provide the substrates and/or the enzyme with the appropriate charges. Each sorption step leads to a reversal of the terminal surface charge after adsorption of a new layer. In embodiments the particles are coated with alternating layers of a polycation, a polyanion, and the enzyme, such that the enzyme is captured between layers on the particle. One example of a conventional LbL method is described in Example 5 below where poly(allylamine hydrochloride) (PAH) and poly(sodium 4-styrenesulfonate) (PSS) are used as the polyanions and polycations, respectively. The pH of the enzyme solution is carefully adjusted to several units away from their respective isoelectric points to maintain a net negative or positive charge. Sequential polyelectrolyte/enzyme layers are deposited to form repetitive particle-PAH-PSS-enzyme or particle-PAH-PSS-PAH-enzyme sandwich. For each assembly step, the polyelectrolyte/enzyme is allowed to equilibrate with the sand particles before the next layer is added.

In other embodiments, laccase enzymes can be immobilized to the particles of topdressing by methods known to those in the art for immobilizing proteins to solid surfaces. In embodiments where isolated laccase enzymes are immobilized to a topdressing formulation, frequency of application may be reduced (e.g., to as little as about once every 12 months or even less, depending on the location, application, etc.).

Now having described the embodiments of the present disclosure, in general, the Examples, below, describe some additional embodiments of the present disclosure. While embodiments of the present disclosure are described in connection with the Examples and the corresponding text and figures, there is no intent to limit embodiments of the present disclosure to these descriptions. On the contrary, the intent is to cover all alternatives, modifications, and equivalents included within the spirit and scope of embodiments of the present disclosure. Without further elaboration, it is believed that one skilled in the art can, based on the description herein, utilize the present disclosure to its fullest extent.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

EXAMPLES

Example 1

Laboratory Study

Thatch was collected from bentgrass pots in a greenhouse at Griffin, Ga. Thatch was cut into five by five cm squares and air dried. Dried thatch was ground with a coffee grinder and was passed through a 20-mesh sieve at the top and 80-mesh sieve at the bottom. The sieves were shaken for 15 minutes. The material left on the top of 20-mesh was reprocessed and material below 80-mesh was discarded. The material retained on 80-mesh was retained and used for analysis.

A 300 mg portion of thatch was weighed in each of 18 Petri plates. Ten ml of six different concentrations of laccase 0 (control), 2, 4, 6, 8 and 10 units/ml was added to Petri plates everyday as triplicates for seven days. One unit activity of laccase equals the amount of enzyme that causes the absorbance change in 468 nm at a rate of 1.0 unit/min in 3.4 ml of I mM 2,6-dimethoxyphenol in citrate-phosphate buffer at pH3.8 (Park et al., 1999). For this and the other examples, the laccase enzyme is produced by Sigma-Aldrich (Sigma Aldrich Inc., St. Louis, Mo.) and is from the white rot fungi *Trametes versicolor*.

Extractive-free ASL and AIL content in the thatch sample was determined in a two-step hydrolysis procedure according to the laboratory analytical procedure developed by The National Renewable Energy Laboratory (NREL, 2008). In the first step, extractive free thatch samples were hydrolyzed for 60 min with 72% $H_2SO_4$ at 30° C. In the second step, $H_2SO_4$ was diluted to 4% and the samples were autoclaved at 121° C. for 1 h. Acid-soluble lignin was determined using this hydrolysis liquid at 240 nm wavelength in a UV/VIS spectrophotometer. The solids remaining after acid hydrolysis were dried in an oven at 100±5° C. for 24 h, weighed, ashed in a muffle furnace at 600±25° C. for 24 h, and weighed again. Weight difference was used to calculate the acid-insoluble lignin content.

Results:

There was a significant decrease in the acid-soluble lignin content with increasing levels of laccase activity. There was a 20.5 percent decrease in acid soluble lignin in thatch sample treated with 10 units/ml of enzyme as compared with the control. Acid-insoluble lignin and total lignin content decreased significantly with increasing levels of enzyme activity up to 6 units/ml activity of laccase. Acid-insoluble lignin and total lignin content decreased by 18.5 and 26.6 percent, respectively as compared to control. The results, shown in FIG. 1, clearly indicate that the lignin content was reduced as a result of laccase treatment, and the reduction appeared to increase as the enzyme level increased.

Example 2

Greenhouse Study

Formation of high organic content in the form of thatch and/or mat layer is a major problem in management of turfgrass golf greens. A greenhouse experiment was conducted on potted bentgrass to determine the efficacy of a ligninolytic enzyme, laccase, in effectively reducing organic matter in thatch-mat layer. Laccase was added biweekly at activity levels of 0, 0.206, 2.06 and 20.6 units $cm^{-2}$ area with and without guaiacol, a mediator of laccase believed to enhance enzyme performance, and sampling was performed after two and nine months of treatment. The parameters investigated include thickness of organic layer, thatch layer, mat layer, total organic carbon at different depths, saturated hydraulic conductivity, and lignin content. After two months, a significant reduction of 8.7 and 8.4% for organic layer thickness and extractive-free total lignin content, respectively, were observed with laccase activity level of 20.6 units $cm^{-2}$ area in comparison to control. After nine months, a 15.6, and 45.0 decrease in organic and thatch layer thickness was observed, respectively, at laccase activity level of 2.06 units $cm^{-2}$ area. At the same laccase activity level with guaiacol application, a reduction of 32.1 and 6.4% and an increase of 322 % were observed for total organic carbon (0-2.5 cm depth), total lignin content, and saturated hydraulic conductivity, respectively. The 0.206 units $cm^{-2}$ area activity level of laccase did not appear to demonstrate significant effect after nine months of application. Applications did not negatively affect turf quality. The positive response of laccase at the activity level of 2.06 units $cm^{-2}$ area suggest that this could be a non-disruptive option for thatch and/or mat control in bentgrass.

Introduction

Due to higher lignin content in thatch layer, in comparison to the live grass tissues, thatch layer in turfgrass species high in lignin content is more resistant to microbial decomposition (Ledeboer and Skogley, 1967; Beard, 1973). The present example demonstrates that the use of isolated lignin-degrading enzymes such as fungal laccases can effectively reduce the thatch layer buildup in turf greens. The study confirms two hypotheses: 1) degradation of soil organic matter can be enhanced by laccase application; and 2) application of laccase enzyme has no adverse effect on turf quality.

Materials and Methods

A greenhouse experiment was conducted using "Crenshaw" creeping bentgrass, *Agrostis stolonifera*, established in pots (top diameter 15 cm, height 11.5 cm) at the University of Georgia, Griffin campus from October 2008 to July 2009. The bentgrass was acquired from East Lake Country Club, Atlanta, Ga. and was grown on 85:15 sand and organic matter mix. All the pots were irrigated daily, fertilized monthly as a 50 mL solution of 0.4%(w/v) macron water soluble 28-7-14 fertilizer (Lesco. Strongsville, Ohio), and maintained at a height of 2.5 cm. The refrigerated air conditioned greenhouse was maintained at 25±2/18±2° C., day/night temperature. For the first two months, the treatments were five replications of eight factorial combinations of four levels of laccase and two levels of guaiacol. Four laccase activity levels were 0 (control), 0.206, 2.06 and 20.6 units $cm^{-2}$ area. The treatments after the two month sampling were six factorial combinations of four replications of three levels of laccase and two levels of guaiacol. Three levels of laccase activity were 0, 0.206 and 2.06 units $cm^{-2}$ area. Each treatment was further divided into two groups, one group that received 10-mL of 0.1 M guaiacol along with enzyme treatments and one group that did not. Guaiacol is a natural co-substrate as well as mediator of laccase which is believed to enhance enzyme performance (Roper et al., 2000). Laccase was sprayed as a 40-mL solution of different activity levels, and control was sprayed by 40-mL distilled water on bentgrass.

Laccase Activity Assay

Laccase enzyme from *Trametes versicolor*, a white-rot fungus, was purchased from Sigma-Aldrich (Sigma Aldrich Inc., St. Louis, Mo.). The activity of laccase was quantified using a UV/VIS-spectrophotometer by a colorimetric assay. One activity unit of laccase corresponds to the amount of enzyme that causes the absorbance change in 468 nm at a rate of 1.0 unit $min^{-1}$ in 3.4 mL of I mM 2,6-dimethoxyphenol in citrate-phosphate buffer at pH 3.8 (Park et al., 1999). Laccase activity levels of 0 (control), 0.206, 2.06 and 20.6 units $cm^{-2}$ area actually corresponds to activity levels of 0, 0.912, 9.12 and 91.2 units $mL^{-1}$ laccase solutions, respectively. The activity level of laccase per unit area is calculated by dividing total number of units in the laccase solution by the surface area of the pot.

Measurements

The variables measured after two and nine months of treatment are listed, respectively, followed by brief description of the methods for the measurements.

Measured Variables Common to Both Sampling Durations

Effectiveness of treatments was determined by measuring organic layer thickness (OLT), total organic carbon content (TOC) for a depth of 0-5.0 cm, extractive-free acid-soluble (ASL) and -insoluble lignin (AIL) content after two and nine months of treatment application. Total lignin (TL) was obtained by addition of acid-soluble and -insoluble lignin content.

Additional Variables Measured after Nine Months of Treatment Application

After nine months of treatment application, OLT was subdivided into thatch layer thickness (TLT) and mat layer thickness (MLT), TOC was subdivided for 0-2.5, and 2.5-5.0 cm depth to better reflect the effectiveness of laccase on thatch-mat layer reduction. Saturated hydraulic conductivity (SHC) was also measured.

Turf Quality

Turf quality was determined bi-weekly for first three months and the last two months to observe any phytotoxicity due to laccase application.

Organic Layer Thickness and Thatch-Mat Layer Thickness

The thickness (OLT, TLT, and MLT) was measured from seven different locations around the edges on each pot and then averaged. The thatch layer was observed above the mat layer.

Total Organic Carbon Content

The measurement of TOC was done as described by Carrow et al. (1987), incorporated herein by reference. Soil cores were dried in an oven at 100±5° C. for 48 h and weighed. Soil cores were ashed in a muffle furnace at 600±25° C. for 24 h and weighed again. Total organic carbon content was determined as the difference in the two readings and percent total organic carbon was calculated for statistical analysis.

Saturated Hydraulic Conductivity

Intact cores were obtained from the center of each pot using a soil corer. The cores were obtained in brass rings. The bottom of the core was covered with a double layer of cheesecloth held in place with a rubber band. The core was saturated overnight in a 0.05 N $CaCl_2$ solution. A clear plastic cylinder of the same diameter as of the brass ring was fastened above the brass ring with paraffin wax tape. The SHC of the cores was measured by a constant hydraulic head method using a Marriott tube apparatus. A time of 10-minutes was allowed for the establishment of steady state flow through the samples. Volume of water that passed through the core was measured for one minute and repeated three times. Saturated hydraulic conductivity was calculated using Darcy's equation.

Extractive-Free Lignin Content

Thatch was collected from each pot from the top 2.5 cm after sampling for TOC and SHC. Extractive-free ASL and AIL content in the thatch layer was determined in a two-step hydrolysis procedure according to the laboratory analytical procedure developed by The National Renewable Energy Laboratory (NREL, 2008), which is hereby incorporated by reference herein. In the first step, extractive free thatch samples were hydrolyzed for 60 min with 72% $H_2SO_4$ at 30° C. In the second step, $H_2SO_4$ was diluted to 4% and the samples were autoclaved at 121° C. for 1 h. Acid-soluble lignin was determined using this hydrolysis liquid at 240 nm wavelength in a UV/VIS spectrophotometer. The solids remaining after acid hydrolysis were dried in an oven at 100±5° C. for 24 h, weighed, ashed in a muffle furnace at 600±25° C. for 24 h, and weighed again. Weight difference was used to calculate the acid-insoluble lignin content.

Turf Quality

The potential for phytotoxicity of each treatment was recorded every two weeks by rating turf quality and canopy spectral reflectance. Visual turf quality ratings were rated on the basis of color, shoot density, and uniformity. Turf quality was rated on a numerical score where 1 equals no live turf and 9 equals ideal dark green, uniform turf (Johnson et al., 1987, which is hereby incorporated by reference herein). Grass index was determined using TCM 500 turf color meter (Spectrum Technologies, Plainfield, Ill.). Grass index is a numerical score of the color and density of grass based on the spectral reflectance at 660 and 850 nm. Three grass index readings were recorded from each pot and averaged for statistical analysis.

Statistical Analysis

A completely randomized factorial design was used to analyze the full model, a three factor study consisting of two levels of treatment duration, three levels of laccase, and two levels of guaiacol. Similarly, a two factor study consisting of four levels of laccase enzyme and two levels of guaiacol for the first two months and three levels of laccase enzyme and two levels of guaiacol for nine months of treatment application was analyzed. Analysis of variance (ANOVA) was performed to evaluate the main effects of treatment duration, laccase, and guaiacol and interaction effects of these three factors using general linear model (GLM) (SAS Institute, 1989). Fisher's LSD test with $\alpha=0.05$ was used for obtaining means separation Results The results are explained on the basis of the Anova table (Table 1 (FIG. 16)). The result section is divided into full model, two, and nine months of treatment application.

Full Model

The full model was used to compare the parameters at two sampling dates. The model includes the main and interaction effects of treatment duration, three levels of laccase, and two levels of guaiacol for OLT, TOC (0-5.0 cm), ASL, and AIL. Three levels of laccase were used, as laccase treatment at activity level of 20.6 units $cm^{-2}$ was discontinued after two months of application.

Figure 2:
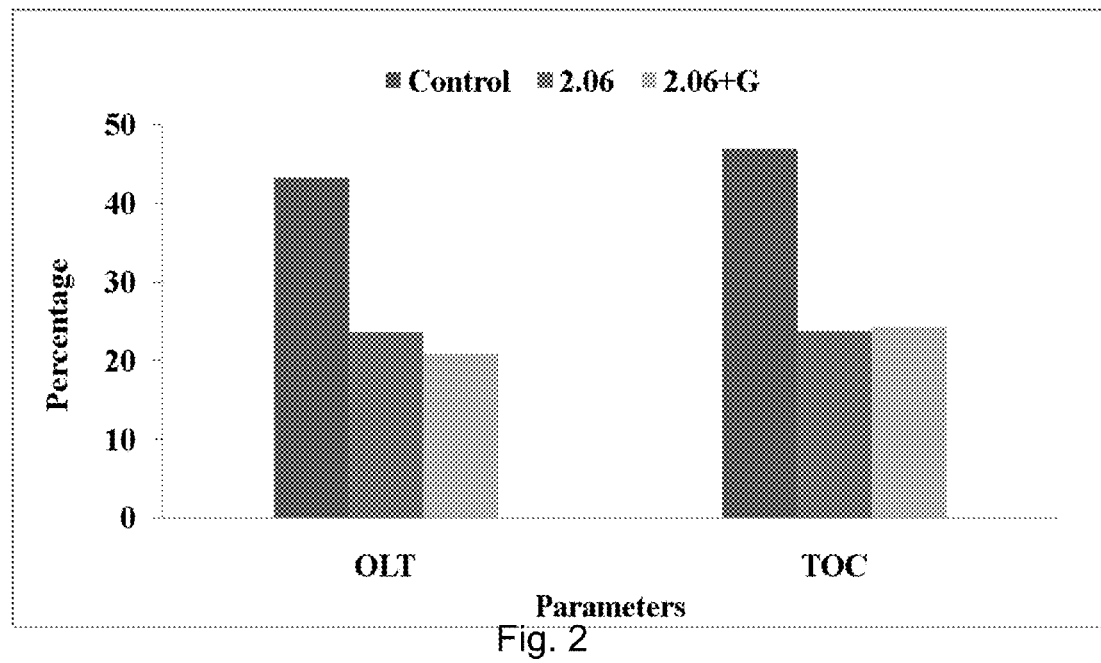
FIG. 2 is a bar graph illustrating organic layer thickness (OLT) and total organic carbon (TOC) (0-5.0 cm) percent increase within two sampling dates (2 and 9 months) in the greenhouse study on creeping bentgrass comparing control and laccase activity level of 2.06 units cm$^{-2}$ area with and without guaiacol (G).

A significant effect of treatment duration, and interaction of treatment duration and laccase treatments was observed on OLT, TOC (0-0.5 cm), and ASL (Table 1 (FIG. 16)). However, no significant effect was observed for AIL. Laccase application was found to have significant effect on OLT, TOC (0-5.0 cm), ASL and AIL at 0.1% level of significance. However, guaiacol treatment as well as interaction of guaiacol and treatment duration did not appear to have significant effect on the tested parameters. An increase of 43.2, 23.6, and 20.9% in OLT was recorded in control pots and pots treated with 2.06 units $cm^{-2}$ area laccase, without and with guaiacol, respectively, in between the two sampling dates of two and nine months after initiation (FIG. 2 and Table 2 (FIG. 17)). Overall, there was an increase of 46.9 and 23.7% in TOC (0-5.0 cm) exhibited between two sampling dates for control and laccase activity level of 2.06 units $cm^{-2}$ area, respectively (FIG. 2 and Table 2 (FIG. 17)).

Two Months

After two months of treatment application, the effect of laccase was significant at 0.1% level of significance for ASL and AIL (Table 1). There was no effect of laccase observed on OLT and TOC (0-5.0 cm). However, there was a 15.6% reduction in OLT with laccase activity level of 20.6 units $cm^{-2}$ area without guaiacol, in comparison to control (Table 2 (FIG. 17)). Other treatments showed no effect on OLT. Guaiacol and interaction effect of laccase and guaiacol had no significant effect on any of the parameters (Table 1 (FIG. 16)). A reduction of 11.9, 7.8, and 8.4% for ASL, AIL and TL content, respectively, after two months of application was observed for laccase activity of 20.6 units $cm^{-2}$ area without mediator (Table 3 (FIG. 18)). Similarly, a reduction of 9.6, 7.3, and 7.7% for ASL, AIL, and TL was found at same laccase activity level along with guaiacol. Laccase activity level of 2.06 units$^{-2}$ area with guaiacol also showed significant reduction for ASL.

Nine Months

After nine months of treatment application, a significant effect of laccase application was observed for OLT, TLT, TOC (0-5.0, and 0-2.5 cm), ASL, AIL and SHC at 0.1% level of significance (Table 1 (FIG. 16)). A significant effect of guaiacol was observed for ASL and SHC at 5 and 1% level of significance, respectively (Table 1 (FIG. 16)). Interaction effect of laccase and guaiacol was observed for SHC at 0.1% level of significance. However, no effect was observed for MLT and TOC (2.5-5.0 cm) after nine months of treatment application.

Figure 3:
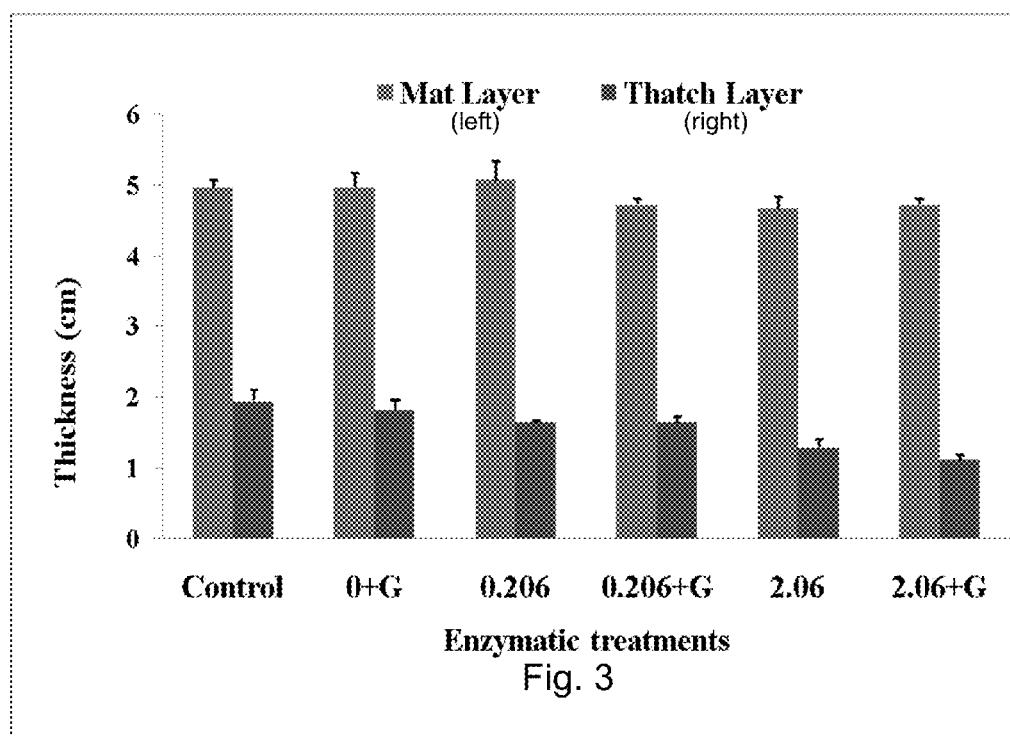
FIG. 3 is a bar graph illustrating thatch (TLT) and mat layer thickness (MLT) after nine months of treatment on creeping bentgrass in the greenhouse study with three different levels of laccase (0 (control), 0.206 and 2.06 units cm$^{-2}$ area) with and without the mediator, guaiacol (G). Values are means of four replicates, and error bars are standard errors. LSD for comparing the values within different treatments is 0.30 and 0.51 for thatch and mat layer thickness, respectively.

A decrease of 14.5 and 13.0% was observed in OLT with laccase activity level of 2.06 units $cm^{-2}$ area with and without guaiacol, respectively, in comparison to control (Table 2 (FIG. 17)). Similarly, a 45 and 35% decrease in TLT was observed with laccase activity level of 2.06 units $cm^{-2}$ area with and without guaiacol, respectively, as compared to control. The treatment with 2.06 units $cm^{-2}$ area of laccase activity was significantly different in comparison to control as well as to 0.206 units $cm^{-2}$ area of laccase activity (FIG. 3).

Figure 4:
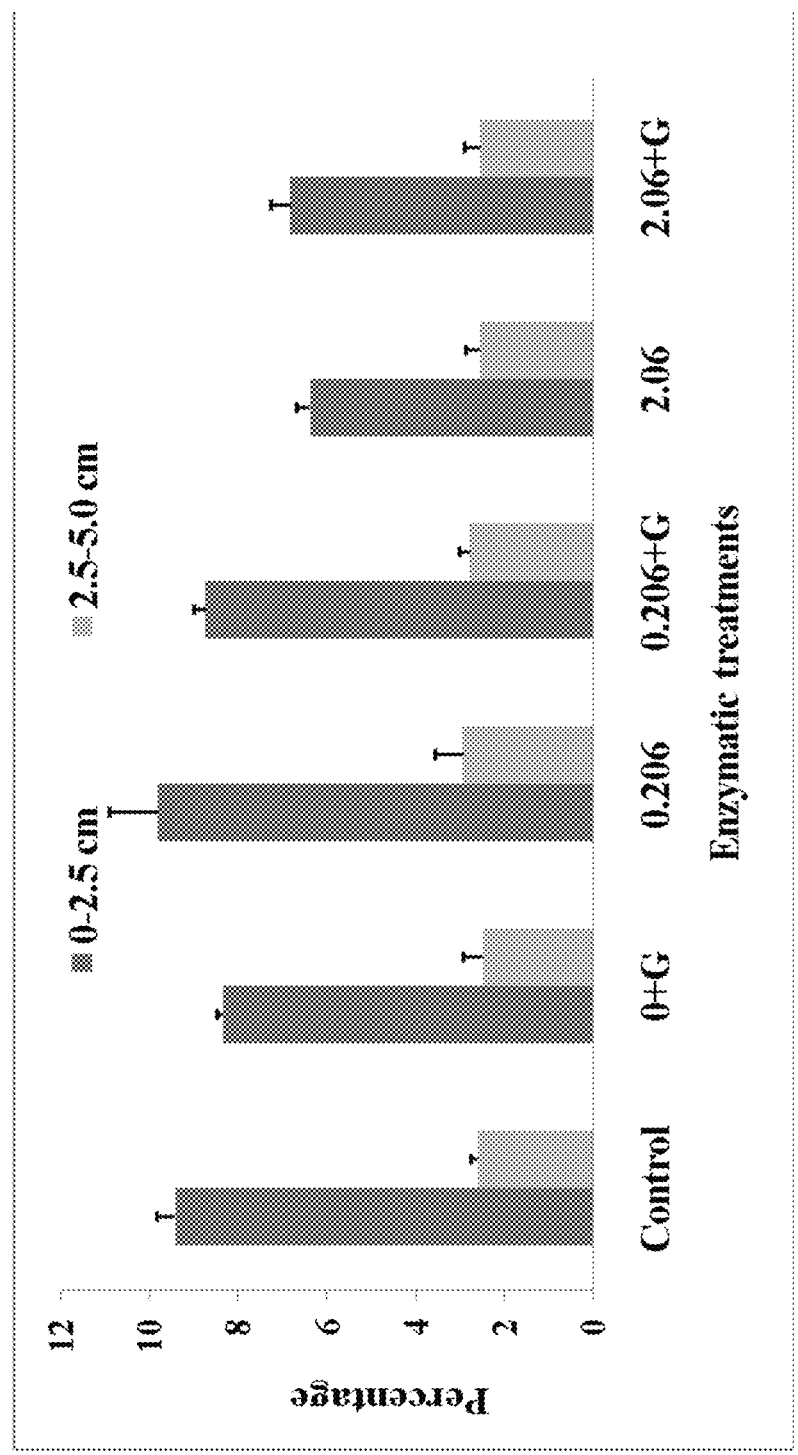
FIG. 4 is a bar graph illustrating total organic carbon (TOC) for 0-2.5 cm depth and 2.5 to 5.0 cm depth after nine months of treatment on creeping bentgrass in the greenhouse study with three different levels of laccase (0 (control), 0.206 and 2.06 units cm$^{-2}$) with and without the mediator, guaiacol (G). Values are means of four replicates, and error bars are standard errors. LSD for comparing the values within different treatments is 1.51 and 0.43 for 0-2.5 cm and 2.5-5.0 cm depth, respectively.
Figure 5:
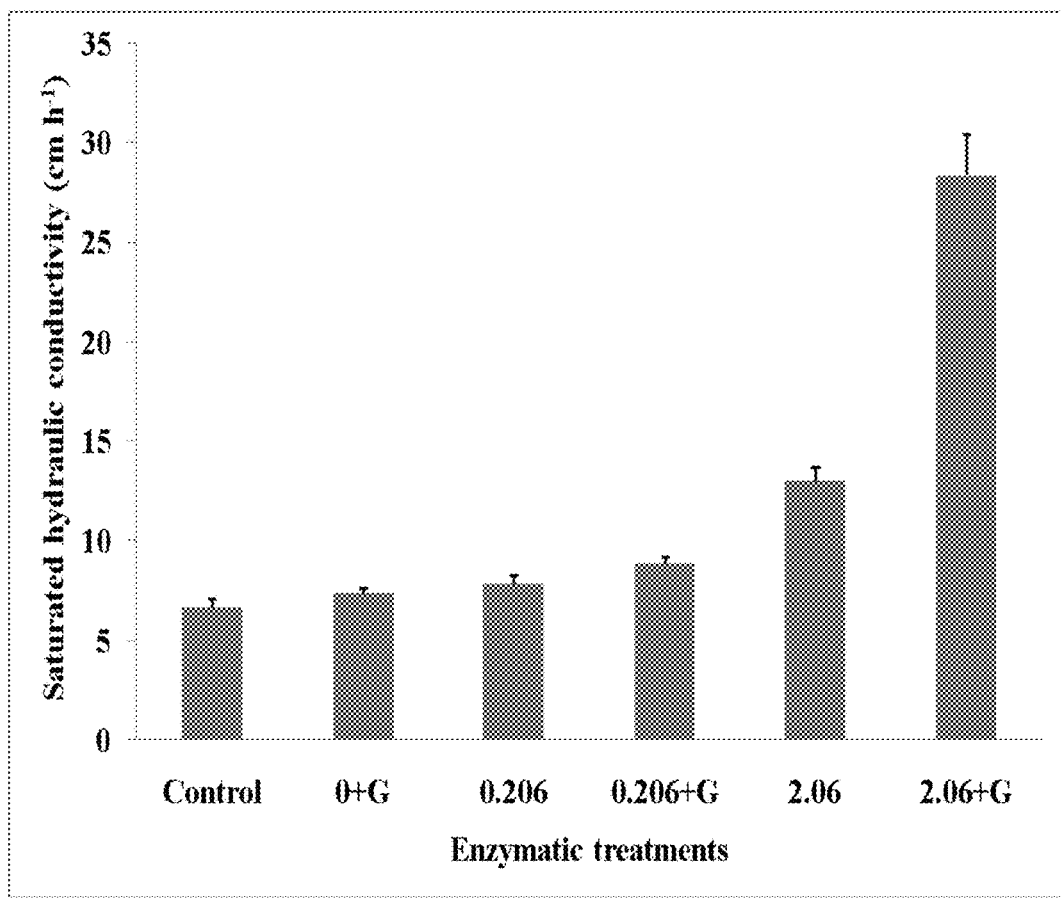
FIG. 5 is a bar graph illustrating saturated hydraulic conductivity (SHC) after nine months of treatment on creeping bentgrass in the greenhouse study with three different levels of laccase (0 (control), 0.206 and 2.06 units cm$^{-2}$) with and without the mediator, guaiacol (G). Values are means of four replicates, and error bars are standard errors. LSD for comparing the values within different treatments is 2.80.

A reduction of 15.4 and 15.8% (TOC 0-5.0 cm), 27.4 and 32.1% (TOC 0-2.5 cm) was observed at the laccase activity level of 2.06 units $cm^{-2}$ area with and without guaiacol, respectively, as compared to control (FIG. 4 and Table 2 (FIG. 17)). Similarly, an increase of 322 and 94% over the control was recorded for SHC with treatment of laccase at activity level of 2.06 units $cm^{-2}$ area with and without guaiacol, respectively (FIG. 5). A reduction of 12.2, 5.4, and 6.4% for ASL, AIL and TL content, respectively, was observed for laccase activity of 2.06 units $cm^{-2}$ area without mediator (Table 3 (FIG. 18)).

Turf Quality

No significant differences in visual quality ratings were observed for all the treatments except for the data collected after thirty eight weeks where the treatment 2.06 units $cm^{-2}$ exhibited a significant but slight reduction in turf quality in comparison to the control treatment (Table 4 (FIG. 19)). No significant differences in any treatment in comparison to control was observed when the data was analyzed as the average of data collected before (early) and after (late) the first sampling as well as the average of the whole (all) data (Table 4 (FIG. 19)). For grass index values, a decrease was observed initially after four and six weeks of treatment application at laccase activity level of 20.6 units $cm^{-2}$ area in comparison to control. However, no significant differences in grass index values were observed after six weeks of treatment application (Table 5 (FIG. 20)).

Discussion

To the best of our knowledge, this is the first study using laccase enzyme to manage thatch-mat accumulation on turf grass. Application of laccase, especially at the 2.06 units $cm^{-2}$ area activity level, proved to be effective in reducing thatch-mat depth, TOC, and significantly increasing SHC. Carley et al. (2011) noted that the nature of temporal dynamics of organic matter accumulation was for small annual changes resulting in long term effects. Our results indicate that laccase application could result in altering organic dynamics in a positive manner with the 2.06 units $cm^{-2}$ area activity level of laccase effective in reducing TLT, and TOC (0-2.5 cm). This treatment also resulted in increasing SHC after nine months of application where a three and two fold increase in SHC was observed with laccase activity level of 2.06 $cm^{-2}$ area with and without guaiacol, respectively. This increase can be explained on the basis of thatch layer thickness of the corresponding treatment. Thatch layer depth more than 1.3 cm was reported to adversely affect water infiltration (McCarty et al, 2005). Thatch layer thickness for the treatment 2.06 units $cm^{-2}$ area with and without guaiacol after nine months of treatment was 1.1 and 1.3 cm, respectively. For both two and nine months sampling, no effect of guaiacol and interaction effect of laccase and guaiacol was observed except for saturated hydraulic conductivity after nine months of application.

The lowest level of laccase application (0.206 units $cm^{-2}$ area) did not appear to have significant effect at nine months after application for the parameters tested. Laccase activity level of 20.6 unit $cm^{-2}$ area was applied for two months and was effective in significant reduction of OLT and extractive-free lignin content (ASL, AIL, and TL) of the thatch layer.

Laccase application had a minor influence on turfgrass quality. An initial but slight reduction in turf quality was observed during the first four to six weeks for grass index values at the activity level of 20.6 units $cm^{-2}$ area. However, visual quality ratings were not significantly different except for one treatment at 33 weeks.

If laccase was effective in enhancing organic matter degradation, it would seem reasonable to expect that effects would become more apparent over time. Samples were analyzed after two and nine months of treatment application. Laccase activity levels of 0.206 and 2.06 units $cm^{-2}$ area were continued for nine months. It was observed that time duration, and interaction of time duration and laccase had significant effect on OLT, TOC (0-5.0 cm) and, ASL content with laccase activity level of 2.06 units $cm^{-2}$ area. However, for the other laccase activity level, there was no apparent effect of time of application on any of the measurements.

Studies in the past using various cultural management practices with different cultivation frequencies have reported contrasting results for reduction in thatch-mat accumulation (Callahan et al., 1998; Carrow et al., 1987; Engel and Alderfer, 1967; McCarty et al., 2005; Rieke, 1994). Degradation of thatch-mat is reported either in terms of thatch-mat depth (Soper et al., 1988; Smiley et al., 1985) or in terms of thatch-mat depth and organic matter content by weight (Barton et al., 2009; McCarty et al., 2007). The organic matter content by weight in different studies is observed for different depths further making it difficult to compare the results (Barton et al., 2009; McCarty et al., 2005; Murray and Juska, 1997). In the present study, however, both organic layer thickness (thatch layer and mat layer) and total organic carbon content were observed for better comparison of effectiveness of laccase on thatch-mat degradation.

Cultural practices like core-aeration and vertical mowing are disruptive in nature and have shown to reduce the turf quality both aesthetically and physically, further reducing the playability of the turf (Barton et al., 2009; Landreth et al., 2008; McCarty et al., 2007). However application of laccase is not disruptive and the effective treatment of 2.06 units $cm^{-2}$ laccase activity for nine months of application showed no quality reduction on bentgrass.

Several non-destructive studies in the past using different chemicals like sugars, mixture of sugars and microbial inocula, and some enzyme like cellulase, proved ineffective (Ledeboer and Skogley, 1967; Murdoch and Barr, 1976; McCarty et al., 2005; Martin and Dale, 1980). Most of these studies intended to increase microbial population to degrade organic matter. But it is difficult to maintain higher microbial populations over sustained period of time under field turfgrass management systems due to the inability to maintain proper micro environment conditions required by particular microbial population. Another reason may be that previous studies were focused on degradation of cellulose and hemicellulose by using cellulase enzyme and by increasing bacterial population. Whereas, the approach of the present example is that lignin degradation will open the cell wall structure and make cellulose and hemicellulose more available for further microbial degradation. In the present example isolated laccase enzyme, which is stable over a wide pH and temperature (Baldrian, 2006; Munoz et al., 1997; Stoilova et al., 2010; Hurston, 1994), from the white-rot fungi *Trametes versicolor* was employed to act on lignin and to facilitate dethatching, thereby reducing the dependence on microbial growth and climate fluctuations.

Conclusions

The greenhouse research demonstrated that bi-weekly application of laccase enzyme at the 2.06 units cm$^{-2}$ area can be effective in reducing buildup of organic matter in highly maintained turf. Duration of laccase application appeared to have an effect on thatch-mat management as judged by results at 9 month sample period. These findings indicated a novel approach to reduce organic matter in thatch or mat and its associated problems on golf greens and represent a new non-disruptive method for thatch management.

Tables for Example 2 appear on the following pages:

TABLE 2

Organic layer thickness (OLT), total organic carbon (TOC) content (0-5.0 cm depth) for different treatments used on a creeping bentgrass after two and nine months of treatment application.

| Treatment Laccase activity units cm$^{-2}$ area | Organic layer thickness cm | | Total organic carbon (0-5.0) cm % | |
|---|---|---|---|---|
| | 2 Months | 9 Months | 2 Months | 9 Months |
| 0 (Control) | 4.84$^a$ | 6.93$^a$ | 3.37$^{ab}$ | 4.95$^a$ |
| 0 + G† | 4.74$^{ab}$ | 6.82$^{ab}$ | 3.44$^{ab}$ | 4.73$^a$ |
| 0.206 | 4.57$^{ab}$ | 6.73$^{ab}$ | 3.64$^a$ | 5.00$^a$ |
| 0.206 + G | 4.76$^{ab}$ | 6.38$^{bc}$ | 3.43$^{ab}$ | 4.94$^a$ |
| 2.06 | 4.81$^a$ | 5.98$^{cd}$ | 3.27$^b$ | 4.17$^b$ |
| 2.06 + G | 4.77$^{ab}$ | 5.85$^d$ | 3.50$^{ab}$ | 4.19$^b$ |
| 20.6 | 4.42$^b$ | — | 3.63$^a$ | — |
| 20.6 + G | 4.51$^{ab}$ | — | 3.39$^{ab}$ | — |

Values within a column bearing the same superscript are not significantly different
†G: Guaiacol, acts as a mediator

TABLE 1

Analysis of variance (ANOVA) table

| Effects | df | OLT cm | TOC (0-5.0 cm) % | ASL % | AIL % | TLT cm | MLT cm | TOC (0-2.5 cm) % | TOC (2.5-5.0 cm) % | SHC cm h$^{-1}$ |
|---|---|---|---|---|---|---|---|---|---|---|
| | | | | | Mean Square Values | | | | | |
| Full Model | | | | | | | | | | |
| Time | 1 | 36.49*** | 20.08*** | 0.5582*** | 1.026 | | | | | |
| Laccase | 2 | 0.9921*** | 1.050*** | 0.5558*** | 4.765*** | | | | | |
| Guaiacol | 1 | 0.0969 | 0.0103 | 0.0986 | 0.5073 | | | | | |
| Time*laccase | 2 | 1.092*** | 0.6082*** | 0.2295** | 0.8449 | | | | | |
| Time*guaiacol | 1 | 0.1369 | 0.0446 | 0.1960 | 0.7611 | | | | | |
| Error | 42 | 0.0771 | 0.0583 | 0.0282 | 0.3022 | | | | | |
| 2 Months | | | | | | | | | | |
| Rep | 4 | 0.0184 | 0.1694 | 0.0383* | 0.1068 | | | | | |
| Laccase | 3 | 0.2083 | 0.1671 | 0.5018*** | 7.605*** | | | | | |
| Guaiacol | 1 | 0.0070 | 0.0184 | 0.0000028 | 0.00010 | | | | | |
| Laccase*guaiacol | 3 | 0.0385 | 0.3759 | 0.0153 | 0.0302 | | | | | |
| Error | 28 | 0.08082 | 0.07609 | 0.009634 | 0.3230 | | | | | |
| 9 Months | | | | | | | | | | |
| Rep | 3 | 0.1014 | 0.04630 | 0.07850 | 1.203*** | 0.0739 | 0.0168 | 1.945 | 0.0614 | 3.239 |
| Laccase | 2 | 1.921*** | 1.4398*** | 0.6669*** | 4.301*** | 0.9602*** | 0.1653 | 16.60*** | 0.2741 | 451.9*** |
| Guaiacol | 1 | 0.2193 | 0.0440 | 0.2577* | 1.1301 | 0.0453 | 0.0652 | 1.922 | 0.0405 | 193.9*** |
| Laccase*guaiacol | 2 | 0.0355 | 0.02990 | 0.05800 | 0.3554 | 0.0135 | 0.0879 | 1.538 | 0.0104 | 140.7*** |
| Error | 15 | 0.0872 | 0.0813 | 0.0407 | 0.1319 | 0.0403 | 0.1123 | 1.0030 | 0.0827 | 3.443 |

*Significant at the 0.05 probability level;
**Significant at the 0.01 probability level;
***Significant at the 0.001 probability level

TABLE 3

Extractive-free acid-soluble (ASL), acid-insoluble (AIL), and total lignin (TL) content for different treatments used on creeping bentgrass after two and nine months of treatment application.

| Laccase activity units cm$^{-2}$ area | Treatment | | | | | |
|---|---|---|---|---|---|---|
| | Acid-soluble lignin % | | Acid-insoluble lignin % | | Total lignin % | |
| | 2 Months | 9 Months | 2 Months | 9 Months | 2 Months | 9 Months |
| 0 (Control) | 4.37$^{ab}$ | 4.22$^{b}$ | 25.99$^{a}$ | 25.74$^{b}$ | 30.35$^{ab}$ | 29.97$^{b}$ |
| 0+G† | 4.38$^{ab}$ | 4.58$^{a}$ | 26.01$^{a}$ | 26.48$^{a}$ | 30.39$^{a}$ | 31.06$^{a}$ |
| 0.206 | 4.41$^{a}$ | 4.14$^{b}$ | 25.69$^{a}$ | 25.45$^{bc}$ | 30.10$^{ab}$ | 29.59$^{b}$ |
| 0.206+G | 4.33$^{abc}$ | 4.14$^{b}$ | 25.54$^{a}$ | 25.39$^{bc}$ | 29.88$^{ab}$ | 29.55$^{b}$ |
| 2.06 | 4.27$^{bc}$ | 3.71$^{c}$ | 25.40$^{a}$ | 24.34$^{d}$ | 29.67$^{ab}$ | 28.04$^{d}$ |
| 2.06+G | 4.23$^{c}$ | 3.95$^{bc}$ | 25.39$^{a}$ | 24.96$^{c}$ | 29.62$^{b}$ | 28.90$^{c}$ |
| 20.6 | 3.85$^{d}$ | — | 23.94$^{b}$ | — | 27.79$^{c}$ | — |
| 20.6+G | 3.95$^{d}$ | — | 24.10$^{b}$ | — | 28.01$^{c}$ | — |

Values within a column bearing the same superscript are not significantly different
†G: Guaiacol, acts as a mediator

TABLE 4

Effect of different treatments on the visual quality ratings on creeping bentgrass.

| Laccase activity units cm$^{-2}$ area | Treatments Weeks | | | | | | | | | | | | |
|---|---|---|---|---|---|---|---|---|---|---|---|---|---|
| | 2 | 4 | 6 | 8 | 10 | 12 | 32 | 34 | 36 | 38 | Early | Late | All |
| 0 | 7.05$^{ab}$ | 6.74$^{a}$ | 8.32$^{ab}$ | 7.75$^{a}$ | 7.20$^{a}$ | 8.00$^{ab}$ | 7.88$^{a}$ | 7.89$^{a}$ | 8.29$^{a}$ | 8.49$^{a}$ | 7.47$^{a}$ | 7.96$^{a}$ | 7.75$^{a}$ |
| 0+G† | 7.02$^{ab}$ | 6.87$^{a}$ | 8.12$^{ab}$ | 7.73$^{a}$ | 7.14$^{a}$ | 8.07$^{a}$ | 7.77$^{a}$ | 7.74$^{a}$ | 8.06$^{a}$ | 8.39$^{a}$ | 7.44$^{a}$ | 7.86$^{a}$ | 7.55$^{a}$ |
| 0.206 | 7.19$^{a}$ | 6.75$^{a}$ | 8.16$^{ab}$ | 7.60$^{a}$ | 7.13$^{a}$ | 7.90$^{ab}$ | 8.01$^{a}$ | 8.00$^{a}$ | 8.14$^{a}$ | 8.40$^{a}$ | 7.43$^{a}$ | 7.80$^{a}$ | 7.75$^{a}$ |
| 0.206+G | 7.03$^{a}$ | 6.67$^{a}$ | 7.97$^{b}$ | 7.75$^{a}$ | 7.31$^{a}$ | 7.77$^{b}$ | 7.74$^{a}$ | 7.63$^{a}$ | 8.31$^{a}$ | 8.26$^{ab}$ | 7.36$^{a}$ | 7.84$^{a}$ | 7.46$^{a}$ |
| 2.06 | 7.19$^{a}$ | 7.04$^{a}$ | 8.31$^{ab}$ | 7.77$^{a}$ | 7.37$^{a}$ | 7.94$^{ab}$ | 7.89$^{a}$ | 7.94$^{a}$ | 8.11$^{a}$ | 8.13$^{b}$ | 7.58$^{a}$ | 7.90$^{a}$ | 7.60$^{a}$ |
| 2.06+G | 6.88$^{ab}$ | 6.73$^{a}$ | 8.39$^{ab}$ | 7.76$^{a}$ | 7.27$^{a}$ | 7.74$^{b}$ | 7.87$^{a}$ | 8.00$^{a}$ | 8.21$^{a}$ | 8.39$^{a}$ | 7.44$^{a}$ | 7.91$^{a}$ | 7.60$^{a}$ |
| 20.6 | 6.70$^{b}$ | 6.86$^{a}$ | 8.42$^{a}$ | 7.80$^{a}$ | — | — | — | — | — | — | 7.49$^{a}$ | — | — |
| 20.6+G | 6.86$^{ab}$ | 6.72$^{a}$ | 8.18$^{ab}$ | 7.90$^{a}$ | — | — | — | — | — | — | 7.46$^{a}$ | — | — |

Values within a column bearing the same superscript are not significantly different.
†G: Guaiacol, acts as a mediator Example 3

Greenhouse Study (Dead Grass)

Introduction

Another greenhouse study was started in December 2009 on dead 'Crenshaw' creeping bentgrass (*Agrostis stolonifera* L.) pots to provide more knowledge about the effects of laccase on organic matter degradation. When live grass is used, final thatch status is the net result of organic matter additions by the plant minus the degradation of organic matter. Due to the use of dead grass, the present study allowed only degradation to be observed.

Materials & Methods

Any materials and methods not described here are the same as those described in Example 2, above.

The bentgrass was acquired from East Lake Country Club, Atlanta, Ga. Pots were partially filled with 85:15 sand and organic matter mix and sod approximately 3 cm in thickness was cut to fit the pots and placed on top of the mix. All pots were established in June 2008 and grown in a controlled environment greenhouse for approximately eighteen months prior to initiation of treatments to facilitate development of thatch layer in the pots. The refrigerated air conditioned greenhouse was maintained at 25±2/18±2° C., day/night temperature maintained by a Wadsworth Step 50 controller (Wadsworth Control System, Arvada, Co) under natural lighting (approximately 85% ambient light). Pots were irrigated daily, fertilized monthly with a 50-mL solution of 0.4% (w/v) Macron water soluble 28-7-14 fertilizer (Lesco. Strongsville, Ohio), and maintained by hand clipping weekly at a height of 0.6 cm with clippings removed to develop favorable conditions for thatch development in the pots.

Prior to the treatment initiation in December 2009, the growth of creeping bentgrass in the pots was ceased by application of an herbicidal solution containing 1.3% (v/v) of Roundup Pro® (isopropylamine salt of glyphosate, Monsanto, St. Louis, Mo.) and 1.3% (v/v) Finale® Herbicide (glufosinate ammonium, Bayer Environmental Science, Montvale, N.J.). One week after herbicide application, dead creeping bentgrass was clipped down to the thatch layer. To block any natural or artificial light from reaching the pots and thereby avoid stimulation of re-growth, the pots were covered with two 76.2 μm thick sheets of black plastic sheeting cut from Husky Contractor Clean-up bags (item no HK42WCO32B, Poly America, Grand Prairie, Tex.). The treatment design was a three by two factorial with all combinations of three levels of laccase and two levels of guaiacol (2-methoxyphenol) as mediator. The three laccase activity levels were 0 (control), 2.06, and 20.6 units cm$^{-2}$ and guaiacol levels were 0 and 0.1 M solution. The experimental design was a randomized complete block with five replications and sampling times of two and six months. Forty milliliter solutions of the different laccase activity levels were applied uniformly every two weeks to each pot using a hand-held sprayer. The control was applied as 40 mL of distilled water. Guaiacol levels were applied as 10 mL of 0.1M solution. The pots were irrigated to drainage twice a week and maintained near field capacity to favor microbial activity during the six month study. Laccase treatments were applied at least 24 hours after and at least 24 hours prior to irrigation.

Results & Discussion

Figure 6:
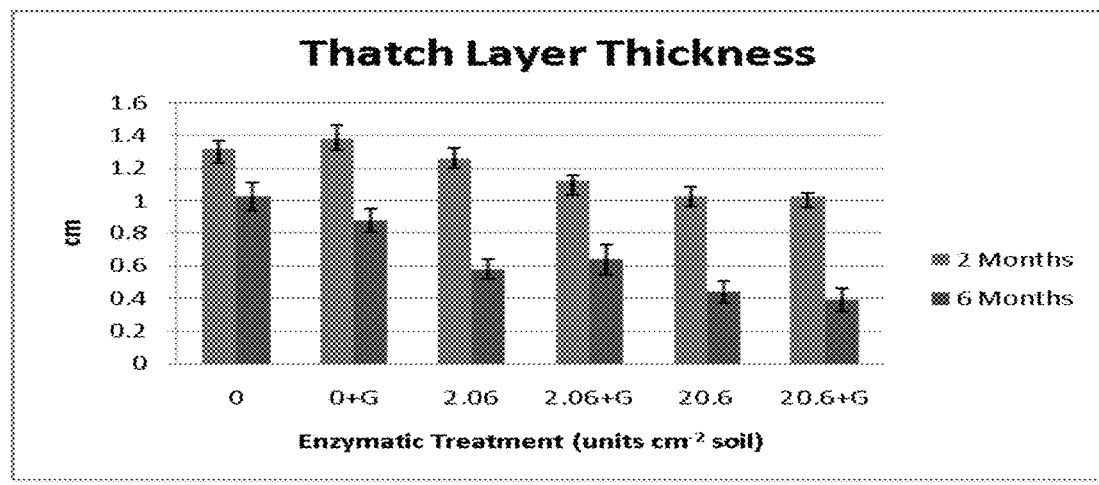
FIG. 6 is a bar graph illustrating thatch layer thickness (TLT) on dead bentgrass pots after two and six months of treatment with three different levels of laccase (0 (control), 2.06 and 20.6 units cm$^{-2}$, with and without the mediator, guaiacol (G).
Figure 7:
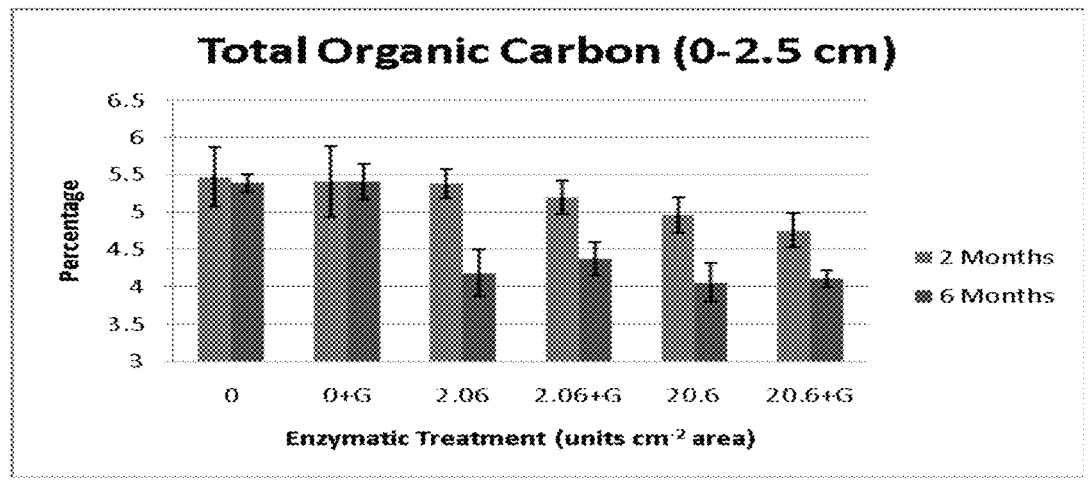
FIG. 7 is a bar graph illustrating total organic carbon (TOC) on dead bentgrass pots after two and six months of treatment with three different levels of laccase (0 (control), 2.06 and 20.6 units cm$^{-2}$, with and without the mediator, guaiacol (G).
Figure 8:
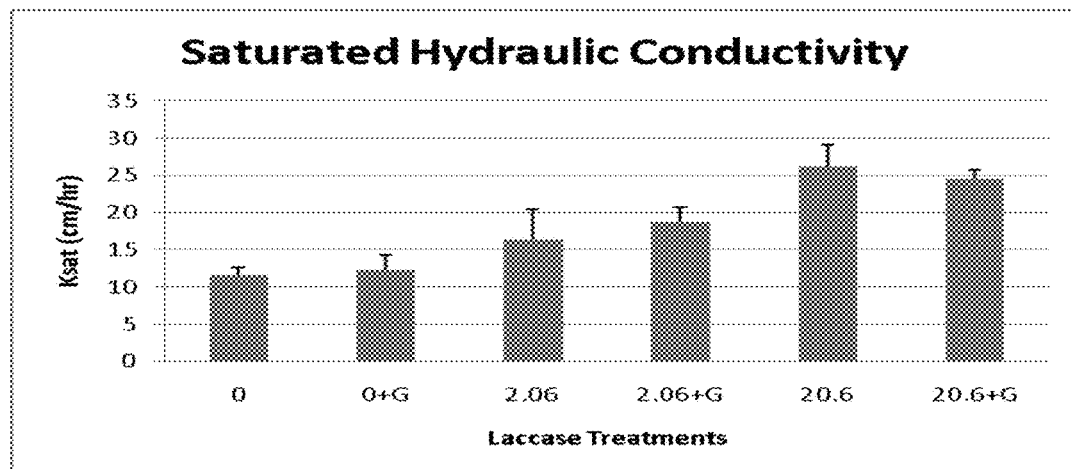
FIG. 8 is a bar graph illustrating saturated hydraulic conductivity (SHC) on dead bentgrass pots after two months of treatment application with three different levels of laccase (0 (control), 2.06 and 20.6 units cm$^{-2}$, with and without the mediator, guaiacol (G).

For all treatments, ten replicates were prepared. Five replicates were sampled during February 2010, after two months of treatment, and the other five replicates were sampled after six months of treatment. The results are presented in FIGS. 6, 7, and 8, and again confirmed the finding on live grass from Example 2, above, that the enzyme treatment effectively reduces thatch.

After two months of treatment application, thatch layer thickness was reduced by 22.1% and extractive-free acid-soluble lignin by 12.3%. Lignin content decreased by 6.5% and saturated hydraulic conductivity improved to 124.7% higher than the non-treated control. No reduction in organic matter and sugar content was observed after two months of treatment application. After six months, thatch layer thickness was reduced by 62.0%, total organic content (0-2.5 cm) by 24.7%, and total sugar content by 29.3%. Extractive-free acid-insoluble lignin and saturated hydraulic conductivity increased by 17.1 and 70.8%, respectively in comparison to the control.

This greenhouse research demonstrated the efficacy of bi-weekly applications of laccase enzyme at 2.06 and 20.6 units $cm^{-2}$ to change physical/structural and chemical composition properties of the thatch layer of creeping bentgrass turf. Laccase application was effective in reducing organic matter content, thatch layer thickness, and sugar content and in increasing saturated hydraulic conductivity. Laccase application at 2.06 units $cm^{-2}$ was not effective after two months of treatment application in reducing thatch layer thickness and sugar content but was effective after six months of application. Duration of treatment application had a positive effect on organic matter degradation. Implications of these findings point that laccase application at 2.06 units $cm^{-2}$ can be as effective as laccase activity level of 20.6 units $cm^{-2}$ when applied over a period of time. These results provide encouragement that direct applications of laccase enzyme can enhance decomposition of organic matter and reduce problems associated with excessive thatch.

Example 4

Field Study 1: Bermudagrass and Zoysiagrass

The greenhouse study on creeping bentgrass (*Agrostis stolonifera* L.) described in Example 2 demonstrated that direct application of laccase solution every two weeks reduced the rate of accumulation of organic matter and hence buildup of thatch layer. To further investigate the effect of laccase solution on thatch development, a two year field study was conducted on an ultra-dwarf bermudagrass (*Cynodon dactylon* X *Cynodon transvaalensis* Burtt Davy, TifEagle') research green, and zoysiagrass (*Zoysia japonica* Stued., 'Meyer') maintained as a home lawn.

Materials & Methods

Two year field studies were conducted on ultra-dwarf bermudagrass and zoysiagrass at The University of Georgia, Griffin Campus as part of a two year experiment from June 2010 to January 2012. TifEagle bermudagrass was established in May 2009 on a sand-based research green (90:10 sand and Dakota peat moss) based on USGA specifications. Bermudagrass plots (60 cm×30 cm) occupied only a very small portion of the overall research green, which was generally maintained under low-input management protocols with much lower fertility, higher mowing height, and low mowing frequency than typical golf course putting greens. The low-input bermudagrass research green was fertilized during the growing season at the rate of 50 kg $ha^{-1}$ N provided by granular fertilizer 24-4-0 ($N-P_2O_5-K_2O$) (Lesco., Strongsville, Ohio) (1 pound N $1000^{-1}$ sq. ft.) three times each year. The bermudagrass research green was mowed three times a week with clippings removed by Toro Greensmaster 3100 (The Toro Company, Bloomington, Minn.) and maintained at a height of 0.42 cm. To avoid confounding effects, the test site was excluded from routine thatch management cultural practices including core aeration and sand topdressing. Meyer zoysiagrass was established on a Cecil soil a fine, kaolinitic, thermic Typic Kanhapludults (Table 6) in July 2007 and was maintained under home lawn conditions, mowed once a week at 4 cm height with clippings returned. Zoysiagrass was fertilized with 12 kg $ha^{-1}$ N as granular 24-4-10 (Lesco Strongsville, Ohio) once each May, June, July and August (1 pound N $1000^{-1}$ sq. ft.) each year.

Laccase activity was quantified by a colorimetric assay using a Beckman DU 640B spectrophotometer (Beckman Instruments Inc., Fullerton, Calif.) spectrophotometer. One unit of laccase activity is the amount of enzyme that causes an absorbance change at 468 nm at a rate of 1.0 unit $min^{-1}$ in 3.4 mL of 1 mM 2,6-dimethoxyphenol, a specific substrate for laccase, in citrate-phosphate buffer at pH 3.8 (Park et al., 1999).

The field experiments on bermudagrass and zoysiagrass were a completely randomized design with two levels of laccase activity (0 and 2.1 units $cm^{-2}$) replicated four times. Year two plots were established in the same location adjacent to the first year plots. During the first year, laccase from white-rot fungi *Trametes versicolor* (Sigma-Aldrich product 53739) was applied as 410 mL solution at 0 and 2.1 units $cm^{-2}$ activity level every two weeks on bermudagrass and zoysiagrass. During the second year laccase from *Pycnoporus* genus was used at the same activity level due to the unavailability of the Sigma Aldrich product. In a related one year study conducted on creeping bentgrass (unpublished), the two laccase sources were directly compared and no significant differences were observed in their performance.

Measurements

Effectiveness of laccase application and its impact on physical and chemical properties of thatch layer were determined after six months of treatment application each year. In year one, bi-weekly treatment applications began in June 2010 and continued until December 2010. In year two, bi-weekly treatment applications began in July 2011 and continued until January 2012. Samples were collected in four replicates and analyzed for different parameters prior to initiation of treatments to establish baseline data. Parameters measured included thatch layer thickness (TLT), organic matter content (OM) for a depth of 0-2.5 cm ($OM_U$), 2.5-5.0 cm ($OM_L$), and 0-5.0 cm (OM), saturated hydraulic conductivity (SHC), extractive-free acid-soluble lignin ($L_S$), and acid-insoluble lignin ($L_I$). Total lignin ($L_T$) was obtained by addition of acid-soluble and -insoluble lignin contents.

Thatch Layer Thickness

Thatch layer thickness was measured from two sub-samples of the soil profile from each plot. Replaceable wedge-shaped turf profiles (8.9 cm wide and 2.5 cm thick) were pulled using AMS Turf Profiler (AMS Inc., American Falls, Id.). Thatch layer thickness was measured from four points across the width of each profile and averaged. The clearly visible distinction between thatch layer and mat/soil layer below was considered as the bottom of the thatch layer for all measurement locations.

Organic Matter Content

Organic matter (OM) was measured by total ignition as described by Carrow et al. (1987), which is hereby incorporated by reference herein. Two soil cores (2.0 cm diam.) were obtained from each plot and divided into 0-2.5 cm ($OM_U$) and 2.5-5.0 cm ($OM_L$) depths. The cores consisted of thatch layer which constituted the major portion of the 0-2.5 cm profile. The cores were dried in an oven at 100±5° C. for 24 h and weighed. Soil cores were ashed in a muffle furnace at 600±10° C. for 24 h and weighed again. Total organic carbon content was determined as the difference in the two readings and percent organic matter was calculated.

Saturated Hydraulic Conductivity

The saturated hydraulic conductivity (SHC) from each plot was measured by a constant hydraulic head method using a Marriott tube apparatus and saturated hydraulic conductivity was calculated using Darcy's equation. An intact core (diam. 4.7 cm and length 7.7 cm) was obtained from each plot in a brass cylinder using an undisturbed soil core sampler (Model 0200 soil sampler, Soilmoisture Equip. Corp., Santa Barbara, Calif.). The bottom of the core was covered with a double layer of cheesecloth held in place with a rubber band and saturated overnight in a 0.05 N $CaCl_2$ solution to minimize dispersion. A steady state flow through the samples was established by flowing 0.05 N $CaCl_2$ through the core for 10 min. After 10 min the volume of water that passed through the core was measured for one minute and the measurement was repeated three times.

Extractive-Free Liqnin Content

Thatch biomass was collected from the top 2.5 cm of each core after measurement of saturated hydraulic conductivity. Each core was clipped in the laboratory to remove verdure. Thatch samples were first air-dried, ground, washed with water in a glass jar, on a rotary shaker at 200 rpm, and then passed through a series of sieves with an 841 μm sieve at the top and a 177 μm sieve at the bottom. The biomass retained by the 177 μm sieve size was used for analysis. The thatch biomass was extracted for 24 h using the Soxhlet method for water- and alcohol-soluble extractives using de-ionized water and 16.26 M (95 percent USP grade) ethyl alcohol, respectively (NREL, 2008a). Lignin content determined from an extracted biomass is known as extractive-free lignin content.

Extractive-free acid-soluble lignin ($L_S$) and acid-insoluble lignin ($L_I$) content in the thatch layer biomass was determined on weight basis in a two-step acid-hydrolysis procedure (NREL, 2008b). In the first step, extractive-free thatch samples were hydrolyzed for 60 min with 72% $H_2SO_4$ at 30° C. in a water bath. In the second step, $H_2SO_4$ was diluted to 4% and the samples were autoclaved at 121° C. for 1 h and then vacuum filtered. Acid-soluble lignin, which consists of low molecular weight phenolic groups, was determined using this hydrolysis liquid at 240 nm wavelength in a Beckman DU 640B spectrophotometer (Beckman Instruments Inc., Fullerton, Calif.). The solids remaining after acid hydrolysis were dried in an oven at 100±5° C. for 24 h, weighed, ashed in a muffle furnace at 600±10° C. for 24 h, and weighed again to calculate the acid-insoluble lignin content using weight difference. Total lignin content ($L_T$) of each sample was calculated as the sum of $L_S$ and $L_I$.

Statistical Analysis

Data from a completely randomized design with treatments consisting of two levels of laccase were analyzed separately for each species. Analysis of variance (ANOVA) using general linear model (GLM) was performed to evaluate the main effects of treatments and their interaction with years (SAS Institute, 1994). The two-year combined analysis of variance in many instances indicated significant year affects and treatment by year interactions therefore the data was reanalyzed by year and summarized for each year separately. Since only two treatments were compared, mean separation testing was unnecessary and the results of the ANOVA F-test for treatment was used to determine statistical differences at $\alpha=0.05$.

Results

Organic Matter Content

Figure 9:
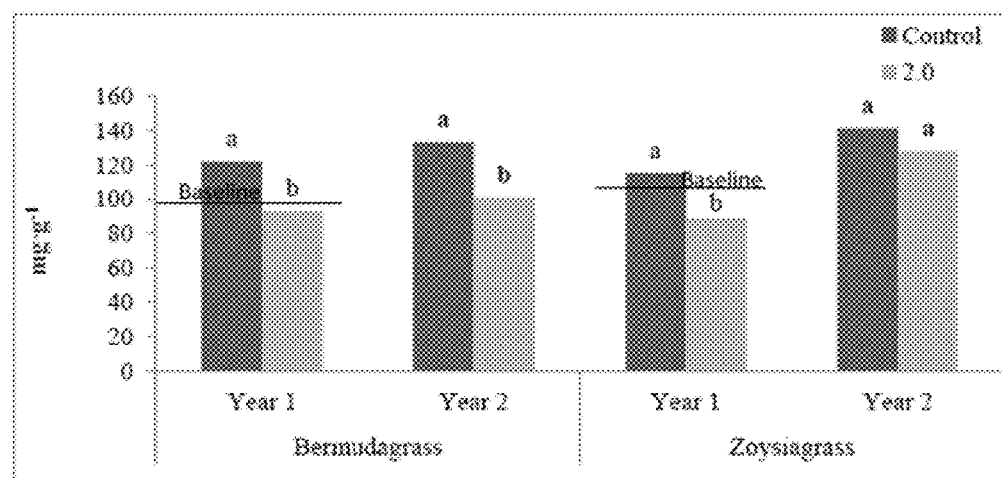
FIG. 9 is a bar graph illustrating organic matter content (0-2.5 cm, $OM_U$) after bi-weekly application of laccase on bermudagrass and zoysiagrass with two levels 0 (control) and 2.0 units cm$^{-2}$. Values are means of four replicates. Treatment means within each year with same letter above the bars (year 1=standards, year two=bolded) were not statistically different at $\alpha=0.05$ according to the ANOVA F-test for treatments. The horizontal line represents the baseline reading at the start of the experiment.

For bermudagrass, a significant treatment effect was observed for $OM_U$ ($P \leq 0.05$) and OM ($P \leq 0.05$) during year one and for $OM_U$ ($P \leq 0.05$) during the second year (Table 7). The $OM_U$, $OM_L$ and OM content at the start of the experiment were 97, 07, and 41 g·kg$^{-1}$, respectively. Organic matter content (0-2.5 cm) after six months of treatment was 122 and 93 g·kg$^{-1}$ for control and plots treated with laccase, respectively (FIG. 9). The results indicate that in laccase treated bermudagrass plots $OM_U$ was 23 and 24% lower in comparison to control plots in first and second year, respectively (FIG. 9). Laccase application prevented organic matter accumulation in the treated plots as compared to the control plots. No differences were observed for $OM_L$ after six months of laccase application between control and treated plots (Table 8). Organic matter (0-5.0 cm) accumulation was observed in control plots after six months. No accumulation was observed in plots treated with laccase enzyme. In year one, plots treated with laccase had 20% lower OM than the control plots. However, no significant difference was observed in OM between laccase treated and untreated plots during the second year (Table 8).

For zoysiagrass, a significant effect of laccase treatment was observed on $OM_U$ ($P \leq 0.05$) during first year of the experiment (Table 7). A reduction of 23% $OM_U$ in plots treated with laccase were observed when compared to control plots in year one (FIG. 9). However, no significant effect was observed for $OM_U$, $OM_L$, and OM during the second year (Table 8).

Thatch Layer Thickness

Figure 10:
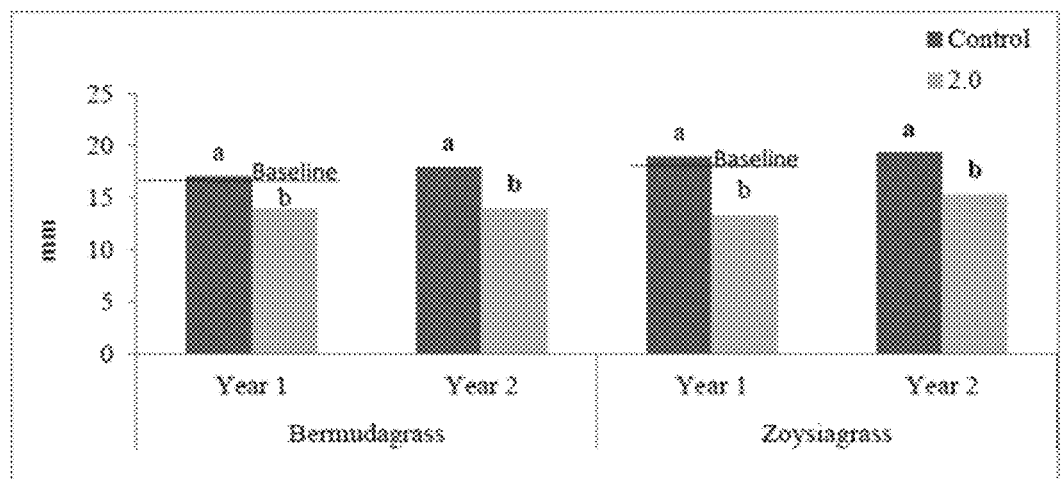
FIG. 10 is a bar graph illustrating thatch layer thickness (TLT) after bi-weekly application of laccase on bermudagrass and zoysiagrass with two levels 0 (control) and 2.0 units cm$^{-2}$. Values are means of four replicates. Treatment means within each year with same letter above the bars (year 1=standards, year two=bolded) were not statistically different at $\alpha=0.05$ according to the ANOVA F-test for treatments. The horizontal line represents the baseline reading at the start of the experiment.

A significant effect of laccase application was observed for TLT ($P \leq 0.05$) in the first and second year of the experiment in bermudagrass (Table 7). Thatch layer thickness prior to treatment application averaged 16.6 mm. The reduction in TLT in plots treated with laccase was 18 and 22% in comparison to control plots during year one and two, respectively (FIG. 10). A slight accumulation in TLT was observed in control plots above the starting value of 16.6 mm at the end of first year treatment application. However, application of laccase proved effective in reducing TLT after six months of application.

In zoysiagrass, laccase application was effective ($P \leq 0.001$) in reducing TLT in both years relative to the control (Table 7). TLT at the start of the experiment averaged 18.5 mm with a slight accumulation of thatch in the control plots by the end of year one and two (FIG. 10). However, laccase application proved to be effective in reducing thatch layer thickness with a reduction of 30 and 21% in TLT observed in plots treated with laccase when compared to control plots in first and second year, respectively (FIG. 10).

Saturated Hydraulic Conductivity

Figure 11:
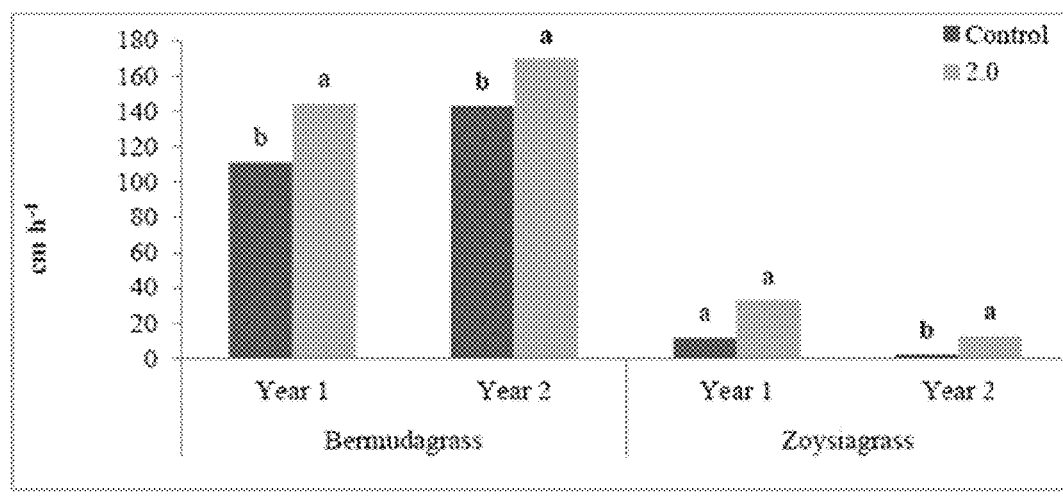
FIG. 11 is a bar graph illustrating the saturated hydraulic conductivity (SHC) after bi-weekly application of laccase on bermudagrass and zoysiagrass with two levels 0 (control) and 2.0 units cm$^{-2}$. Values are means of four replicates. Treatment means within each year with same letter above the bars (year 1=standards, year two=bolded) were not statistically different at $\alpha=0.05$ according to the ANOVA F-test for treatments.

When compared to the control plots, laccase application to bermudagrass significantly improved SHC (P≤0.05, Table 2) by 30 and 19% in year 1 and year 2, respectively (FIG. 11). In zoysiagrass, a significant effect of laccase on SHC was observed in the second year (P≤0.01) (Table 2). After six months of treatment in the second year, SHC increased from 2.1 to 12.5 cm h$^{-1}$ (FIG. 11).

Extracted-Free Lignin Content

Application of laccase significantly affected $L_S$, $L_I$, and $L_T$ in bermudagrass in both years (Table 7). A slight but significant reduction of 5-10 g·kg$^{-1}$ in $L_S$ was observed in plots treated with laccase in comparison to control plots in both years (Table 8). Content of Land $L_T$ content were reduced for plots treated with laccase in the range of 45-48 and 50-58 g·kg$^{-1}$ over control plots in year one and two (Table 8, FIG. 12).

Figure 12:
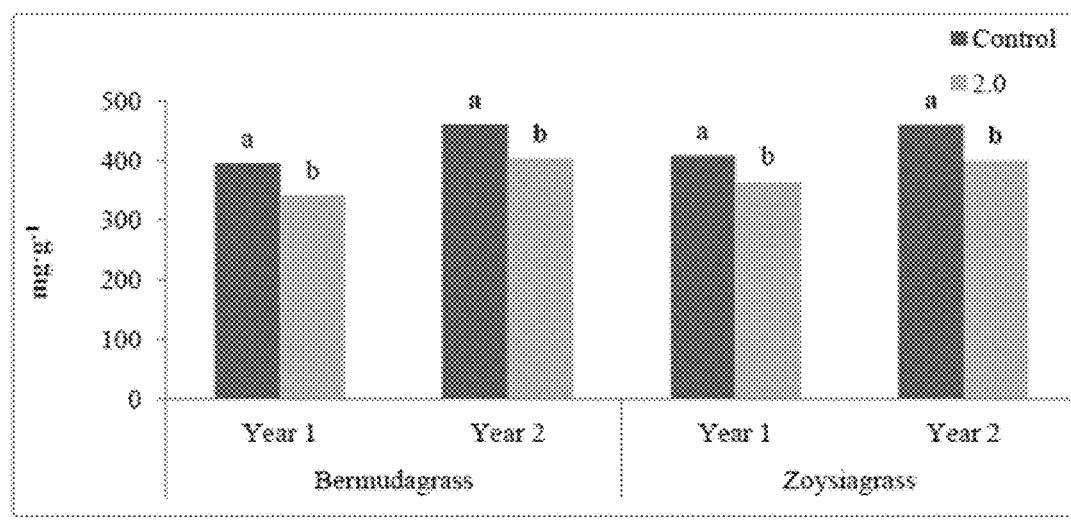
FIG. 12 is a bar graph illustrating total lignin content ($L_T$) after bi-weekly application of laccase on bermudagrass and zoysiagrass with two levels 0 (control) and 2.0 units cm$^{-2}$. Values are means of four replicates. Treatment means within each year with same letter above the bars (year 1=standards, year two=bolded) were not statistically different at $\alpha=0.05$ according to the ANOVA F-test for treatments.

In zoysiagrass, laccase application had a significant effect on $L_S$ (P 0.001), $L_I$ (P≤0.001), and $L_T$ (P≤0.001) in both year one and two (Table 7). Acid-soluble lignin content reduced in the range of 3.1-7.3 g·kg$^{-1}$ and $L_I$ content decreased in the range of 41-49 g·kg$^{-1}$ in laccase treated plots when compared to control plots during first and second year, respectively (Table 8). A significant 44-57 g·kg$^{-1}$ reduction in $L_T$ was observed in plots treated with laccase when compared to control plots (FIG. 12).

Discussion

The study in Example 2 tested the effects of direct application of laccase on creeping bentgrass under greenhouse conditions that were conducive for thatch development (Sidhu et al., 2012). Application of laccase at activity levels of 2.06 units cm$^{-2}$ every two weeks was shown to be effective in reducing the rate of accumulation of thatch-mat, OM, and significantly increased SHC over the controls (Sidhu et al., 2012). Although laccase treatment reduced the rate of accumulation and thatch layer buildup, some accumulation of organic matter and thatch buildup was observed after nine months (Sidhu et al., 2012).

In the present Example with bermudagrass and zoysiagrass grown under low-input (low N) field conditions, an actual reduction in organic matter and thatch layer was observed in plots treated with laccase after six months when compared to initial pre-treatment levels (FIGS. 9, 10). Furthermore, the control plots of both grass species showed a slight accumulation of organic matter and thatch layer after six months. These results indicate that bi-weekly laccase treatment applications for six months were effective in reducing thatch layer thickness in bermudagrass and zoysiagrass and $OM_U$ in bermudagrass in both years of study. Turf managed more intensively and with higher N applications than the sites used in this study would likely have higher rates of thatch accumulation.

In zoysiagrass, $OM_U$ content was significantly lowered in laccase treated plots when compared to control plots in year one but no significant difference was observed in year two during the study. A significant increase was observed in SHC in plots treated with laccase application (FIG. 11). This may be attributed to the reduction in thatch layer thickness and organic matter content. The presence of higher levels of organic matter in the thatch layer is known to decrease water infiltration through the thatch layer (McCarty et al., 2005). A reduction in $L_S$, $L_I$, and $L_T$ was observed in both years for both grasses in plots treated with laccase (Table 8, FIG. 12). This may be attributed to the oxidation and eventually degradation of lignin macromolecule. Laccases are produced as extracellular enzymes by white-rot fungi and facilitate the oxidation of wide range of mono- and di-diphenols using oxygen as the electron acceptor (Baldrian, 2006). Lignin phenolic compounds are oxidized by laccase via Cα-Cβ cleavage, alkyl-aryl cleavage, and Cα oxidation (Wong, 2009). Laccase enzyme acts on bonds formed between lignin macromolecule and between lignin and structural sugars leading to opening up of the biomass structure leading to increased availability of easily degradable sugars by microbes. The laccase enzymes used in this study are stable over a wide range of pH and temperature (Baldrian, 2006; Munoz et al., 1997; Stoilova et al., 2010; Thurston, 1994). In research presented here, laccase enzyme effectively managed thatch over a range of environmental conditions for the period of the study. This suggests that laccase enzyme treatment may be a valuable non-disruptive means to control thatch in these species.

This field research was the first known study to demonstrate the efficacy of laccase application on an ultra-dwarf bermudagrass grown on a low-input research green and on zoysiagrass grown under home lawn conditions. The results revealed the positive impacts of laccase on physical and chemical properties of thatch layer that resulted in no net accumulation of thatch or organic matter and an increase in saturated hydraulic conductivity. Highly managed turf with high potential for thatch development such as golf course putting greens are likely to be the most feasible for commercialization of this new approach.

Tables for Example 4:

TABLE 6

Characteristics of soil used in zoysiagrass study

| Soil Type | Sandy Clay Loam |
|---|---|
| pH | 6.1 |
| Ca | 1249 |
| K (Mehlich 1 mg · kg$^{-1}$) | 146.9 |
| Mg (Mehlich 1 mg · kg$^{-1}$) | 196.3 |
| Mn (Mehlich 1 mg · kg$^{-1}$) | 65.38 |
| P (Mehlich 1 mg · kg$^{-1}$) | 22.16 |
| Zn (Mehlich 1 mg · kg$^{-1}$) | 7.16 |
| Sand (%) | 55.70 |
| Silt (%) | 20.00 |
| Clay (%) | 24.30 |

TABLE 7

Analysis of variance (ANOVA) table showing the effects of laccase treatments, treatment duration, and duration and treatment interactions on organic matter ($OM_U$, 0-2.5 cm; $OM_L$, 2.5-5.0 cm; OM, 0-5.0 cm), thatch layer thickness (TLT), saturated hydraulic conductivity (SHC), acid-soluble lignin ($L_S$), acid-insoluble lignin ($L_I$), and total lignin ($L_T$) on ultra-dwarf bermudagrass and zoysiagrass.

| | Df | Organic matter $OM_U$ (0-2.5 cm) | Organic matter $OM_L$ (2.5-5.0 cm) | Organic matter OM (0-5.0 cm) | Thatch layer thickness TLT | Saturated hydraulic conductivity SHC | Acid-soluble lignin $L_S$ | Acid-insoluble lignin $L_I$ | Total lignin $L_T$ |
|---|---|---|---|---|---|---|---|---|---|
| | | | | | mean square value | | | | |
| Bermudagrass | | | | | | | | | |
| Year 1 | | | | | | | | | |
| Treatment | 1 | 1728* | 30 | 170* | 18* | 2169* | 166** | 3987*** | 5782*** |
| Error | 6 | 218 | 8 | 20 | 2 | 303 | 5 | 31 | 31 |
| Year 2 | | | | | | | | | |
| Treatment | 1 | 2062* | 336 | 372 | 32* | 1445* | 202*** | 4532*** | 6649*** |
| Error | 6 | 232 | 101 | 104 | 1 | 157 | 8 | 41 | 34 |
| Zoysiagrass | | | | | | | | | |
| Year 1 | | | | | | | | | |
| Treatment | 1 | 1382*** | 216 | 54 | 63*** | 908 | 19*** | 3351*** | 3892*** |
| Error | 6 | 26 | 69 | 9 | 4 | 411 | 0.01 | 8 | 10 |
| Year 2 | | | | | | | | | |
| Treatment | 1 | 384 | 3 | 42 | 31*** | 216** | 107*** | 4841*** | 6391*** |
| Error | 6 | 53 | 17 | 26 | 0.4 | 14.5 | 1 | 68 | 67 |

*Significant at the 0.05 probability level;
**Significant at the 0.01 probability level;
***Significant at the 0.001 probability level

TABLE 8

Organic matter content ($OM_L$, 2.5-5.0 cm; OM, 0-5.0 cm), acid-soluble lignin ($L_S$), and acid-insoluble lignin ($L_I$) content after first and second year of laccase treatments on ultra-dwarf bermudagrass and zoysiagrass. Organic matter and lignin content values are on dry weight basis.

| | Organic matter (2.5-5.0 cm) $OM_L$ | | Organic matter (0-5.0 cm) OM | | Acid-soluble lignin $L_S$ | | Acid-insoluble lignin $L_I$ | |
|---|---|---|---|---|---|---|---|---|
| | Year 1 | Year 2 | Year 1 | Year 2 | Year 1 | Year 2 | Year 1 | Year 2 |
| | | | | g · kg$^{-1}$ | | | | |
| Bermudagrass | | | | | | | | |
| Control | 9.9a† | 22.2a | 47.5a | 58.1a | 41.5a | 49.5a | 317.5a | 412.1a |
| 2.1 (2) | 6.1a | 9.2a | 38.2b | 44.5a | 36.7b | 39.5b | 272.8b | 364.5b |
| Zoysiagrass | | | | | | | | |
| Control | 66.9a | 68.0a | 87.2a | 94.0a | 23.7a | 29.6a | 385.7a | 430.4a |
| 2.1 (2) | 77.3a | 66.6a | 82.1a | 89.4a | 20.6b | 22.3b | 344.7b | 381.2b |

†Means within a column for grass species followed by the same letter are not significantly different at α = 0.05 according to the ANOVA F-test for treatments Example 5

Field Study 2: Creeping Bentgrass

A two-year field experiment was conducted on creeping bentgrass (*Agrostis stolonifera* L.) to optimize the laccase activity level, frequency of application, and to determine potential interactions with core aeration and topdressing cultural practices. Results indicated that laccase treatments were effective in reducing thatch layer thickness (TLT) at rates as low as 0.5 units cm$^{-2}$ applied every two weeks and as infrequent as once a month when applied at a rate of 2.0 units cm$^{-2}$. Laccase application at 2.0 units cm$^{-2}$ once in four weeks was just as effective at reducing TLT as was core aeration and sand topdressing twice per year. Even greater reductions in TLT were observed when laccase was applied in combination with core aeration and sand topdressing.

Materials & Methods

A two year field study on 'Crenshaw' creeping bentgrass, *Agrostis stolonifera* L. (Engelke et al., 1995), was conducted at The University of Georgia, Griffin Campus from June 2010 to January 2012. The experiment was conducted on a 25-year old bentgrass green established as a sand-based putting green with 90:10 sand and organic matter mix (Michigan peat) based on USGA specifications (USGA Green Section Staff, 1973). The bentgrass green was mowed three times a week using a Toro Greensmaster 3100 (The Toro Company, Bloomington, Minn.) set at a height of 0.42 cm.

Bi-weekly fungicide applications on the green were performed from the third week of April to third week of November to control dollar spot (*Sclerotinia homoeocarpa* F. T. Bennett), brown patch (*Rhizoctonia solani* Kuhn), anthracnose (Colletotrichium graminicola sensu lato Crouch, Clarke, and Hillman), and *Pythium* blight (*Pythium aphanidermatum* (Edson) Fitzp). The fungicide spray routine for both years consisted of applications of Banner MAXX® at 3.2 L ha$^{-1}$ (14.3% propioconazole [1-[[2-(2,4-dichlorophenyl)-4-propyl-1,3-dioxolan-2-yl]methyl]-1H-1, 2,4-triazole], Syngenta Crop Protection, Inc., Greensboro, N.C.) from April to May. From the last week of May to third week of September fungicide treatments every two weeks consisted of a mixture containing Daconil® (40.4% chlorothalonil [tetrachloroisophthalonitrile], Syngenta Crop Protection, Inc., Greensboro, N.C.) at the rate of 11.5 L ha$^{-1}$ alternating with Subdue MAXX® (22% Mefenoxam [(R, S)-2-[(2,6-dimethylphenyl)-methoxyacetylamino]-propionic acid methyl ester], Syngenta Crop Protection, Inc., Greensboro, N.C.) at 1.6 L ha$^{-1}$ and with Banner MAXX® at rate of 9.6 L ha$^{-1}$. Fertilizer application for both years consisted of 50 kg ha$^{-1}$ granular fertilizer 24-4-10 (N—P$_2$O$_5$—K$_2$O) (Lesco. Strongsville, Ohio) in the third week of March, September, and October and 2 kg ha$^{-1}$ soluble 20-20-20 fertilizer (JR Peters Inc, Allentown, Pa.) every two weeks starting the third week of April thru September made in combination with a fungicide application. Irrigation was routinely applied uniformly across all plots to prevent soil moisture stress.

Two repetitions of the experiment were conducted in consecutive years and each experiment consisted of four replications of ten treatments in a completely randomized block design. A priori comparisons of groups of treatments from the experiment were used to evaluate: laccase rates; frequency of application; and influence of cultural management practices (core aeration and topdressing) (Table 9).

During the first year, laccase enzyme produced from white-rot fungi *Trametes versicolor* (L.) Lloyd was purchased from Sigma Aldrich (product 53739, Sigma Aldrich Inc., St. Louis, Mo.) and was sprayed as 410 mL solution over an area of 0.185 m$^2$ at five activity levels [0 (control), 0.5, 1.0, 2.0, and 4.0 units cm$^{-2}$] every two weeks. Laccase activity level of 2.0 units cm$^{-2}$ was applied at four different frequencies (2, 4, 8, and 12 weeks). Plots receiving cultural management treatments were core-aerated and sand topdressed twice yearly in April and September. Core aeration was accomplished using a Ryan Greensaire 24 Aerator (Ryan Inc. Johnson Creek, Wis.) fitted with 1.27 cm tines on a spacing of 5.0×5.0 cm and adjusted to penetrate to a depth of 6.25 cm. Immediately following core aeration, sand topdressing with 1134 g of sand (Quikrete Premium Play Sand) per plot was accomplished using a Scotts Precision Green Spreader. Laccase applications associated with cultural management treatments were applied at 2.0 units cm$^{-2}$ every four weeks.

Laccase from Sigma Aldrich became unavailable prior to initiation of the second year's experiment. However, a previous study that compared laccase from Sigma Aldrich to other laccase sources showed no differences in effectiveness among laccase sources (Sidhu, 2012). Therefore one of these alternative sources of laccase from *Pycnoporus* genus produced at Jaingnan University in China was used for all treatments during the second year of this study. For the sake of brevity, laccase treatments hereafter will be mentioned as activity levels (i.e., rate) followed by the frequency of laccase application in parenthesis.

Laccase activity assay, organic matter content (OM), saturated hydraulic conductivity (SHC), thatch layer thickness (TLT), extractive-free lignin content (soluble ($L_S$) and insoluble ($L_I$)) and statistical analysis were conducted as described in Example 4, above.

Extractive-Free Sugar Content

Sugar content determined from biomass after removal of water- and alcohol-soluble extractives is known as extractive-free sugar content. Monosaccharide sugars that are components of structural polysaccharides, cellulose and hemicellulose were measured. The total sugar content ($T_S$) was determined by addition of sugar content for glucose ($S_{GLU}$), xylose ($S_{XYL}$), arabinose ($S_{ARA}$), galactose ($S_{GAL}$), and mannose ($S_{MAN}$). Sugar content was measured using hydrolysis liquid collected after vacuum filtration in the above step. The hydrolysis liquid was neutralized to a pH range 7.0-8.0 using NaHCO$_3$ and monosaccharide sugars were determined using high performance liquid chromatography (HPLC) in an Agilent 1100 HPLC (Aligent Technologies, Waldbronn, Germany) with binary pump and refractive index detector. An AMINEX HPX-87P 7.8×300 mm Pb$^{2+}$ carbohydrate analysis column (Bio-Rad, Hercules, Calif.) was used at 85° C. with deionized water as mobile phase at a flow rate of 0.6 mL min$^{-1}$.

Results

Laccase Rates

Laccase treatments of 0 (2), 0.5 (2), 1.0 (2), 2.0 (2), and 4.0 (2), where rate of laccase activity is followed by frequency of application in weeks in parenthesis, were grouped together to observe the effect of rate of laccase application. A significant year effect was observed for OM$_U$ (P≤0.05), L$_S$ (P≤0.01), L$_I$ (P≤0.001), L$_T$ (P≤0.001), S$_{GAL}$ (P≤0.05), and S$_{ARA}$ (P≤0.05) (Table 2). A significant year by treatment interaction was observed for L$_I$ (P≤0.01) and L$_T$ (P≤0.01) (Table 10). A significant treatment effect was observed for TLT (P≤0.001), L$_S$ (P≤0.001), L$_I$ (P≤0.001), L$_T$ (P≤0.001), S$_{GLU}$ (P≤0.05), S$_{XYL}$ (P≤0.01), S$_{GAL}$ (P≤0.05) and S$_T$ (P≤0.05) (Table 10). No differences were observed for organic matter and saturated hydraulic conductivity. All laccase treatments decreased TLT by 3.8 to 4.8 mm (20 to 26%) and 4.9 to 5.5 mm (24 to 28%) in comparison to control during year one and two, respectively (FIG. 13A). No differences were observed for TLT among different rates of laccase application (FIG. 13A).

Figures 16A, 16B, 16C:
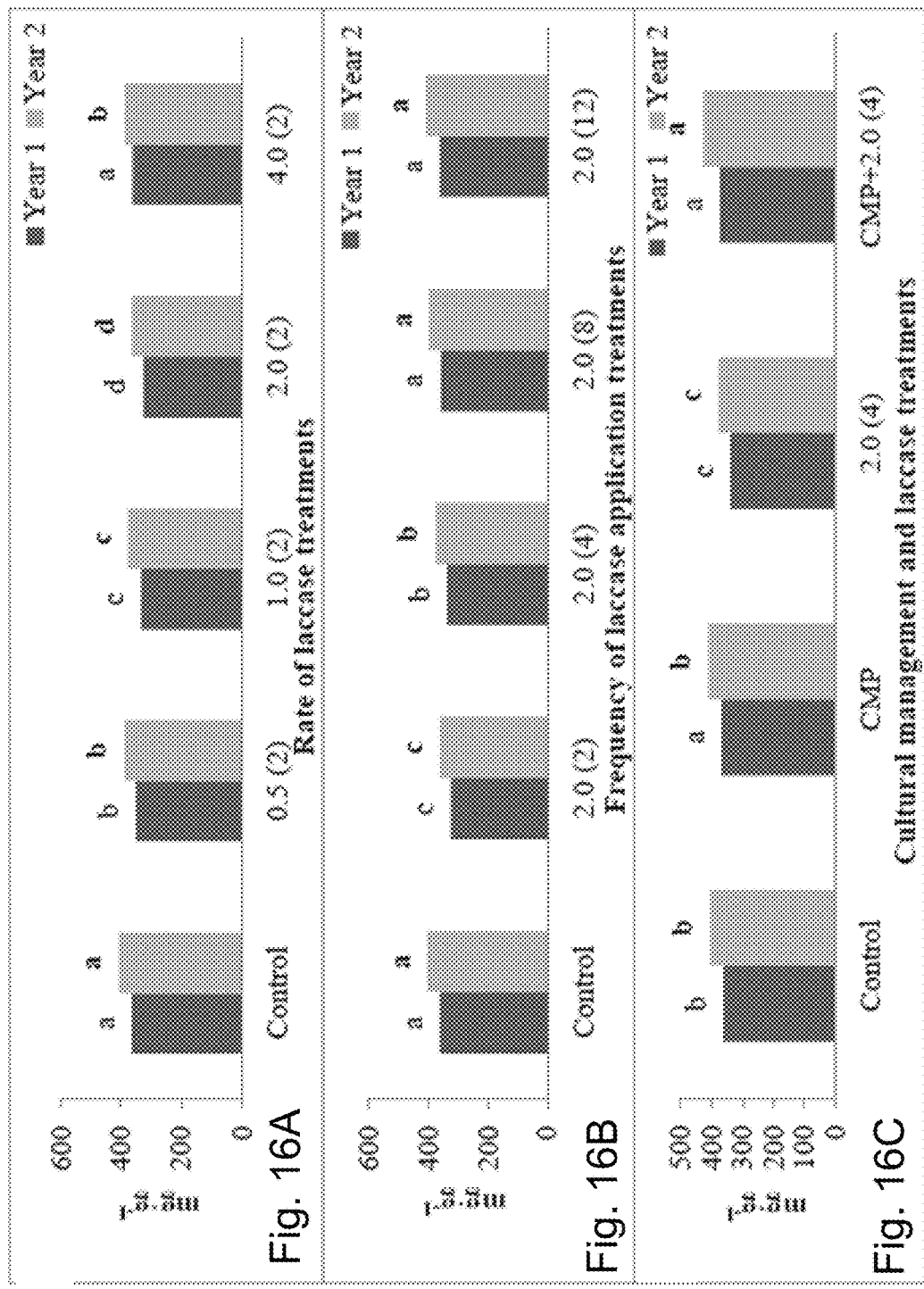
FIGS. 16A-16C are a series of bar graphs illustrating Extractive-free total lignin content ($L_T$) after six months of treatment application on creeping bentgrass with: five different levels of laccase (control, 0.5, 1.0, 2.0, and 4.0 units cm$^{-2}$.

Laccase treatments decreased L$_S$ by 6 to 12 mg·g$^{-1}$ and 4 to 12 mg·g$^{-1}$ when compared to control during year one and two, respectively (FIG. 14A). In year one, laccase treatment 4.0 (2) reduced L$_S$ compared to treatments 0.5 (2) and 1.0 (2). In the second year, L$_S$ decreased significantly with increasing laccase activity rate (FIG. 141A). A 5 to 29 mg·g$^{-1}$ and 13 to 35 mg·g$^{-1}$ reduction in L$_I$, which makes up the bulk of L$_T$, was observed over the control for first and second year, respectively with rate of laccase application up to 2.0 units cm$^{-2}$ (FIG. 15A). A similar reduction of 13 to 38 and 17 to 43 mg·g$^{-1}$ for L$_T$ with laccase application up to 2.0 units cm$^{-2}$ was obtained for year one and two, respectively when compared to control (FIG. 16A). However, acid-insoluble lignin content was similar to the control at laccase activity level of 4.0 units cm$^{-2}$ (FIG. 15A).

Total sugar content (S$_T$) in the thatch biomass decreased by 27 to 69 mg·g$^{-1}$ in year one and by 65 to 105 mg·g$^{-1}$ in year two relative to control with application of laccase (Table 11). A reduction in S$_{GLU}$, S$_{XYL}$, and S$_{GAL}$ was observed when laccase was applied above 1.0 units cm$^{-2}$ during year one (Table 11). A reduction in S$_{GLU}$ and S$_{XYL}$ content was observed in comparison to control for all the rates of laccase application during year two (Table 11). No reduction in $S_{GAL}$ was observed for any laccase treatment during year two (Table 11).

Frequency of Application

The frequency group of treatments included control, 2.0 (2), 2.0 (4), 2.0 (8), and 2.0 (12) and were compared to observe effect of laccase application frequency on thatch layer properties. A significant year effect was observed for TLT (P≤0.05), $L_S$ (P≤0.001), $L_I$ (P≤0.001), $L_T$ (P≤0.001), $S_{GAL}$ (P≤0.05), $S_{ARA}$ (P≤0.05), and $S_T$ (P≤0.05) (Table 10). Significant year by treatment interactions were observed for sugar contents (Table 10). A significant application frequency effect was observed for TLT (P≤0.001), $L_S$ (P≤0.01), $L_I$ (P≤0.001), $L_T$ (P≤0.001), $S_{GLU}$ (P≤0.05), $S_{XYL}$ (P≤0.001), $S_{GAL}$ (P≤0.01), and $S_T$ (P≤0.01) when compared to control (Table 10). Thatch layer thickness was reduced in comparison to control when laccase was applied at all the frequencies in both years (FIG. 13B). Laccase application at eight and twelve weeks in year two showed a slight increase in TLT in comparison to plots receiving laccase application at two and four weeks frequency (FIG. 13B). Laccase application at all frequencies reduced $L_S$ content in comparison to control in both years (FIG. 14B). The decrease in laccase application frequency showed slight increase in $L_S$ contents as is evident from higher $L_S$ content at 8 and 12 week frequency when compared to laccase treatment applied every two weeks in both years (FIG. 14B). Laccase treatments applied every two and four weeks were effective in reducing Land $L_T$ content in comparison to control in both years (FIG. 15B, 16B). As laccase application frequency decreased, $L_I$ and $L_T$ content increased in both years (FIG. 15B, 16B).

Total sugar content ($S_T$) in the thatch biomass tended to decrease with application of laccase in both years (Table 11). No change in $S_{GLU}$ content in comparison to control was observed for different laccase treatments during the first year (Table 11). During second year, a reduction in glucose content of thatch biomass was evident in all plots treated with laccase regardless of frequency compared to control plots (Table 11). In both years, the $S_{XYL}$ and $S_{GAL}$ contents in thatch biomass tended to be lower than in the control, especially at the 2 week frequency interval (Table 11).

Influence of Cultural Management Practices

Figure 17:
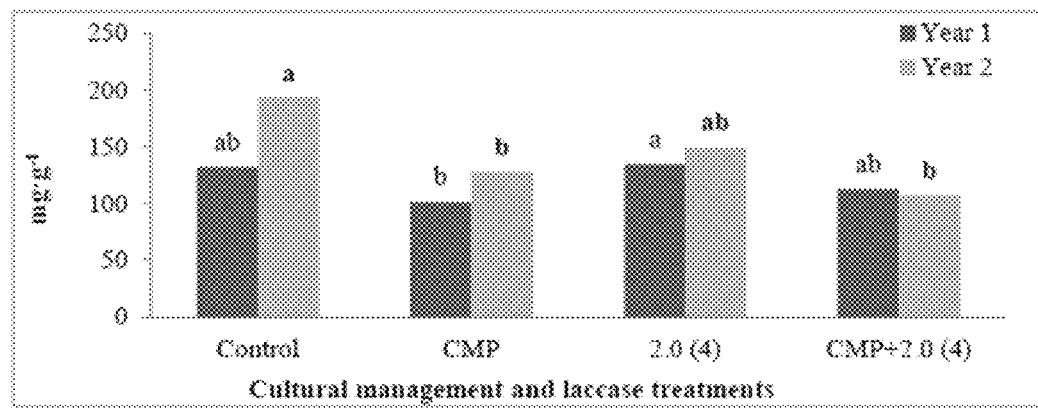
FIG. 17 is a bar graph illustrating organic matter content in the 0-2.5 cm surface layer ($OM_U$) after six months of treatment application on creeping bentgrass with laccase at 2.0 units cm$^{-2}$ applied at a frequency of 4 weeks in comparison with cultural management practice (control, cultural management practice (CMP), 2.0 (4), and CMP+2.0 (4)). Values are means of four replicates. Same letter on top of the bars (year one=standard, year two=bolded) are not considered to be statistically different according to Fisher's protected LSD at α=0.05.

Treatments in the cultural management group were control, CMP, 2.0 (4), and CMP+2.0 (4). Significant year effects were observed for lignin and sugar components (Table 10). Year by treatment interaction effects were obtained for TLT, $L_I$, $L_T$, $S_{XYL}$, $S_{GAL}$, and $S_{ARA}$ (Table 10). Significant treatment effects were obtained for OMU (P≤0.01), TLT (P≤0.001), SHC (P≤0.01) $L_S$ (P≤0.001), $L_I$ (P≤0.001), $L_T$ (P≤0.001), $S_{GLU}$ (P≤0.05), $S_{XYL}$ (P≤0.01), $S_{GAL}$ (P≤0.05), and $S_T$ (P≤0.01) (Table 10). In plots treated with CMP, $OM_U$ content decreased by 30.3 and 65.7 mg·g$^{-1}$ during year one and two, respectively when compared to control plots (FIG. 17). Similarly, $OM_U$ decreased from 132 to 113 mg·g$^{-1}$ during first year and from 193 to 108 mg·g$^{-1}$ during second year in plots treated with CMP-2.0 (4) as compared to control plots (FIG. 17). Thatch layer thickness was lower in plots receiving cultural management treatments and laccase treatments when compared to control plots (FIG. 13C). Plots treated with core aeration followed by sand topdressing along with application of laccase once in four weeks showed a significant reduction in thatch layer when compared to laccase application and cultural management treatment (FIG. 13C). A significant increase in SHC was observed during second year in plots treated with CMP+2.0 (4) as compared to control plots (FIG. 16).

Figure 18:
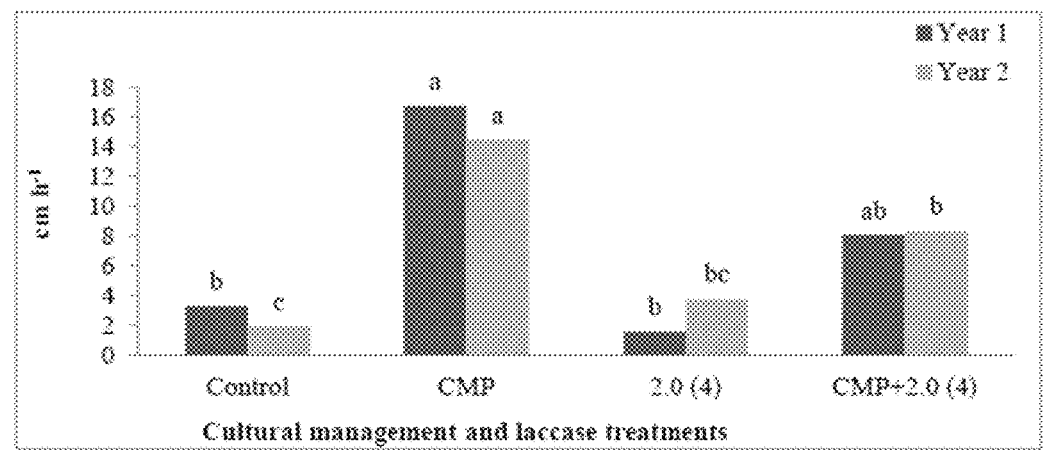
FIG. 18 is a bar graph illustrating saturated hydraulic conductivity (SHC) after six months of treatment application on creeping bentgrass with laccase at 2.0 units cm$^{-2}$ applied at a frequency of 4 weeks in comparison with cultural management practice (control, cultural management practice (CMP), 2.0 (4), and CMP+2.0 (4)). Values are means of four replicates. Same letter on top of the bars (year one=standard, year two=bolded) are not considered to be statistically different according to Fisher's protected LSD at α=0.05

Compared to control, other treatments in the cultural management group reduced acid-soluble lignin (FIG. 14C). Plots receiving laccase application had lower levels of $L_S$ as compared to plots treated with CMP in both years (FIG. 14C). Relative to control, acid-insoluble lignin content increased in plots receiving CMP and CMP+2.0 (4) treatments; but decreased in plots receiving only laccase enzyme (FIG. 15C). Plots receiving CMP+2.0 (4) treatment had increased levels of $L_I$ compared to plots receiving only cultural management practice (FIG. 15C). Total lignin content in plots receiving CMP-2.0 (4) treatment increased when compared to control; but decreased in plots receiving only laccase treatments (FIG. 16C). Total sugar content in thatch layer biomass from plots treated with CMP+2.0 (4) treatment was significantly lower than the control plots in both years (Table 11). Similarly, for the CMP+2.0 (4) treatment $S_{GLU}$, $S_{XYL}$, and $S_{GAL}$ (Table 11) contents were lower when compared to control treatment for both years. Plots treated with CMP showed reduced content of $S_{GAL}$ when compared to control for year one and two (Table 11). A reduction in xylose content was observed in plots treated with CMP as compared to control in first year but not in the second year (Table 11). No effect of CMP was observed on the glucose content (Table 11). Saturated hydraulic conductivity increased in plots treated with CMP by 12.6 to 13.6 cm h$^{-1}$ when compared to control plots and by 6.4 cm h$^{-1}$ in the second year for CMP+2.0 (4) (FIG. 18).

Discussion

Use of Laccase Application to Manage Thatch

Non-destructive methods to manage thatch are highly desirable. Several efforts in the past using different treatments and commercial products like sugars, mixtures of sugars and microbial inocula, mixture of amino acids and algae, and some enzymes like cellulase have shown contrasting results and most proved ineffective (Ledeboer and Skogley, 1967; Martin and Dale., 1980; McCarty et al., 2005; Murdoch and Barr, 1976). The inconsistent results of these studies may be attributed to the fact that they were focused on increasing microbial populations to increase organic matter decomposition. Maintaining elevated microbial activities over sustained periods of time under field turfgrass management systems is difficult due to the inability to maintain proper microenvironment conditions, particularly moisture and temperature regimes, required by particular microbial species.

Application of nitrogen as a fertilizer has been found to enhance activity of cellulose and glucosidase and suppress the activity of lignin degrading enzymes such as phenol oxidases and peroxidases (Gallo et al., 2004; Saiya-Cork et al., 2002; Sinsabaugh et al., 2005). One mechanism that explains the role of fertilization on soil enzymes is the nutrient resource allocation theory (Allison and Vitousek, 2005; Koch, 1985) that states that with increased availability of the nutrients, microbes tend to shift their resources away from production of nutrient acquiring enzymes. A negative correlation between P availability and activity of soil phosphatases was reported by Allison and Vitousek (2005) and by Olander and Vitousek (2000).

Another possible reason for contrasting results of the above mentioned studies was that they focused on degradation of cellulosic and hemicellulosic sugars instead of lignin. The focus of the present treatment is to provide at least partial degradation of the lignin protective matrix to allow bacterial population to act on the structural sugars.

To follow up on the positive results in earlier greenhouse studies described in Example 2 above, in the present study, the efficacy of laccase enzyme was verified under field conditions along with optimization of laccase application protocols in terms of rate and frequency of laccase application. Application of laccase in combination with core aeration and topdressing was effective in changing thatch characteristics.

Laccase Rates

In the present example, laccase enzyme was applied at five different rates (activity levels) as control (0), 0.5, 1.0, 2.0, and 4.0 units $cm^{-2}$ applied every two weeks. Application of laccase resulted in a decrease in thatch layer thickness for all treatments when compared to the control and there were no statistical differences among any of the treatments receiving laccase (FIG. 13A). This indicates that when laccase is applied biweekly, the rate of application to 0.5 units $cm^{-2}$ may be adequate. There was no perceived effect of different laccase applications on the organic matter content (Table 10). This may be attributed to a several possible reasons, with one being that the bentgrass green on which the study is conducted is a 20 year old green with high organic matter content within and below the thatch layer. So, a long term application of laccase may be needed to observe any significant differences. The second is the method in which organic matter was sampled and measured. The sample was collected for 0-2.5 and 2.5-5.0 cm depth. So, even if there is slight change in the organic matter content of the thatch layer due to application of laccase, it may be masked by very high organic matter content below the thatch layer. In the greenhouse studies, a significant decrease in organic matter content was observed with application of laccase (Sidhu et al., 2012, 2013a). This was because as the thatch layer thickness decreased with application of laccase, the top 2.5 cm core that was used for organic matter content extended to the sand layer below with low organic matter content when using a standard depth of sample. Thus an overall reduction in organic matter content was observed. Whereas, in the present field study, although that thatch layer thickness was decreased with laccase application, the sample depth did not extend to the underlying sand layer with low organic matter content. This was due to deeper thatch/mat layer with high organic matter content and, therefore, no differences in organic matter content were observed within the sample depth.

Three major components of plant cell walls are sugars, pectin, and lignin. In this study, the dry weight contents of only lignin and some major sugars we determined and expressed as a percentage of their sum. Therefore, a change in the content of one component inversely changed the percentage of the other. Total sugar content in thatch biomass was reduced with the application of high rates of laccase in year 1 (Table 11) and as a result the percent lignin content increased relative to that observed at lower rates of laccase application (FIGS. 15 and 16). Since structural sugar content did decrease with increased application rate of laccase, this suggests that application of laccase improved availability of sugars for microbial degradation.

Frequency of Application

Laccase at 2.0 units $cm^{-2}$ was applied once every 2, 4, 8, and 12 weeks to optimize the frequency of application. Thatch layer thickness decreased in comparison to control when laccase was applied regardless of frequency (FIG. 13B). All laccase frequencies of application were similar in year one, but the 2.0 (2) and 2.0 (4) frequencies exhibited the lowest TLT in year two, indicating that 2.0 units $cm^{-2}$ of laccase as infrequent as one application in four weeks is an effective frequency. A reduction in $L_S$ was observed in plots when laccase was applied at the different frequencies in comparison to control (FIG. 14B), while $L_I$ decreased only at the 2 and 4 week frequency (FIG. 25B). The contents of $L_S$ and $L_I$ tended to be higher at the 4 and 8 week frequencies relative to two week frequency. In year one, there was trend for total and individual sugar contents to decrease in the plots treated with laccase in comparison to the control plots, but this trend was especially apparent in year 2, indicating that laccase application modified the thatch biomass structure leading to increased decomposition by microbes (Table 11).

Influence of Cultural Management Practices

Organic matter content in the upper 2.5 cm ($OM_U$) was lower in plots receiving core aeration followed by sand topdressing (FIG. 17). This reduction in OM content may be attributed to the dilution of organic matter with sand. Application of laccase once in four weeks along with core aeration and sand topdressing did not further reduce organic matter when compared to plots with receiving only core-aeration and sand topdressing. Application of only laccase at 2.0 units $cm^{-2}$ once in 4 weeks was not as effective as core aeration and sand topdressing in reducing OM content (FIG. 17). When laccase was applied along with core aeration and sand topdressing, TLT was further reduced (FIG. 13C) as compared to the core aeration and sand topdressing treatment alone or laccase application alone. This may be attributed to the combination of 1) application of laccase which caused structural changes in thatch biomass and improved microbial decomposition and 2) the incorporation of sand which created a more favorable environment for microbial growth (Carrow et al., 1987). Core aeration and topdressing enhanced structural sugar loss and eventually led to an increase in lignin content of the remaining organic matter. Application of laccase in combination with core aeration and sand topdressing may lead to a reduction in the number of cultivations necessary to keep TLT at a desired level.

Design

The experimental design for this example included ten treatments in a completely randomized block design and a priori comparisons of groups of treatments were used to evaluate laccase rates, frequency of application, and influence of cultural management practices. This design did not allow determination of interaction effects among treatment groups (e.g., rates×frequency etc.). The information gained from this study has now been used to design a much smaller factorial experiment that should provide the minimum effect rate and frequency of laccase application.

Conclusions

The field research described in this Example demonstrated the efficacy of applications of laccase enzyme on physical and chemical composition properties of the thatch layer of creeping bentgrass turf over a wide range of activity levels and frequencies of application. Laccase application rate can be as low as 0.5 units $cm^{-2}$ when applied as biweekly applications and remain effective in reducing thatch layer accumulation. When laccase at 2.0 units $cm^{-2}$ is applied, the application frequency can be as infrequent as once a month. Laccase application at 2.0 units $cm^{-2}$ once in four weeks was just as effective at reducing TLT as was core aeration and sand topdressing twice per year. Even greater reductions in TLT were observed when laccase was applied in combination with core aeration and sand topdressing. This novel approach of direct application of a lignin degrading enzyme warrants further study to determine its potential as an effective and less disruptive means of thatch management for golf putting greens.

Tables for Example 5 appear on the following pages:

TABLE 9

Description of laccase treatments applied to creeping bentgrass

| Treatment No | Laccase activity level | Application frequency (wks) | Cultural Mgt. prct. | Designation |
|---|---|---|---|---|
| T1 Control | 0 | 2 | No | Control |
| Laccase Rates | | | | |
| T2 0.5 (2) | 0.5 | 2 | No | 0.5 (2) |
| T3 1.0 (2) | 1.0 | 2 | No | 1.0 (2) |
| T4 2.0 (2) | 2.0 | 2 | No | 2.0 (2) |
| T5 4.0 (2) | 4.0 | 2 | No | 4.0 (2) |
| Frequency of Appl. | | | | |
| T6 2.0 (4) | 2.0 | 4 | No | 2.0 (4) |
| T7 2.0 (8) | 2.0 | 8 | No | 2.0 (8) |
| T8 2.0 (12) | 2.0 | 12 | No | 2.0 (12) |
| Cultural Mgt. | | | | |
| T9 CMP | 0 | 2 | Yes | CMP |
| T10 CMP + 2.0 | 2.0 | 4 | Yes | CMP + 2.0 (4) |

TABLE 10

Analysis of variance (ANOVA) table showing the effects of laccase rates, frequency of application, and influence of cultural management practices on total organic matter ($OM_U$, 0-2.5 cm; $OM_L$, 2.5-5.0 cm; OM, 0-5.0 cm), thatch layer thickness (TLT), saturated hydraulic conductivity (SHC), acid-soluble lignin ($L_S$), acid-insoluble lignin ($L_I$), total lignin ($L_T$), glucose ($S_{GLU}$), xylose ($S_{XYL}$), galactose ($S_{GAL}$), arabinose ($S_{ARA}$), and total sugars ($S_T$) in creeping bentgrass.

| | df | $OM_U$ (0-2.5 cm) | $OM_L$ (2.5-5.0 cm) | OM (0-5.0 cm) | TLT | SHC | $L_S$ | $L_I$ |
|---|---|---|---|---|---|---|---|---|
| | | | | mean square value | | | | |
| Laccase Rates | | | | | | | | |
| Year (Y) | 1 | 12814* | 26 | 572 | 10 | 9 | 58** | 12362*** |
| Rep*Year (Error A) | 3 | 649 | 59 | 91 | 2 | 13** | 0.2 | 10 |
| Treatment (T) | 4 | 568 | 48 | 120 | 35*** | 4 | 152*** | 1749*** |
| Year*Treatment | 4 | 433 | 121 | 166 | 1 | 4 | 7 | 108** |
| Error B | 24 | 432 | 126 | 131 | 1 | 2 | 3 | 17 |
| Frequency of Appl. | | | | | | | | |
| Year (Y) | 1 | 9335 | 16 | 460 | 42* | 1 | 22*** | 15619*** |
| Rep*Year (Error A) | 3 | 1007 | 148 | 83247 | 2 | 7 | 1 | 7 |
| Treatment (T) | 4 | 656 | 65 | 137 | 38*** | 3 | 85** | 2098*** |
| Year*Treatment | 4 | 659 | 115 | 175 | 1 | 6 | 1 | 25 |
| Error B | 24 | 412 | 119 | 135 | 1 | 2 | 2 | 23 |
| Cultural Mgt. Practices | | | | | | | | |
| Year (Y) | 1 | 4364 | 13 | 205 | 1 | 3 | 19* | 14716*** |
| Rep*Year (Error A) | 3 | 479 | 163 | 173 | 3 | 119 | 1 | 7 |
| Treatment (T) | 3 | 4574** | 61 | 399 | 45*** | 225** | 66*** | 62240*** |
| Year*Treatment | 3 | 1551 | 153 | 332 | 10* | 5 | 2 | 137*** |
| Error B | 18 | 563 | 733 | 138 | 2 | 42 | 2 | 13 |

| | $L_T$ | $S_{GLU}$ | $S_{XYL}$ | $S_{GAL}$ | $S_{ARA}$ | $S_T$ |
|---|---|---|---|---|---|---|
| | | | mean square value | | | |
| Laccase Rates | | | | | | |
| Year (Y) | 14123*** | 10822 | 4248 | 570* | 3450* | 58586 |
| Rep*Year (Error A) | 12 | 770 | 1596*** | 7 | 84 | 6448* |
| Treatment (T) | 2110*** | 1334* | 530** | 107* | 65 | 5826* |
| Year*Treatment | 112** | 646 | 144 | 12 | 55 | 1543 |
| Error B | 21 | 316 | 106 | 29 | 42 | 1108 |

TABLE 10-continued

Analysis of variance (ANOVA) table showing the effects of laccase rates, frequency of application, and influence of cultural management practices on total organic matter ($OM_U$, 0-2.5 cm; $OM_L$, 2.5-5.0 cm; OM, 0-5.0 cm), thatch layer thickness (TLT), saturated hydraulic conductivity (SHC), acid-soluble lignin ($L_S$), acid-insoluble lignin ($L_I$), total lignin ($L_T$), glucose ($S_{GLU}$), xylose ($S_{XYL}$), galactose ($S_{GAL}$), arabinose ($S_{ARA}$), and total sugars ($S_T$) in creeping bentgrass.

| Frequency of Appl. | | | | | | |
|---|---|---|---|---|---|---|
| Year (Y) | 16838*** | 14073 | 5043 | 761* | 3495* | 73049* |
| Rep*Year (Error A) | 11 | 931 | 947*** | 36 | 123* | 2908 |
| Treatment (T) | 2776*** | 1201* | 599*** | 126** | 73 | 5778** |
| Year*Treatment | 24 | 669 | 366* | 73* | 181** | 3076* |
| Error B | 28 | 279 | 94 | 22 | 30 | 915 |
| Cultural Mgt. Practices | | | | | | |
| Year (Y) | 15809*** | 11900* | 5741 | 950* | 4107* | 75597* |
| Rep*Year (Error A) | 7 | 615 | 803** | 13 | 143* | 3045 |
| Treatment (T) | 82608*** | 2225* | 695** | 219* | 76 | 9484** |
| Year*Treatment | 107** | 615 | 478* | 86* | 147* | 4221 |
| Error B | 14 | 496 | 120 | 21 | 22 | 1443 |

*Significant at the 0.05 probability level
**Significant at the 0.01 probability level
***Significant at the 0.001 probability level

TABLE 11

Effect of laccase rates, frequency of application, and influence of cultural management practices on extractive-free glucose ($S_{GLU}$), xylose ($S_{XYL}$), galactose ($S_{GAL}$), and total sugar content ($S_T$) after six months of treatment application.

| Treatment group | Glucose $S_{GLU}$ | | Xylose $S_{XYL}$ | | Galactose $S_{GAL}$ | | Total Sugars $S_T$ | |
|---|---|---|---|---|---|---|---|---|
| | Year 1 | Year 2 | Year 1 | Year 2 | Year 1 | Year 2 | Year 1 | Year 2 |
| | | | | mg · g$^{-1}$ | | | | |
| Laccase Rates | | | | | | | | |
| Control | 245a† | 229a | 153a | 141a | 75a | 69a | 547a | 492a |
| 0.5 (2) | 233ab | 187b | 148ab | 117b | 66bc | 63a | 520ab | 414b |
| 1.0 (2) | 228bc | 173b | 140b | 108b | 69b | 61a | 505bc | 387b |
| 2.0 (2) | 246a | 189b | 138b | 116b | 67bc | 60a | 511abc | 414b |
| 4.0 (2) | 218c | 197ab | 137b | 122b | 63c | 60a | 478c | 427b |
| Frequency of Application | | | | | | | | |
| Control | 245a | 229a | 153a | 141a | 75a | 69a | 547a | 492a |
| 2.0 (2) | 246a | 189b | 138bc | 116b | 67bc | 60b | 511bc | 414b |
| 2.0 (4) | 232a | 170b | 152a | 102b | 72ab | 52b | 533ab | 365b |
| 2.0 (8) | 237a | 187b | 132c | 114b | 63c | 61ab | 495c | 412b |
| 2.0 (12) | 226a | 197b | 141b | 114b | 68b | 61ab | 499c | 416b |
| Cultural Mgt. Practices | | | | | | | | |
| Control | 245a | 229a | 153a | 141a | 75a | 69a | 547a | 492a |
| CMP | 232ab | 195ab | 143b | 121ab | 64b | 59b | 504bc | 424ab |
| 2.0 (4) | 232ab | 170b | 152a | 102b | 72a | 52b | 533ab | 365b |
| CMP + 2.0 (4) | 215b | 179b | 133c | 144b | 62b | 56b | 474c | 395b |

†Means in a column in a treatment group followed by the same lowercase letter are not sig. different according to LSD at α = 0.05

Example 6

Residual Effect Field Study

Organic layer formation in the form of thatch is a major problem in turf management systems. The field studies described in Examples 4 and 5 above demonstrated that bi-weekly application of laccase enzyme facilitates the degradation of thatch layer and reduce the rate of accumulation of organic matter in "Crenshaw" creeping bentgrass (*Agrostis stolonifera* L.), bermudagrass, and zoysiagrass. In this example, a field experiment on creeping bentgrass was conducted to observe the residual effect of laccase application on organic matter degradation after ceasing laccase application. The major objectives of this study were 1) to determine the residual effects of laccase application on physical and chemical properties of thatch layer and 2) to compare residual effects of laccase with and without repeated applications.

Materials & Methods

A field experiment was conducted on "Crenshaw" creeping bentgrass (*Agrostis stolonifera* L.) (Engelke et al., 1995) at The University of Georgia, Griffin Campus as an 18 month study from July 2010 to January 2012. The bentgrass green was established as a sand based putting green on 90:10 sand and organic matter mix (Michigan Peat) as per USGA recommendations (USGA Green Section Staff, 1973). Fertilizer applications for 2010 and 2011 consisted of 50 kg ha$^{-1}$ granular fertilizer 24-4-10 (N—P$_2$O$_5$—K$_2$O) (Lesco. Strongsville, Ohio) in the third week of March, September, and October and 2 kg ha$^{-1}$ soluble 20-20-20 fertilizer (JR Peters Inc, Allentown, Pa.) every two weeks starting third week of April thru September. Bentgrass plots were mowed three times a week by Toro Greensmaster 3100 (The Toro Company, Bloomington, Minn.) and maintained at a height of 0.42 cm.

The experiment was conducted on plots (30.5 cm×61.0 cm) with 12 treatments replicated four times in a completely randomized block design. A priori comparisons of groups of treatments from the experiment were used to evaluate: rate of application; frequency of application; influence of cultural management practices (core aeration and topdressing); and sources of laccase (Table 12). Laccase was applied for six months from July 2010 to December 2010 for treatments T1 to T12. Laccase application was repeated only for treatment T11 from July 2011 to December 2011 (Table 12). All plots were sampled at 6, 12, and 18 months after treatment initiation or 0, 6 and 12 months after the end of the initial treatment application period to observe the residual effects of laccase application. Laccase treatments were applied as 410 mL solution at different rates and frequencies (Table 1). Laccase enzyme from *Trametes versicolor*, a white-rot fungus, was purchased from Sigma-Aldrich (product 53739, Sigma Aldrich Inc., St. Louis, Mo.) and was applied at activity levels of 0 (control), 0.5, 1.0, 2.0 and 4.0 units cm$^{-2}$ applied every two weeks and laccase activity level 2.0 units cm$^{-2}$ applied every 2, 4, 8, and 12 weeks to optimize the rate and frequency of laccase application. Plots receiving cultural management treatments were core-aerated and sand topdressed twice yearly in April and September. Core aeration was accomplished using a Ryan Greensaire 24 Aerator (Ryan Inc. Johnson Creek, Wis.) fitted with 1.27 cm tines on a spacing of 5.0×5.0 cm and adjusted to penetrate to a depth of 6.25 cm. Immediately following core aeration, sand topdressing with 1134 g of sand (Quikrete Premium Play Sand) per plot was accomplished using a Scotts Precision Green Spreader. Laccase was applied at 2.0 units cm$^{-2}$ every 4 weeks on plots core-aerated and sand topdressed twice a year to observe the effectiveness of laccase in combination with the cultural management practice. Hereafter, rate/frequency treatments are presented as the rate of the laccase activity level followed by the frequency of application in parenthesis e.g., "2.0 (4)" denotes treatments receiving laccase with an activity of 2.0 units cm$^{-2}$ applied at 4 weeks (Table 12).

Laccase from two different sources were compared for their effectiveness on thatch management. Laccase from *Pycoporus* genus was procured from Jiangnan University, China (CHU (2)) and from a commercial industrial wholesale supplier in China (CHI (2)) and was applied at activity level of 2.0 units cm$^{-2}$ every two weeks (Table 1). The treatment CHU (2) (i.e. T12) was applied from July 2010 to December 2010 and from July 2011 to December 2011 to compare the effect of continued application of laccase every year for six months to the residual effect of one six month period of laccase application (Table 12).

Measurements

The residual effect of laccase application on physical and chemical properties of thatch layer was determined at 6, 12, and 18 months after initiation of treatment application. Variables measured included total organic matter content for a depth of 0-2.5 cm (OM$_U$), 2.5-5.0 cm (OM$_L$), and 0-5.0 cm (OM), thatch layer thickness (TLT), and saturated hydraulic conductivity (SHC). Similarly, extractive-free acid-soluble lignin (L$_S$) and acid-insoluble lignin (L$_I$) content was determined to observe the impact of treatment application on chemical composition properties of thatch layer biomass. Total lignin content (L$_T$) was calculated by addition of L$_S$ and L$_I$ contents.

Laccase activity assay, organic matter content (OM), saturated hydraulic conductivity (SHC), thatch layer thickness (TLT), and extractive-free lignin content (soluble (L$_S$) and insoluble (L$_I$)) were conducted as described in Example 4, above.

Statistical Analysis

A repeated measures design was used to analyze the full model for laccase residual effect, consisting of eleven treatments, three levels of treatment duration and four replications. Treatment CHU (e.g., T12) was repeated from July to December 2011 and is not considered in the full model. Treatments were combined together to form: a) a rate of application group [control, 0.5 (2), 1.0 (2), 2.0 (2), and 4.0 (2)]; b) an application frequency group [control, 2.0 (2), 2.0 (4), 2.0 (8), and 2.0 (12)]; c) a cultural management group [control, 2.0 (2), CMC, and CMC+2.0 (4)]; d) a laccase sources group [2.0 (2), CHU (2), and CHI (2)]; and e) two year application group [2.0 (2) and CHU (2)]. Analysis of variance (ANOVA) was performed to evaluate the main effects of treatment duration, treatments, and interaction effects of duration and treatment using general linear model (GLM) (SAS Institute, 1994). Treatments were grouped together in five groups and analyzed as repeated measures to evaluate the effects of treatment, treatment duration, and the interaction effects of treatment and treatment duration. Fisher's protected LSD test with α=0.05 was used for determining statistical differences among durations and treatment means following each ANOVA.

Results

Full Model

Strong treatment effects were observed for OM$_U$ (P≤0.01), TLT (P≤0.001), SHC (P≤0.001), L$_I$ (P≤0.001), and L$_T$ (P≤0.01) (Table 13). Strong duration (time after treatment applications were initiated) effects (P≤0.001) were observed for OM$_U$, TLT and all lignin content measurements (Table 13) indicating residual effect of laccase application on these parameters. No duration effects were observed for SHC and OM$_L$. Interaction effects of duration by treatment (P 0.001) were observed for L and L$_T$ indicating that different treatments had different effects on extractive-free acid-insoluble and total lignin.

Rate of Application

Rate of laccase application significantly effected (P≤0.001) TLT, L$_I$, and L$_T$ (Table 13). Strong duration effects were observed for OM$_U$ (P≤0.001), TLT (P≤0.001), L$_S$ (P≤0.01), L$_I$ (P≤0.001), and L$_T$ (P≤0.001) (Table 13). Interaction effects (P≤0.001) of duration by treatment were observed for L$_I$ and L$_T$ content. After six months of treatment, no differences were observed for OM$_U$, OM$_L$, and OM in any of the treatments. Samples taken at 12 months after treatment initiation showed OM$_U$ at laccase activity level of 4.0 units cm$^{-2}$ decreased by 21.5 mg·g$^{-1}$ when compared to control (Table 14). No differences were observed for OM$_L$ and OM for 12 month sampling. Samples taken at 18 months after the start of experiment showed a 10.4 mg·g$^{-1}$ increase in OM content in plots treated with 1.0 (2) compared to control plots. Organic matter content (0-2.5 cm) increased by 19.5 mg·g$^{-1}$ at 0.5 units cm$^{-2}$ when sampled between 6 and 18 months after treatment initiation. A significant reduction of 6.2 and 8.0 mg·g$^{-1}$ in OM$_L$ content from 6 to 18 months for treatments 2.0 (2) and 4.0 (2), respectively was observed and reduction of OM (8.5 mg·g$^{-1}$) from 6 to 12 months was observed for treatment 4.0 (2) suggesting the residual effect of laccase.

Figure 19A:
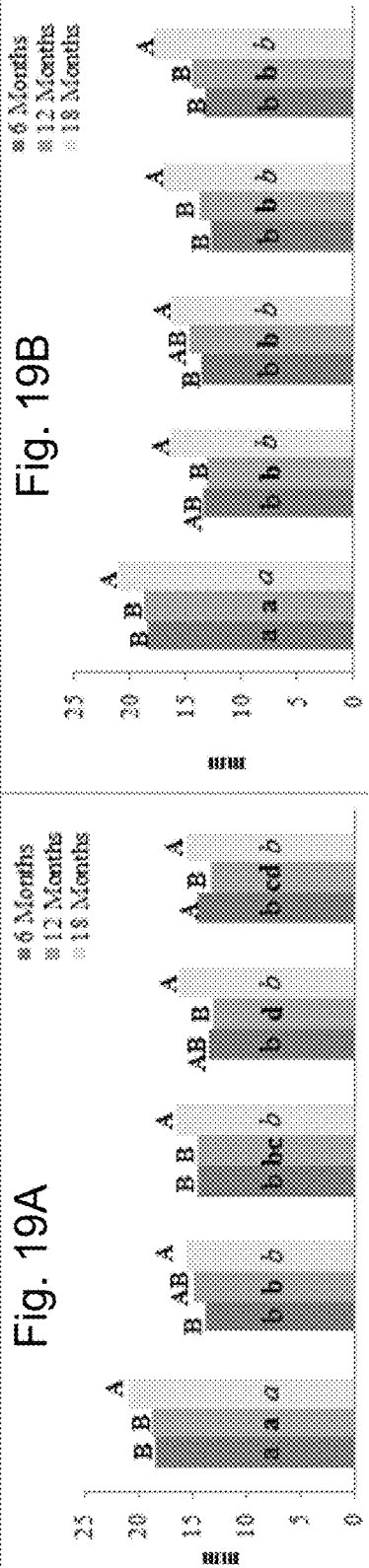
FIGS. 19A-19D illustrate thatch layer thickness (TLT) in mm at 6, 12, and 18 months after treatment initiation on creeping bentgrass with rate of laccase application (1A); frequency of application of laccase (FIG. 1B); cultural management and laccase treatments (FIG. 1C); and laccase sources (FIG. 1D). The stacked bars in FIG. 1C represent depth of thatch layer and sand deposition on plots from topdressing. Values are means of four replicates. Same letter within the bars (6 months=lowercase standard, 12 months=lowercase bold, and 18 months=lowercase italics) and same letter on top of the bars (duration effect=uppercase bolded) are not considered to be statistically different according to Fisher's protected LSD at α=0.05.

Laccase treatments at different activity levels were equally effective and after six months of treatment application lowered TLT by 3.8 to 4.8 mm in comparison to the control (FIG. 19A). Twelve months after start of the treatment, TLT was lowered by all activity levels of laccase. However, plots treated with laccase at activity levels of 2.0 and 4.0 units cm$^{-2}$ showed significant reduction in thatch layer thickness in comparison to control plots and plots treated with 0.5 and 1.0 units cm$^{-2}$ laccase activity. A reduction in TLT was observed for all treatments in comparison to control when sampled 18 months after initiation of treatments. Application of laccase at 0.5, 1.0, and 2.0 units cm$^{-2}$ was effective in maintaining the TLT up to six months after treatment completion; whereas in plots treated with laccase at 4.0 units cm$^{-2}$, TLT was lowered from 14.5 mm six months after treatment initiation to 13.3 mm 12 months after initiation of treatments. An increase in TLT occurred when laccase was applied at 0.5 and 1.0 units cm$^{-2}$ over the three sampling dates.

Laccase activity levels did not appear to effect SHC at any of the sampling dates (Table 15). After six months of treatment, laccase application up to 2.0 units cm$^{-2}$ lowered L$_S$ by 7.8 to 8.9 mg·g$^{-1}$ when compared to control plots (Table 15). Acid-soluble lignin in plots treated with 4.0 cm$^{-2}$ laccase activity was reduced by 12.2 mg·g$^{-1}$ when compared to control plots at the end of treatment (six months) (Table 15). No differences in L$_S$ were observed at sampling times of 12 and 18 months after treatment initiation.

Extractive-free L$_I$ content was lowered in comparison to control plots when treated with laccase up to 2.0 and 1.0 units cm$^{-2}$ at 6 and 12 months after initiating treatments, respectively (Table 15). At the end of the treatment application, L$_I$ was higher in plots treated with 4.0 units cm$^{-2}$ when compared to control. Similarly, in samples taken 12 months after treatment initiation, L$_I$ content was higher than control plots when treated with 2.0 and 4.0 units cm$^{-2}$ laccase activity suggesting residual effects of laccase. Plots treated with laccase showed higher L$_I$ content compared to control plots at 18 months after treatment initiation (Table 15). An increase in the L$_I$ content was observed in all the treatments (Table 15). Variation in L$_T$ content followed similar trends as for L$_I$ content with different laccase activity levels (FIG. 20A).

Frequency of Application

Laccase application frequency effects (P≤0.001) were observed for TLT, L$_I$, and L$_T$ (Table 13). Strong duration effects (P≤0.001) were observed for OM$_U$, TLT, and L$_T$ content (Table 13). Interaction effects of duration by treatment were observed for L$_I$ (P≤0.001) and L$_T$ (P≤0.001) (Table 13). No differences in OM$_U$, OM$_L$, and OM were observed between plots treated with laccase and control plots 6 and 12 months after treatment initiation. However, an increase in OM$_U$ and OM content was noted in plots treated with 2.0 (12) over control plots at 18 months after start of treatment application. An accumulation of 52.3 mg·g$^{-1}$ in OM$_U$ was obtained in plots treated with 2.0 (12) between the between 6 and 18 months of sampling dates (Table 14).

Figure 19B:
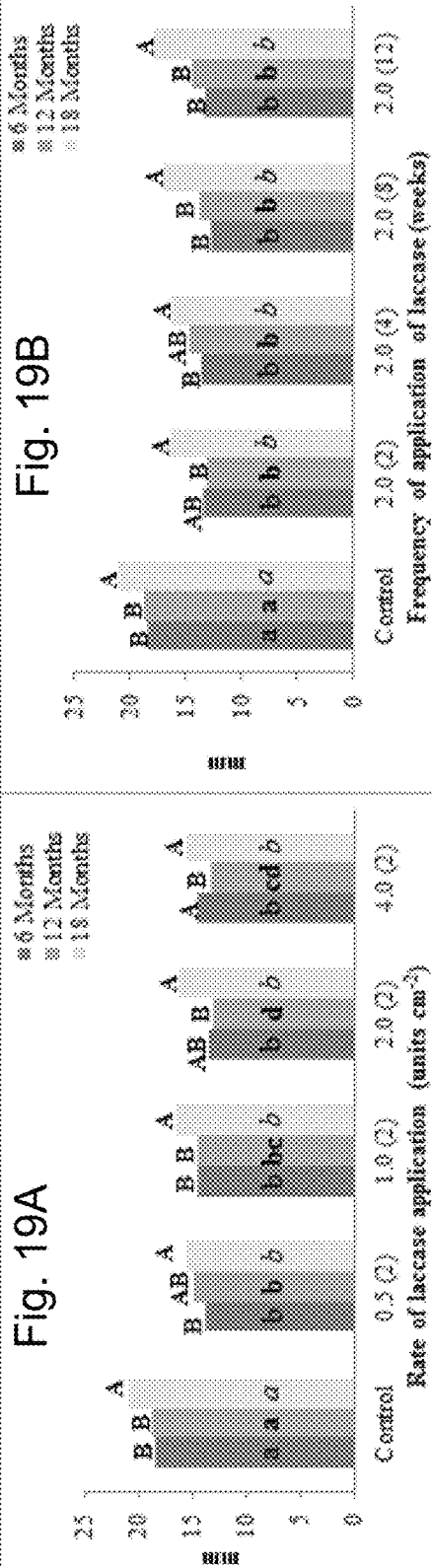

Thatch layer thickness was lowered by 4.7 to 5.6 mm, 4.1 to 5.6 mm, and 3 to 4.8 mm in plots treated with laccase at different frequencies in comparison to control plots when sampled at 6, 12, and 18 months, respectively (FIG. 19B).

No differences among different application frequencies were observed at any sampling date. An increase in thatch layer thickness was observed in all treatments at 18 months sampling when compared to TLT after six months of treatment. No significant change in TLT was observed at 12 months sampling (FIG. 19B).

All laccase treatments were effective in lowering the L$_S$ content when compared to control six months after treatment initiation (Table 15). However, the decrease in L$_S$ content in comparison to control was more with the 2.0 (2) treatment than the 2.0 (8) and 2.0 (12) treatments (Table 15). This suggests that frequent application of laccase was more effective in lowering L$_S$ content in comparison to the untreated control. No differences in L$_S$ values were observed when sampled at 12 and 18 months after starting the experiment. After six months of treatment, a reduction in L$_I$ content was observed in plots receiving laccase treatments at every 2 (29.6 mg·g$^{-1}$) and 4 (15.5 mg·g$^{-1}$) weeks when compared to control (Table 15). The L$_I$ content increased by 5.8 mg·g$^{-1}$ in plots receiving 2.0 (12) treatment when compared to the control plots. Sampling after 12 months indicated an increase in L$_I$ content when laccase was applied every 2, 8, and 12 weeks. However, with application of laccase every four weeks, a slight reduction in L$_I$ content was observed at 12 months sampling in comparison to the control. All laccase treated plots showed an increase in L$_I$ content in comparison to control plots when sampled at 18 months (Table 15). A significant increase in L$_I$ content was observed in all the treatments when sampled over time (Table 15). Similar trends were observed for L$_T$ content with laccase application at different frequencies (FIG. 20B).

Cultural Management

The cultural management treatment group showed treatment effects for OM$_U$ (P≤0.05), TLT (P≤0.001), SHC (P≤0.05) and L$_I$ (P≤0.001) and L$_T$ (Table 13). Significant duration effects were observed for organic matter content (0-2.5 cm, 2.5-5.0 cm, and 0-5.0 cm), TLT, and L$_S$, L$_I$, L$_T$ extractive-free lignin content. Duration by treatment interaction effects (P≤0.001) were observed for L$_I$ and L$_T$ (Table 13).

Figure 19C:
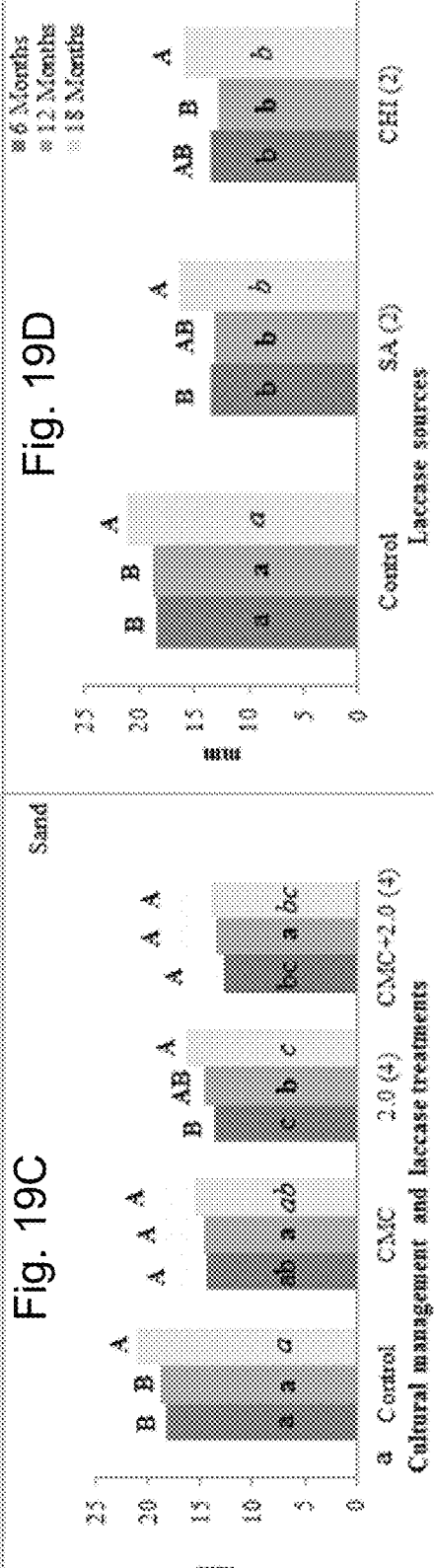

In comparison to control, no differences were observed for OM$_U$, OM$_L$, and OM content at six months after treatment initiation (Table 14). When plots were sampled 12 months after treatment initiation, OM$_U$ content decreased by 50 and 40.7 mg·g$^{-1}$ in plots treated with CMC and CMC+2.0 (4), respectively, when compared to control plots. Significant duration effects were observed for OM$_L$ and OM content, which is evident from a slight increase of 18.4 and 18.7 mg·g$^{-1}$ in OM$_L$ and OM content in comparison to control when sampled after 18 months of treatment initiation (Table 14). No duration effect was observed for OM$_U$ (Table 14). After six months, TLT decreased from 18.3 mm in control plots to 13.6 and 15.7 mm in plots treated with 2.0 (4) and CMC+2.0 (4) treatments, respectively (FIG. 19C). Measurement of thatch layer from plots receiving core aeration and sand topdressing had 3 to 4 mm of sand additions and this was included in the calculations. A TLT reduction of 4.1 mm was observed in plots treated with 2.0 (4) when compared to control plots when sampled at 12 months after start of experiment. At 18 months sampling, TLT was reduced from 21.0 mm in control plots to 16.2 and 17.9 mm in plots receiving 2.0 (4) and CMC+2.0 (4) treatment, respectively (FIG. 19C). Significant duration effects were observed for control and laccase treatment 2.0 (4) for TLT, and no duration effects were observed for plots receiving cultural management practices (FIG. 19C).

After six months of treatment application, plots receiving core aeration and sand topdressing treatment showed an increase of 13.5 cm h$^{-1}$ in SHC in comparison to control plots (Table 15). Plots receiving laccase treatment with or without cultural management had no differences in SHC when compared to control plots (Table 15). No change in SHC was observed in comparison to control at other sampling durations. No duration effect was recorded for SHC in this group of treatments (Table 15). A reduction of 3.6, 7.8, and 3.8 mg·g$^{-1}$ $L_S$ content was recorded in plots treated with CMC, 2.0 (4), and CMC+2.0 (4), respectively when compared to control plots at six months sampling. However, no differences in $L_S$ content were observed at sampling after 12 and 18 months of treatment initiation. A slight but significant duration effect was observed for $L_S$ content in 2.0 (4) treatment (Table 15). Extractive-free Land $L_T$ content after six months of treatment application was lowered in plots treated with laccase treatment alone and increased in plots treated with CMC and CMC+2.0 (4) treatment when compared to control plots (Table 15, FIG. 20C). A similar trend was recorded for $L_I$ at sampling conducted at 12 months after treatment initiation. Acid-insoluble content of all plots receiving treatments increased over the control at 18 months after treatment initiation. Significant duration effects were observed for $L_I$ and $L_T$ with increases in lignin content occurring in all the treatments over time (Table 15, FIG. 20C).

Sources of Laccase Enzyme

Laccase enzymes procured from different sources were similarly effective on organic matter ($OM_U$, $OM_L$, and OM; Table 14), TLT (FIG. 19D), and SHC (Table 15). Slight differences in $L_S$ and $L_I$ content were observed in plots treated with laccase from different sources (Table 15). Six months after treatment initiation, $L_S$ content was lower in plots receiving 2.0 (2) in comparison to other two laccase enzymes. Samples taken at 12 and 18 months showed no differences in $L_S$ content in plots treated with different laccase enzymes. When treated with CHI (2) for six months, $L_I$ content was slightly higher than the other two laccase enzymes. However, when sampled after 12 months, $L_I$ content was higher in plots treated with 2.0 (2) followed by CHI (2) and CHU (2). No differences in $L_S$ and $L_I$ content were observed in plots receiving different laccase sources at six months after start of treatment (Table 15). A significant increase in $L_I$ and $L_T$ content occurred between 6 and 18-month samples (Table 15, FIG. 20D).

Application Duration

Figure 21:
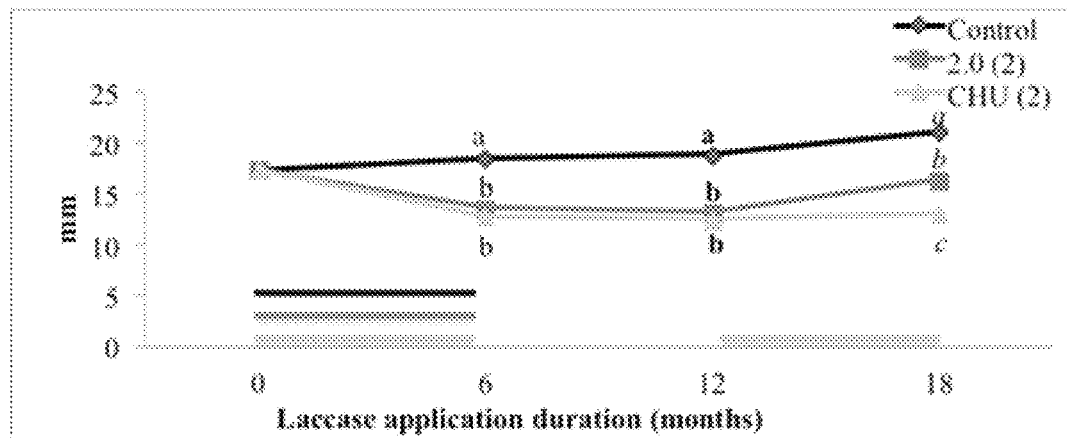
FIG. 21 illustrates Thatch layer thickness (TLT) in mm at 6, 12, and 18 months after treatment initiation on creeping bentgrass with laccase treatments 0 (control), and 2.0 (2) for six months in year one, CHU (2) for six months in year one and six months in year two. Horizontal lines near the bottom of the graph represent periods of treatment application from 0-6 months and 12-18 months. Values are means of four replicates. Same letter within treatment (6 months=lowercase standard, 12 months=lowercase bold, and 18 months=lowercase italics) are not considered to be statistically different according to Fisher's protected LSD at α=0.05.
Figure 22:
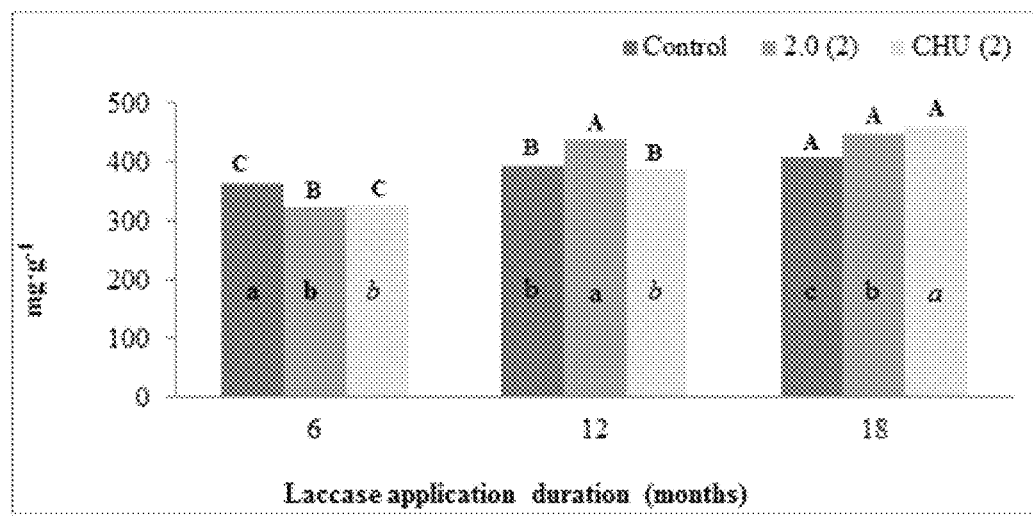
FIG. 22 illustrates extractive-free total lignin content ($L_T$) in mg·g$^{-1}$ at 6, 12, and 18 months after treatment initiation on creeping bentgrass with laccase treatments 0 (control), and 2.0 (2) for six months in year one, CHU (2) for six months in year one and six months in year two. Values are means of four replicates. Same letter within treatment (control=lowercase standard, 2.0 (2)=lowercase bold, and CHU (2)=lowercase italics) and same letter on top of the bars (duration effect=uppercase bolded) are not considered to be statistically different according to Fisher's protected LSD at α=0.05.

Strong effects of laccase application duration were observed for OM, TLT and $L_T$ in samples taken 18 months after treatment initiation (Table 14, Table 15, and FIG. 21). An increase in organic matter was observed 18 months after treatment initiation for treatment CHU (2), which was applied for six months in year one and six months in year two, in comparison to application of laccase 2.0 (2) applied for only six months in year one (Table 14). The baseline measurement for TLT was 17.2 mm. The TLT of control plots continued to increase with time, whereas in plots treated with 2.0 (2) and CHU (2) TLT was significantly reduced after six months. When sampled 12 months after treatment initiation, TLT was slightly lower than when sampled after six months in both the treatments. When sampled after 18 months, TLT in plots treated with 2.0 (2) was 3.3 mm higher than plots treated with CHU (2) (FIG. 21). Lignin content after 18 months was slightly higher in both the treatments when compared to the control (FIG. 22).

Discussion

Non-destructive methods to manage thatch are desired but have often been shown to be ineffective. One of the possible reasons that past studies found these products to be inconsistent in organic matter decomposition is that they focused on degradation of cellulosic and hemicellulosic sugars instead of lignin. The focus of the approach of the present example is to at least partially degrade the lignin protective matrix to open the biomass structure and increase access to readily decomposable structural carbohydrates.

By using laccase enzyme, turfgrass managers may have a new means to effectively manage thatch over wide range of environmental conditions and improve their ability to effectively utilize existing populations of soil microbes for the microbial decomposition of organic matter. In the examples above, reduction in thatch/mat layer by laccase treatment was demonstrated in greenhouse and field research (Sidhu et al., 2012; Sidhu et al., 2014). However, the present example addresses any residual effects of laccase treatment.

Laccase Rate and Frequency

Laccase treatments at different rates and frequency of application were initially ineffective in reducing $OM_U$, $OM_L$, and OM content after six months of application (Table 14). However, when laccase was applied at 4.0 units cm$^{-2}$ every two weeks, a significant reduction in $OM_U$ occurred at 12 months after treatment initiation (Table 14). This observation indicates that laccase application for six months continued to slow accumulation of $OM_U$ for over the next six months. As the time progressed from 12 to 18 months after initiation of treatments, the residual effect of laccase declined and $OM_U$ values began to increase in the treated plots in a similar manner to the control plots. A reduction in $OM_L$ content was observed over the 18-month sampling period in plots treated with 2.0 and 4.0 units cm$^{-2}$ (Table 14). Thus, continued application of laccase at a rate of about 2.0 to 4.0 units cm$^{-2}$ may be effective in lowering organic matter content in older turf greens that contain high organic matter content in the thatch/mat layer.

Laccase applied at all frequencies and rates were effective in lowering TLT in comparison to control plots after six months of treatment (FIG. 19A, 19B). Additionally, TLT readings from plots treated with the various laccase rates and frequencies for six months were lower relative to the control plots even after 12 and 18 months suggesting strong residual effects of laccase (FIG. 19A). However, TLT readings increased significantly at the three highest laccase rates between samplings at 12 and 18 months after treatment initiation suggesting that the residual effect of laccase in thatch layer was effective for about six months after treatment cessation (FIG. 19A). While laccase treatments did reduce TLT, there were only minor differences in SHC with no apparent trends (Table 15).

In the sub-study involving laccase application for six months in year one and again for six months in year two, a significant reduction in thatch layer was observed in comparison to plots receiving laccase for six months in year one when sampled at 18 months after treatment initiation (FIG. 21). Residual effect of laccase, after treatment cessation, reduced thatch layer buildup during the next six months. But a significant increase in thatch layer was observed when no laccase enzyme application was performed during second year. However, no thatch buildup was observed when laccase was applied for second year suggesting that annual applications of laccase enzyme for six months during the summer was effective in reducing or stabilizing thatch accumulation. No further reduction in thatch layer was observed during the second year even with application of laccase. Increase in $OM_U$ was observed in plots where laccase was applied for six months during second year when compared to laccase applied for six months in year one (Table 14). This may be attributed to tight stacking of thatch biomass due to removal of lignin bonds, reduction of structural sugars leading to weak thatch biomass.

Extractive-free $L_S$ content initially decreased with application of laccase as was evident from sampling conducted after the conclusion of treatments at six months (Table 15). The extent of reduction at six months was dependent on the amount of laccase applied to the plots based on rate and frequency of applications. Application of laccase up to 2.0 units $cm^{-2}$ decreased $L_I$ in thatch biomass, but application of laccase at 4.0 units $cm^{-2}$ showed an increase in $L_I$ content expressed as a proportion of the sample on a dry weight basis when compared to the control (Table 15). The increase in $L_I$ content could be attributed to the loss of excessive structural sugars in plots treated with laccase at 4.0 units $cm^{-2}$ (Sidhu et al., 2014). Three major components of plant biomass are cellulosic sugars, hemicellulosic sugars, and lignin. So, with application of laccase, lignin bonds are broken which leads to opening of the biomass structure making sugars more available for microbial decomposition. As the sugar content is decreased, the lignin content increases since it is expressed as the proportion of the total dry weight. A decrease in structural carbohydrate (cellulosic and hemicellulosic sugars) content in thatch biomass after laccase treatment was previously reported by Sidhu et al. (2013a, 2014). A decrease in structural sugar content was observed as the rate of laccase activity increased indicating more availability of sugars for microbial degradation (Sidhu et al., 2014). Residual effects of laccase applications were observed between the 6 and 18-month sampling dates as in the proportion of lignin present in thatch biomass. Lignin continued to accumulate during this period suggesting the continued loss of sugar content from the biomass even after laccase treatments had ceased (Table 15). $L_I$ constitutes the major component of $L_T$, and a similar trend in $L_T$ was observed with increasing laccase application rates (FIG. 20A). A maximum reduction for $L_S$, $L_I$ and $L_T$, was observed at six months when laccase was applied every two weeks. The extent of this reduction decreased with decreased frequency of laccase application (Table 15, FIG. 20B) suggesting the extent of lignin reduction was dependent on the amount of laccase applied to the plots.

Cultural Management and Laccase

Previous research related to the use of several different management techniques as a means to reduce thatch layer thickness and the accumulation of organic matter has shown contrasting results, as described above. It has been suggested that application of sand topdressing improves the microenvironment for microbial growth (Ledeboer and Skogly, 1967). However, some researchers believe that the dilution of organic matter in the thatch layer is the primary influence of sand topdressing (Couillard et al., 1997; Rieki, 1994). Topdressing alone had no effect on water infiltration rates (McCarty et al., 2007).

A 10% reduction in thatch layer thickness was reported by core aeration four times annually on creeping bentgrass (McCarty et al., 2007) and three to six times a year on Tifgreen bermudagrass (McWhirter and Ward, 1976). Carrow et al. (1987) noted no effect of core aeration applied once or twice a year on Tifway bermudagrass on thatch-mat depth although a reduction in stand density was observed. Several studies have reported an increase in water infiltration in turfgrass field after core aeration due to formation of water channels and porous profile (Bunnell et al., 2001; Canaway et al., 1986; McCarty et al., 2005).

In the present study, organic matter content in the top 2.5 cm was lower at 12 months with cultural management practice when compared to the control. This may be attributed to the dilution effect created by sand topdressing on the surface layer as sand topdressing showed no effect on organic matter at 2.5-5.0 cm depth (Table 14). The increase in $OM_L$ (18 months) and OM (12 and 18 months) for laccase treated thatch may be related to a more dense thatch biomass occurring from laccase activity on cellulose and hemicellulose sugars resulting in a higher content of $L_T$ as seen at 18 months (FIG. 20C). As raw organic matter decomposes, such as in composting situations, the resulting material increases in lignin content and density.

Lignin dynamics were also apparent in TLT results, where application of laccase along with cultural management effectively decreased TLT at 6 and 18 months and increased $L_T$ content at all three sampling times (FIG. 19C, 20C). The increase in $L_T$ may be attributed to the change in thatch biomass structure caused by laccase, making structural sugars more available for decomposition and a better microclimate for microbial growth due to core aeration and sand topdressing. Increased loss of structural sugars from thatch biomass may be responsible for elevated levels of lignin in the remaining thatch material. A significant loss in structural sugars of creeping bentgrass thatch biomass was also observed with application of laccase in greenhouse and field studies (Sidhu et al., 2013a, 2014).

Saturated hydraulic conductivity was higher at six months in plots that received only CMC (Table 15). At 18 months, SHC was higher when laccase was applied in combination with CMC, when compared to control plots as well as plots receiving only laccase treatments. The increase in SHC may be attributed to the core aeration, which creates channels for rapid water movement. The laccase-CMC data illustrated that the 2.0 (4) treatment of laccase was effective in reducing TLT at 6, 12, and 18 months, when applied alone or with CMC. Laccase alone did not influence SHC, but in combination with CMC, SHC increased relative to the control. These results suggest that laccase has positive effects on the management of thatch and can be used in conjunction with routine CMC.

Laccase Source

Figure 19D:
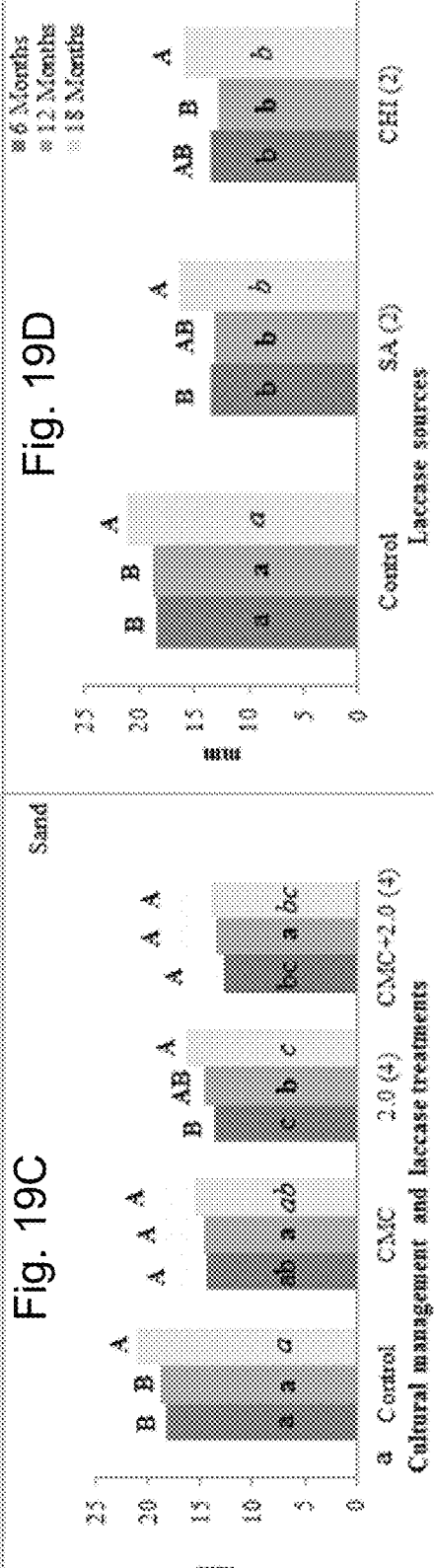

Different sources of laccase enzymes proved equally effective in reducing thatch layer thickness (FIG. 19D). However, slight differences in $L_S$ and $L_I$ were observed with different laccase sources (Table 15). Lignin content ($L_S$ and $L_I$) was significantly lower in plots treated with laccase procured from Sigma Aldrich in comparison to plots treated with CHU and CHI after six months of application, but no differences were observed in lignin content when sampled at 12 and 18 months after treatment initiation (Table 15). This suggests that laccase from Sigma Aldrich was initially more effective but the other laccase sources proved to be equally effective in reducing on thatch biomass over time.

Conclusion

This field research demonstrated the residual effects of laccase enzyme on creeping bentgrass with TLT reduced by an average of 23.5, 25.7, and 23.9% across all laccase rates for 6, 12, and 18 month sampling times, respectively (FIG. 19A). Similarly, the average TLT reductions across all frequencies of laccase applications were 27.8, 25.5, and 19.7% of the control for 6, 12, and 18 month samplings, respectively (FIG. 19B). Organic matter contents were not appreciably affected by laccase rates or frequency at any of the three sample dates. Total lignin content increased over time, suggesting decomposition of cellulose and hemicellulose fractions resulted in a concentration of lignin. Therefore, the total OM may not change but the composition did over time. The 2.0 (4) treatment of laccase was effective in reducing TLT at 6, 12, and 18 months, when applied alone or in combination with CMC. Laccase in combination with CMC increased SHC relative to the control. Laccase from different sources were equally effective in organic matter decomposition and thatch layer reduction. Laccase application for six months during the second year was effective in ceasing thatch layer buildup. This example indicates that application of laccase for six months in one year is effective to reduce the organic matter content and thatch layer thickness. Application of laccase for six months each year could be an effective means to prevent thatch layer accumulation.

Tables for Example 6:

TABLE 12

Description of laccase treatments applied on creeping bentgrass.

| Treatment No | Solution volume | Laccase activity | Application frequency | Cultural Mgt. | Source of laccase | Designation | Application time frame |
|---|---|---|---|---|---|---|---|
| T1 Control | 410 mL | 0 | 2 | No | NA | Control | 0-6 months<br>12-18 months |
| Rate of application | | | | | | | |
| T2 0.5 (2) | 410 mL | 0.5 | 2 | No | Sigma Aldrich | 0.5 (2) | 0-6 months |
| T3 1.0 (2) | 410 mL | 1.0 | 2 | No | Sigma Aldrich | 1.0 (2) | 0-6 months |
| T4 2.0 (2) | 410 mL | 2.0 | 2 | No | Sigma Aldrich | 2.0 (2) | 0-6 months |
| T5 4.0 (2) | 410 mL | 4.0 | 2 | No | Sigma Aldrich | 4.0 (2) | 0-6 months |
| Application frequency | | | | | | | |
| T6 2.0 (4) | 410 mL | 2.0 | 4 | No | Sigma Aldrich | 2.0 (4) | 0-6 months |
| T7 2.0 (8) | 410 mL | 2.0 | 8 | No | Sigma Aldrich | 2.0 (8) | 0-6 months |
| T8 2.0 (12) | 410 mL | 2.0 | 12 | No | Sigma Aldrich | 2.0 (12) | 0-6 months |
| Cultural management | | | | | | | |
| T9 CMC | 410 mL | 0 | 0 | Yes | NA | CMC | |
| T10 CMC + 2.0 | 410 mL | 2.0 | 4 | Yes | Sigma Aldrich | CMC + 2.0 (4) | 0-6 months |
| Laccase sources | | | | | | | |
| T11 CHI (2) | 410 mL | 2.0 | 2 | No | Industrial-China | CHI (2) | 0-6 months |
| T12 CHU (2) | 410 mL | 2.0 | 2 | No | University-China | CHU (2) | 0-6 months<br>12-18 months |

TABLE 13

Analysis of variance (ANOVA) table showing the effects of laccase treatments, treatment duration, and duration and treatment interactions on creeping bentgrass.

| | | Variation source | | | | | | | |
|---|---|---|---|---|---|---|---|---|---|
| | df | Organic matter ($OM_U$) (0-2.5 cm) | Organic matter ($OM_L$) (2.5-5.0 cm) | Organic matter (OM) (0-5.0 cm) | Thatch layer thickness TLT | Saturated hydraulic conductivity SHC | Acid-soluble lignin $L_S$ | Acid-insoluble lignin $L_I$ | Total lignin $L_T$ |
| | | | | | mean square value | | | | |
| Full Model | | | | | | | | | |
| Rep | 3 | 1429 | 973 | 779 | 5 | 123 | 282 | 60 | 167 |
| Treatment | 10 | 2583** | 316 | 515 | 40*** | 131*** | 37 | 2065*** | 1966*** |
| ErrorA (rep*treatment) | 30 | 699*** | 317* | 247** | 2 | 24 | 30 | 21 | 56 |
| Duration | 2 | 7934*** | 15 | 792** | 85*** | 110 | 1205*** | 69963*** | 79960*** |
| Duration*treatment | 20 | 316 | 181 | 106 | 2 | 24 | 36 | 970*** | 1127*** |
| Error | 66 | 221 | 194 | 105 | 2 | 39 | 66 | 26 | 123 |
| Rate of Application | | | | | | | | | |
| Rep | 3 | 4105 | 1368 | 1747 | 4 | 108 | 182 | 52 | 141 |
| Treatment | 4 | 400 | 139 | 201 | 53*** | 3 | 55 | 3029*** | 2980*** |
| Error A (rep*treatment) | 12 | 313 | 175*** | 146** | 0.6 | 4 | 32 | 19 | 42 |
| Duration | 2 | 2900*** | 112 | 120 | 29*** | 35 | 507** | 37614*** | 43511*** |
| Duration*treatment | 8 | 225 | 36 | 46 | 2 | 4 | 31 | 1696*** | 1982*** |
| Error | 30 | 249 | 37 | 40 | 1 | 23 | 59 | 25 | 101 |
| Appl. Frequency | | | | | | | | | |
| Rep | 3 | 1333 | 1134 | 522 | 3 | 55 | 73 | 19 | 41 |
| Treatment | 4 | 322 | 488 | 380 | 53*** | 4 | 59 | 2170*** | 1641*** |
| Error A (rep*treatment) | 12 | 663** | 464 | 302 | 1 | 5 | 43 | 35 | 78 |
| Duration | 2 | 4108*** | 173 | 404 | 64*** | 25 | 690*** | 35405*** | 38414*** |
| Duration*treatment | 8 | 496 | 290 | 95 | 1 | 4 | 47 | 2113*** | 1439*** |
| Error | 30 | 230 | 346 | 158 | 2 | 17 | 85 | 29 | 168 |

TABLE 13-continued

Analysis of variance (ANOVA) table showing the effects of laccase treatments, treatment duration, and duration and treatment interactions on creeping bentgrass.

| | | Variation source | | | | | | | |
|---|---|---|---|---|---|---|---|---|---|
| | | Organic matter $(OM_U)$ (0-2.5 cm) | Organic matter $(OM_L)$ (2.5-5.0 cm) | Organic matter (OM) (0-5.0 cm) | Thatch layer thickness TLT | Saturated hydraulic conductivity SHC | Acid-soluble lignin $L_S$ | Acid-insoluble lignin $L_I$ | Total lignin $L_T$ |
| | df | | | | mean square value | | | | |
| Cultural Management | | | | | | | | | |
| Rep | 3 | 194 | 122 | 58 | 2 | 75 | 110 | 36 | 31 |
| Treatment | 3 | 4865* | 252 | 821 | 49*** | 272* | 28 | 1668*** | 1388** |
| Error A (rep*treatment) | 9 | 906** | 195*** | 217** | 2 | 57 | 28 | 22 | 41 |
| Duration | 2 | 1343** | 132* | 436*** | 23** | 138 | 226** | 13999*** | 15053*** |
| Duration*treatment | 6 | 275 | 65 | 114 | 0.7 | 44 | 23 | 206*** | 317*** |
| Error | 24 | 225 | 38 | 47 | 3 | 74 | 32 | 15 | 52 |
| Laccase Sources | | | | | | | | | |
| Rep | 3 | 531 | 510 | 418 | 8 | 55 | 92 | 10 | 43 |
| Treatment | 2 | 1088* | 86 | 281 | 1 | 12* | 23 | 2909*** | 2703*** |
| Error A (rep*treatment) | 6 | 337 | 224 | 207 | 0.8 | 12 | 7 | 7 | 5 |
| Duration | 1 | 34 | 94 | 87 | 1 | 65* | 83 | 46837*** | 42974*** |
| Duration*treatment | 2 | 37 | 20 | 1 | 0.1 | 2 | 13 | 1360*** | 1622*** |
| Error | 9 | 193 | 128 | 102 | 2 | 9 | 68 | 32 | 84 |
| 2 Year Application | | | | | | | | | |
| Rep | 3 | 862 | 857 | 706 | 4 | 194 | 85 | 113 | 32 |
| Treatment | 1 | 4150** | 780 | 1520 | 15 | 75 | 57 | 1447*** | 926** |
| Error A (rep*treatment) | 3 | 120 | 381** | 330* | 3 | 56 | 7 | 2 | 12 |
| Duration | 2 | 3337* | 105 | 460* | 8* | 113 | 284* | 31421*** | 34666*** |
| Duration*treatment | 2 | 97 | 174 | 100 | 4 | 41 | 10 | 2142*** | 2362*** |
| Error | 12 | 526 | 56 | 74 | 2 | 125 | 60 | 49 | 105 |

*Significant at the 0.05 probability level
**Significant at the 0.01 probability level
***Significant at the 0.001 probability level

TABLE 14

Total organic matter content at three depths; 0-2.5 cm $(OM_U)$, 2.5-5.0 cm $(OM_L)$, and 0-5.0 cm (OM) at 6, 12 and 18 months after initiation of different laccase treatments applied on creeping bentgrass.

| | Total organic matter (0-2.5 cm) $OM_U$ | | | Total organic matter (2.5-5.0 cm) $OM_L$ | | | Total organic matter (0-5.0 cm) OM | | |
|---|---|---|---|---|---|---|---|---|---|
| Treatment group | 6 Months | 12 Months | 18 Months | 6 Months | 12 Months | 18 Months | 6 Months | 12 Months | 18 Months |
| | | | | | mg · g$^{-1}$ | | | | |
| Rate of Appl. | | | | | | | | | |
| Control | 132.0a† A‡ | 138.6a A | 140.1a A | 63.9a A | 62.8a A | 61.5ab A | 90.4a A | 89.7a A | 91.1b A |
| 0.5 (2) | 135.8a B | 139.6aA B | 155.3a A | 69.9a A | 69.0a A | 60.6ab A | 95.8a A | 95.2a A | 93.8ab A |
| 1.0 (2) | 131.5a A | 133.9ab A | 165.4a A | 64.9a A | 65.5a A | 67.6a A | 90.6a A | 91.6a A | 101.5a A |
| 2.0 (2) | 125.2a A | 127.7ab A | 156.9a A | 66.4a A | 59.0a B | 60.2ab B | 90.0a A | 85.5a A | 94.4ab A |
| 4.0 (2) | 129.9a AB | 117.1b B | 142.2a A | 63.1a A | 56.1a AB | 55.1b B | 88.6a A | 80.1a B | 85.8b AB |
| Freq. of Appl. | | | | | | | | | |
| Control | 132.0.a A | 138.6a A | 140.1b A | 63.9a A | 62.8a A | 61.5b A | 90.4a A | 89.7a A | 91.1c A |
| 2.0 (2) | 125.2a A | 127.7a A | 156.9ab A | 66.4a A | 59.0a B | 60.2b B | 90.0a A | 85.5a A | 94.4bc A |
| 2.0 (4) | 134.7a A | 141.7a A | 160.9ab A | 67.7a A | 73.2a A | 79.9a A | 93.8a A | 99.8a A | 109.8a A |
| 2.0 (8) | 134.8a A | 139.7a A | 148.8b A | 64.4a A | 65.0a A | 68.6ab A | 91.7a A | 93.0a A | 97.2abc A |
| 2.0 (12) | 131.6a B | 129.0a B | 183.9a A | 62.6a A | 94.5a A | 70.6ab A | 89.8a A | 106.7a A | 107.9ab A |
| Cultural Mgt. | | | | | | | | | |
| Control | 132.0abA | 138.6a A | 140.1aA | 63.9a A | 62.8a A | 61.5b A | 90.4a A | 89.7ab A | 91.1b A |
| CMC | 107.1b AB | 88.6b B | 118.4b A | 66.7a A | 60.5a A | 70.8ab A | 83.6a AB | 72.4b B | 90.51b A |
| 2.0 (4) | 134.7a A | 141.7a A | 160.9a A | 67.7a B | 73.2a AB | 79.9a A | 93.8a B | 99.8a B | 109.8a A |
| CMC + 2.0 (4) | 113.0ab AB | 97.9b B | 118.4b A | 71.a A | 63.9a A | 71.1ab A | 89.1a AB | 77.7b B | 89.8b A |
| Lacc. Sources | | | | | | | | | |
| 2.0 (2) | 125.2b A | 127.7a A | 156.9a A | 66.4a A | 59.0a B | 60.2b B | 90.0a A | 85.5a A | 94.4b A |
| CHI (2) | 136.8ab AB | 132.6a B | 163.9a A | 69.1a A | 65.6a A | 76.6ab A | 95.5a AB | 91.5a B | 108.9a A |
| CHU (2) | 152.2b A | 146.7a A | | 69.5a A | 68.5a A | | 101.1aA B | 98.1a B | |

TABLE 14-continued

Total organic matter content at three depths; 0-2.5 cm ($OM_U$), 2.5-5.0 cm ($OM_L$), and 0-5.0 cm (OM) at 6, 12 and 18 months after initiation of different laccase treatments applied on creeping bentgrass.

| Treatment group | Total organic matter (0-2.5 cm) $OM_U$ | | | Total organic matter (2.5-5.0 cm) $OM_L$ | | | Total organic matter (0-5.0 cm) OM | | |
|---|---|---|---|---|---|---|---|---|---|
| | 6 Months | 12 Months | 18 Months | 6 Months | 12 Months | 18 Months | 6 Months | 12 Months | 18 Months |
| | | | | | mg · g$^{-1}$ | | | | |
| Cont. appl | | | | | | | | | |
| 2.0 (2) | 125.2a A | 127.7a A | 156.9a A | 66.4a A | 59.0a B | 60.2a B | 90.0a A | 85.5a A | 94.4b A |
| CHU (2) | 152.2a A | 146.7a A | 189.8a A | 69.5a A | 68.5a A | 81.8a A | 101.1aA B | 98.1a B | 118.4a A |

†Means within a column in a treatment group (treatment effect) followed by the same lowercase letter are not significantly different according to LSD at $\alpha = 0.05$.
‡Means within a row in a treatment group (duration effect) followed by the same uppercase letter are not significantly different according to LSD at $\alpha = 0.05$.

TABLE 15

Saturated hydraulic conductivity (SHC), extractive-free acid-soluble ($L_S$) and-insoluble lignin ($L_I$) at 6, 12, and 18 months after initiation of different laccase treatments applied on creeping bentgrass.

| Treatment group | Saturated hydraulic conductivity SHC | | | Extractive-free Acid-soluble lignin $L_S$ | | | Extractive-free Acid-insoluble lignin $L_I$ | | |
|---|---|---|---|---|---|---|---|---|---|
| | 6 Mos. | 12 Mos. | 18 Mos. | 6 Mos. | 12 Mos. | 18 Mos. | 6 Mos. | 12 Mos. | 18 Mos. |
| | | cm h$^{-1}$ | | | | | mg · g$^{-1}$ | | |
| Rate of Appl. | | | | | | | | | |
| Control | 3.3ab†A‡ | 4.2a A | 6.9a A | 82.5a A | 76.2a A | 82.9a A | 279.6bC | 316.6c B | 326.8d A |
| 0.5 (2) | 2.3b A | 3.9a A | 4.7a A | 74.1bAB | 69.5a B | 80.8a A | 274.5c C | 297.6e B | 346.2c A |
| 1.0 (2) | 2.5b A | 3.8a A | 6.5a A | 74.7b A | 72.2a A | 82.6a A | 257.6dC | 306.7d B | 359.1b A |
| 2.0 (2) | 2.5b A | 5.5a A | 5.9a A | 73.6bc A | 72.9a A | 83.4a A | 250.0eB | 366.4a A | 365.7b A |
| 4.0 (2) | 5.3a A | 3.5a A | 4.9a A | 70.3c A | 75.6a A | 84.0a A | 291.2aC | 355.1b A | 379.3a A |
| Freq. of Appl. | | | | | | | | | |
| Control | 3.3ab A | 4.2a A | 6.9a A | 82.5a A | 76.2a A | 82.9a A | 279.6bC | 316.6d B | 326.8d A |
| 2.0 (2) | 2.5b A | 5.5a A | 5.9a A | 73.6c A | 72.9a A | 83.4a A | 250.0dB | 366.4a A | 365.7a A |
| 2.0 (4) | 1.6b A | 3.6a A | 4.0a A | 74.7bc B | 75.7a A | 85.0a A | 264.1c C | 306.2e B | 338.7c A |
| 2.0 (8) | 4.5a A | 4.2a A | 4.5a A | 77.7bAB | 65.4a B | 85.0a A | 280.8bC | 348.9b B | 371.0a A |
| 2.0 (12) | 3.1ab A | 4.3a A | 5.1a A | 76.7b A | 67.7a A | 80.3a A | 285.4aC | 338.4c B | 356.1b A |
| Cultural Mgt. | | | | | | | | | |
| Control | 3.3b A | 4.2a A | 6.9b A | 82.5a A | 76.2a A | 82.9a A | 279.6c C | 316.6c B | 326.8c A |
| CMC | 16.8a A | 9.9a A | 14.3ab A | 78.9b A | 74.4a A | 82.2a A | 289.2bC | 327.9b B | 339.9b A |
| 2.0 (4) | 1.6b A | 3.6a A | 4.0b A | 74.7c B | 75.7a A | 85.0a A | 264.1dC | 306.2d B | 338.7b A |
| CMC + 2.0 (4) | 8.1ab A | 7.7a A | 21.3a A | 78.7b A | 72.8a A | 79.0a A | 294.1aB | 343.3a A | 350.4a A |
| Lacc. Sources | | | | | | | | | |
| 2.0 (2) | 2.5a A | 5.5a A | 5.9a A | 73.6b A | 72.9a A | 83.4a A | 250.0bB | 366.4a A | 365.7ab A |
| CHI (2) | 2.5a A | 7.3a A | 4.3a A | 78.5aAB | 73.1a B | 84.5a A | 275.9aB | 359.6b A | 355.1b A |
| CHU (2) | 3.4a A | 8.0a A | | 79.0aAB | 73.9a B | | 248.6bC | 313.4c B | |
| Cont. Appl | | | | | | | | | |
| 2.0 (2) | 2.5a A | 5.5a A | 5.9a A | 73.6a A | 72.9a A | 83.4a A | 250.0aB | 366.4a A | 365.7a A |
| CHU (2) | 3.4a A | 8.0a A | 14.8a A | 79.0aAB | 73.9a B | 86.3a A | 248.6aC | 313.4b B | 373.4a A |

†Means within a column in a treatment group (treatment effect) followed by the same lowercase letter are not significantly different according to LSD at $\alpha = 0.05$.
‡Means within a row in a treatment group (duration effect) followed by the same uppercase letter are not significantly different according to LSD at $\alpha = 0.05$.

Many variations and modifications may be made to the embodiments described in the preceding Examples. All such modifications and variations are intended to be included herein within the scope of this disclosure and protected by the following claims.

REFERENCES

Alder, E. 1977. Lignin chemistry-past, present and future. Wood Sci. Technol. 11: 169-218.

Allison, S. D., Vitousek, P. M., 2005. Responses of extracellular enzymes to simple and complex nutrient inputs. Soil Biology & Biochemistry 37, 937-944.

Baldrian, P. 2006. Fungal laccases-occurrence and properties. FEMS Microbiol Rev. 30: 215-242.

Banoub, J. H., and M. Delmas. 2003. Structural elucidation of wheat straw lignin polymer by atmospheric pressure chemical ionization tandem mass spectrometry and matrix-assisted laser desorption/ionization time-of-flight mass spectrometry. J. Mass Spectrom. 38: 900-903.

Barton, L., G. G. Y. Wan, R. P. Buck, and T. D. Colmer. 2009. Effectiveness of cultural thatch-mat controls for young and mature kikuyu turfgrass. Agron. J. 101: 67-74.

Beard, J. B. 1973. Turfgrass: Science and culture. Prentice Hall Inc. Englewood Cliffs, N.J.

Blanchette, R. A. 1984. Screening wood decayed by white rot fungi for preferential lignin degradation. Appl. Environ. Microbiol. 48: 647-653.

Boyle, C. D, B. R. Kropp and I. D. Reid. 1992. Solubilization and mineralization of lignin by white rot fungi. Applied and Environmental Microbiology 58 (3): 3217-3224.

Bunnell, B. T., L. B. McCarty, and H. S. Hill. 2001. Summer cultivation effects on sand based creeping bentgrass golf green. Int. Turfgrass Res. J. 9:3-9.

Callahan, L. L., W. L. Sanders, J. M. Parham, C. A. Harper, L. D. Lester, and E. R. McDonald. 1998. Cultural and chemical controls of thatch and their influence on rootzone nutrients in bentgrass green. Crop Sci. 38:181-187.

Canaway, P. M., S. P. Isaac, and R. A. Bennett. 1986. The effects of mechanical treatments on the water infiltration rate of a sand playing surface for association football. J. Sports Turf Res. Inst. 62: 67-73.

Carley, D. S., D. Goodman, S. Sermons, W. Shi, D. Bowman, G. Miller, and T. Rufty. 2011. Soil Organic matter accumulation in creeping bentgrass greens: A hronosequence with implications for management and carbon sequestration. Agron. J. 103 (3): 604-610.

Carrow, R. N. 2003. Surface organic matter in bentgrass greens. USGA Turfgrass Environ. Res. Online 2(17): 1-10.

Carrow, R. N. 2004. Surface organic matter in bentgrass greens. Golf Course Mgt. 72(5): 96-101.

Carrow, R. N., B. J. Johnson, and R. E. Burns. 1987. Thatch and quality of tifway bermudagrass turf in relation to fertility and cultivation. Agron. J. 79: 524-530.

Causo F., and C. Schuler. 2000. Enzyme multilayers on colloid particles: Assembly, stability, and enzymatic activity. Langmuir. 16: 9595-9603.

Chen, Y. R., and S. Sarkanen. 2003. Macromolecular lignin replication: A mechanistic working hypothesis. Phytochemistry Rev. 2: 235-255.

Couillard, A., A. J. Turgeon, and P. E. Rieke. 1997. New insights into thatch biodegradation. Int. Turfgrass Res. J. 8:427-435.

Davin, L. B. and N. G. Lewis 2003. A historical perspective on lignin biosynthesis: Monolignol, allylphenol and hydroxycinnamic acid coupling and downstream metabolism. Phytochemistry Rev. 2: 257-288.

Del Rio, J. C., G. Marques, J. Rencoret, A. T. Martinez, and A. Gutierrez. 2007. Occurrence of naturally acetylated lignin units. J. Agric. Food Chem. 55: 5461-5466.

Dunn, J. H., K. M. Sheffer, and P. M. Halisky. 1981. Thatch and quality of Meyer zoysia in relation to management. Agron. J. 73: 949-952.

Eggens, J. L. 1980. Thatch control on creeping bentgrass turf. Can. J. Plant Sci. 60:1209-1213.

Engel, R. E. 1954. Thatch on turf and its control. Golf Course Rep. 22 (5): 12-14.

Engel, R. E., and R. B. Alderfer. 1967. The effect of cultivation, top-dressing, lime, N, and wetting agent on thatch development on ¼-inch bentgrass over a 10-year period. N. J. Agric. Exp. Stn. Bull. 818:32-45.

Engelke, M. C., V. G. Lehman, W. R. Kneebone, P. F. Colbaugh, J. A. Reinert, and W. E. Knoop. 1995. Registration of 'Crenshaw' creeping bentgrass. Crop Sci. 35:589.

Gilbeault, V. A., R. Baldwin, I. Bivins, and D. Hanson. 1976. Evaluation of biological dethatching materials. California Turfgrass Culture. 26: 29-30.

Gold, M. H. and M. Alic. 1993. Molecular biology of lignin-degrading basidiomycete *phanerochaete chryosporium*. Microbiology and Molecular biology reviews. 57(3): 605-622.

Gallo, M., Amonette, R., Lauber, C., Sinsabough, R. L., Zak., D. R., 2004. Microbial community structure and oxidative enzyme activity in nitrogen-amended north temperate forest soils. Microbial Ecology 48, 218-229.

Hartwiger, C. 2004. The importance of organic matter dynamics: How research uncovered the primary cause of secondary problems. USGA Green Section Record 42(3): 9-11.

Johnson, B. J., R. N. Carrow, and R. E. Burns. 1987. Bermudagrass turf response to mowing practices and fertilizer. Agron. J. 79:677-680.

Kirk, T. K., and R. L. Farrell. 1987. Enzymatic "combustion": Theicrobial degradation of lignin. Annu. Rev. Microbiol. 41: 465-501.

Kirk, T. K., W. J. Connors, R. D. Bleam, and G. Jeikus. 1976. Requirements for a growth substrate during lignin decomposition by two wood-rotting fungi. Appl. Environ. Microbiol. 32: 192-194.

Kirk, T. K., W. J. Connors, R. D. Bleam, W. F. Hackett, and J. G. Jeikus. 1975. Preparation and microbial decomposition of synthetic [$^{14}C$] lignins. PANS. 72: 2515-2519.

Koch, A. L., 1985. The macroeconomics of bacterial growth. In: Fletcher, M., Floodgate, D. G., (Eds.), Bacteria in their natural environments. Academic Press, London, pp. 1-42.

Lancaster, D. L., A. W. Redo, and V. A. Gibleault. 1977. Evaluation of biological thatch decomposing materials. California Turfgrass Culture. 27: 29-30

Landreth, J., D. Karcher, and M. Richardson. 2008. Cultivating to manage organic matter in sand based putting greens: University of Arkansas researchers provide important insight for managing organic buildup on putting greens. USGA Turfgrass Environ. Res. Online 46(1): 16-19.

Ledeboer, F. B., and C. R. Skogley. 1967. Investigations into the nature of thatch and methods for its decomposition. Agron. J. 59: 320-323.

Liu Z. M., Liu Y. L., Yang H. F., Yang Y., Shen G. L., and R. Q. Yu. 2005. A phenol biosensor based on immobilizing tyrosinase to modified core-shell magnetic nanoparticles supported at a carbon paste electrode. Analytica Chimica Acta 533: 3-9.

Martin, S. B., and J. L. Dale. 1980. Biodegradation of turf thatch with wood-decay fungi. Phytopathology. 70: 297-301.

McCarty, L. B., M. F. Gregg, and J. E. Toler. 2007. Thatch and mat management in an established creeping bentgrass green. Agron. J. 99: 1530-1537.

McCarty, L. B. 2005. Best golf course management practices. $2^{nd}$ ed. Prentice Hall Inc. Upper Saddle River, N.J.

McCarty, L. B., M. F. Gregg, J. E. Toler, J. J. Camberato, and H. S. Hill. 2005. Minimizing thatch and mat development in a newly seeded creeping bentgrass golf green. Crop Sci. 45:1529-1535.

McCoy, E. L. 1992. Quantitative physical assessment of organic materials used in sports turf rootzone mixes. Agron. J. 84: 375-381.

McWhirter, E. L., and C. Y. Ward. 1976. Effect of vertical mowing and aerification of golf green quality. Mississipi Agric. For. Exp. Stn. Res. Rep. 2 (12). 1-2.

Mester, T., E. Varela, and M. Tien. 2004. Wood degradation by brown-rot and white-rot fungi. The Mycota II: Genetics and biotechnology. $2^{nd}$ edition. Springer-Verlag, Berlin, Heidelberg.

Munoz, C., F. Guillen, A. T. Martinez, and M. J. Martinez. 1997. Laccase isozymes of *Pleurotus eryngii*: Characterization, catalytic properties, and participation in activation of molecular oxygen and $Mn^{2+}$ oxidation. App. Environ. Microbiol. 63: 2166-2174.

Murdoch, C. L., and J. P. Barr. 1976. Ineffectiveness of commercial microorganism inoculums in breaking down thatch in common bermudagrass in Hawaii. HortScience. 11:488-489.

Murray, J. J., and F. V. Juska. 1977. Effect of management practices on thatch accumulation, turf quality, and leaf spot damage in common Kentucky bluegrass. Agron. J. 69: 365-369.

Nakayama T. and T. Amachi. 1999. Fungal peroxidases: its structure, function and application. *Journal of Molecular catalysisB: Enzymatic*. 6(3): 185-198.

National Renewable energy Laboratory (NREL). Chemical Analysis and Testing Laboratory Analytical Procedures; Preparation of samples for compositional analysis; and Determination of structural carbohydrates and lignin in biomass: LAP (2008 a & b). NREL, Golden, Colo., USA.

O'Brien, P., and C. Hartwiger. 2003. Aeration and topdressing for the $21^{st}$ century: Two old concepts are linked together to offer up-to-date recommendations. USGA Green Section Record 41(2): 1-7.

Olander, L. P., Vitousek, P. M., 2000. Regulation of soil phosphatase and chitinase activity by N and P availability. Biogeochemistry 49, 175-190.

Otjen, L., and R. Blanchette. 1987. Assessment of 30 white rot basidiomycetes for selective lignin degradation. Holzforschung. 41: 343-349.

Otjen, L., and R. Blanchette. 1987. Assessment of 30 white rot basidiomycetes for selective lignin degradation. Holzforschung. 41: 343-349.

Park, J. W., J. Dec, J. E. Kim, and J. M. Bollag. 1999. Effect of humic constituents on the transformation of chlorinated phenols and anilines in the presence of oxidoreductive enzymes or birnessite. Environ. Sci. Tech. 33: 2028-2034.

Ralph, J., M. Bunzel, J. M. Marita, R. D. Hatfield, F. Lu, H. Kim, P. F. Schatz, J. H. Grabber, and H. Steinhart. 2004. Peroxidase dependent cross linking reactions of p-hydroxicinnamates in lant cellwalls. Phytochemistry Rev. 3: 79-96.

Rieke, P. E. 1994. Sand topdressing: here are we going? Golf Course Mgt. 62:36-38.

Roberts, E. G., and E. J. Bredakis. 1960. What, why and how of turfgrass root development. Golf Course Rep. 28:13-24.

Roper, J. C., J. M. Sarkar, J. Dec, and J. M. Bollag. 2000. Enhanced enzymatic removal of chlorophenols in the presence of co-substrates. Water Res. 29:2720-2724.

SAS Institute Inc. 1994. The SAS system for windows. Release 9.2. SAS Inst., Cary, N. C.

Saiya-Cork, K. R., Sinsabough, R. L., Zak, D. R., 2002. The effects of long term nitrogen deposition on extracellular activity in an *Acer saccharum* forest soil. Soil Biology & Biochemistry 34, 1309-1315.

Sartain, J. B., and B. G. Volk. Influence of selected white-rot fungi and topdressings on the composition of thatch components of four turfgrasses. Agron. J. 76: 359-362.

SAS Institute Inc. 1994. The SAS system for windows. Release 9.2. SAS Inst., Cary, N. C.

Sidhu S. S. 2012. Enzymatic removal of lignin from plant materials: Potential applications. Ph.D. diss., The Univ. of Georgia, Athens.

Sidhu, S. S., Q. Huang, R. N. Carrow, and P. L. Raymer. 2012. Use of fungal laccases to facilitate biodethatching: A new approach. HortScience. 47(10): 1536-1542.

Sidhu, S. S., Q. Huang, R. N. Carrow, and P. L. Raymer. 2013a. Laccase mediated changes in physical and chemical composition properties of thatch layer in creeping bentgrass (*Agrostis stolonifera* L.). Soil Biol. Biochem., doi: 10.1016/j.soilbio.2013.04.002.

Sidhu, S. S., Q. Huang, R. N. Carrow, and P. L. Raymer. 2013b. Efficacy of fungal laccase to facilitate biodethatching in bermudagrass and zoysiagrass. Agron. J., doi: 10.2134/agronj2012.0470.

Sidhu, S. S., Q. Huang, R. N. Carrow, and P. L. Raymer. 2014. Optimizing laccase application on creeping bentgrass (*Agrostis stolonifera* L.) to facilitate biodethatching. Crop Sci., doi: 10.2135/cropsci2013.09.0612

Sinsabaugh, R. L., R. K. Antibus, A. E. Linkins, C. A. Mcclaugherty, L. Rayburn, D. Repert, T. Weiland. 1993. Wood decomposition—nitrogen and phosphorus dynamics in relation to extracellular enzyme-activity. Ecology. 74: 1586-1593.

Sinsabaugh, R. L., Gallo, M. E., Lauber, C., Waldrop, M. P., Zack, D. R. 2005. Extracellular enzyme activities and soil organic matter dynamics for nothern hardwood forests receiving stimulated nitrogen deposition. Biogeochemistry 75, 201-215.

Smith, G. S. 1979. Nitrogen and cultivation influence on putting green thatch and soil. Agron. J. 71:680-684.

Smiley, R. W., M. Crawen Fowler, R. T. Kane, A. M. Petrovic, and R. A. White. 1985. Fungicide effects on thatch depth, thatch decomposition rate, and growth of Kentucky bluegrass. Agron. J. 77: 597-602.

Soper, D. Z., J. H. Dunn, D. D. Minner, and D. A. Sleper. 1988. Effects of clipping disposal, nitrogen, and growth retardants on thatch and tiller density in zoysiagrass. Crop Sci. 28: 325-328.

Stoilova, I., A. Krastanov, and V. Stanchev. 2010. Properties of crude laccase from *Trametes versicolor* produced by solid-substrate fermentation. Adv. Bioscience Biotech. 1: 208-215.

Taylor B. R., D. Parkinson, W. F. J. Parsons. 1989. Nitrogen and lignin content as predictors of litter decay rates: A microcosm test. Ecology. 70: 97-104.

Thurston, C. F. 1994. The structure and function of fungal laccases. Microbiol. 140:19-16.

U. S. Golf Association Green Section Staff. 1973. Refining the Green Section specifications for putting green construction. USGA Green Sect. Rec. 11(3): 1-8.

Weston, J. B., and J. H. Dunn. 1985. Thatch and quality of Meyer *zoysia* in response to mechanical cultivation and nitrogen fertilization. P. 449-458. In F. Lemaire (ed.) Proc. $5^{th}$ Int. Turfgrass Res. Conf., Avignon, France. 1-5 Jul. 1985. Institut National de la Recherche Agronomique, Paris, France.

White, R. H., and R. Dickens. 1984. Thatch accumulation in bermudagrass as influenced by cultural practices. Agron. J. 76: 19-22.

Wong, D. W. S. 2009. Structure and action mechanism of ligninolytic enzymes. Appl. Biochem Biotechnol. 157: 174-209.

Yao, H., Bowman, D., Rufty, T., Shei, W., 2009. Interactions between N fertilizations, grass clipping addition and pH in turf ecosystems: Implications for soil enzyme activities and organic matter decomposition. Soil Biology & Biochemistry 41, 1425-1432.

Yao, H., Bowman, D., Shei, W., 2011. Seasonal variations of soil microbial biomass and activity in warm- and cool-season turfgrass systems. Soil Biolology & Biochemistry 43, 1536-1543.

We claim:

1. A method of degrading turf thatch, comprising:
   contacting the turf thatch of an area of turfgrass, where the area of turfgrass forms a ground covering on a plot of land, with a composition comprising an isolated fungal laccase enzyme from a species of white rot fungi selected from: *Trametes versicolor* and a species from the *Pycnoporus* genus,
   wherein the isolated laccase enzyme composition degrades thatch in the area of turfgrass and wherein the amount of turf thatch in the area of turfgrass, measured as thatch layer thickness, is reduced by a measureable amount after treatment with the isolated laccase enzyme composition, as compared to the amount of turf thatch in the area of turfgrass before treatment.

2. The method of claim 1, wherein the composition further comprises a mediator.

3. The method of claim 1, wherein the mediator is chosen from the following:
   catechol, guaiacol, ABTS, and violuric acid.

4. The method of claim 1, wherein the mediator comprises guaiacol.

5. The method of claim 1, wherein the composition is applied to the turf thatch in an amount of about 0.1 to about 20 units/cm$^2$ of turf area.

6. The method of claim 1, wherein the composition is applied to the turf thatch in an amount of about 2.0 units/cm$^2$ or more of turf area.

7. The method of claim 1, wherein the composition is applied to turf thatch at intervals ranging from one application about every 56 weeks to one application about once a week.

8. The method of claim 1, wherein the composition is applied in an amount of about 2.0 to about 4.0 units/cm$^2$ at a rate of one application about every 8 weeks to one application about every 2 weeks.

9. The method of claim 1, wherein the composition is applied in a specified amount at a set frequency of application for a period of about 6 months or more.

10. The method of claim 1, wherein the composition is applied at a rate of one application every 8 weeks to one application about every 2 weeks for a period of about 6 months or more.

11. The method of claim 1, wherein the turf grass is selected from the group of turf grasses comprising: bermudagrass, bentgrass, and zoysiagrass.

12. The method of claim 1, wherein the area of turfgrass is an area selected from: a lawn, a field, and a golf course.

13. The method of claim 1, wherein the amount of turf thatch in the area of turfgrass, measured as thatch layer thickness, is reduced by at least 18% after treatment with the isolated laccase enzyme composition as compared to the amount of turf thatch in the area of turfgrass before treatment.

14. A method of degrading turf thatch, comprising:
    contacting an area of turfgrass on a lawn, a field, a golf course, or other plot of land with an aqueous composition comprising an isolated fungal laccase enzyme from a species of white rot fungi selected from: *Trametes versicolor* and a species from the *Pycnoporus* genus, wherein the aqueous isolated laccase enzyme composition is applied to the area of turfgrass a rate of one application about every 8 weeks to one application about every 2 weeks,
    wherein the isolated laccase enzyme degrades thatch in the area of turfgrass such that the thickness of a thatch layer in the area of turfgrass is reduced by a measureable amount after treatment with the isolated laccase enzyme composition, as compared to the thickness of turf thatch in the area of turfgrass before treatment or such that the thickness of a thatch layer in the area of turfgrass is less than the thickness of a thatch layer in a comparable area of turfgrass not receiving treatment with the isolated laccase enzyme composition.

* * * * *